United States Patent
Karp et al.

(10) Patent No.: US 6,880,576 B2
(45) Date of Patent: Apr. 19, 2005

(54) MICROFLUIDIC DEVICES FOR METHODS DEVELOPMENT

(75) Inventors: Christoph D. Karp, Pasadena, CA (US); Stephen D. O'Connor, Pasadena, CA (US); Eugene Dantsker, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/838,877

(22) Filed: May 3, 2004

(65) Prior Publication Data

US 2004/0238052 A1 Dec. 2, 2004

Related U.S. Application Data

(63) Continuation-in-part of application No. 10/165,448, filed on Jun. 7, 2002, now Pat. No. 6,729,352.
(60) Provisional application No. 60/296,882, filed on Jun. 7, 2001.

(51) Int. Cl.[7] .................................................. F15C 1/14
(52) U.S. Cl. ........................ 137/806; 137/807; 137/833; 204/601; 73/61.55
(58) Field of Search ................................ 137/833, 806, 137/807, 803; 204/601; 435/287.5; 422/100, 102; 73/61.55

(56) References Cited

U.S. PATENT DOCUMENTS

| | | | |
|---|---|---|---|
| 4,604,198 A | | 8/1986 | Dailey et al. ............. 210/198.2 |
| 4,669,502 A | * | 6/1987 | Lonardi et al. ......... 137/624.18 |
| 5,800,784 A | * | 9/1998 | Horn .......................... 422/101 |
| 5,922,591 A | * | 7/1999 | Anderson et al. ........ 435/287.2 |
| 6,043,080 A | * | 3/2000 | Lipshutz et al. ......... 435/287.2 |
| 6,090,278 A | | 7/2000 | Lally et al. .............. 210/198.2 |
| 6,171,486 B1 | | 1/2001 | Green et al. ............. 210/198.2 |
| 6,221,252 B1 | | 4/2001 | Hargro et al. .............. 210/656 |
| 6,240,790 B1 | | 6/2001 | Swedberg et al. ....... 73/863.21 |
| 6,418,968 B1 | * | 7/2002 | Pezzuto et al. ............. 137/833 |
| 6,461,515 B1 | | 10/2002 | Safir et al. ................. 210/656 |
| 6,485,069 B1 | | 11/2002 | Anderson .................... 292/175 |
| 6,499,499 B2 | | 12/2002 | Dantsker et al. ................ 137/1 |
| 6,561,208 B1 | * | 5/2003 | O'Connor et al. ....... 137/15.18 |
| 6,641,783 B1 | | 11/2003 | Pidgeon et al. ............... 422/70 |
| 6,743,356 B1 | | 6/2004 | Fermier et al. .......... 210/198.2 |
| 6,749,749 B2 | | 6/2004 | Xie et al. ................ 210/198.2 |
| 6,812,030 B2 | | 11/2004 | Ozbal et al. ................. 436/50 |
| 2002/0048536 A1 | | 4/2002 | Bergh et al. ................ 422/130 |
| 2003/0092056 A1 | | 5/2003 | Nagasawa ...................... 435/6 |

FOREIGN PATENT DOCUMENTS

| | | |
|---|---|---|
| EP | 1 178 309 A1 | 2/2002 |
| WO | WO 00/31528 | 6/2000 |
| WO | WO 01/86283 A3 | 11/2001 |
| WO | WO 02/22250 A2 | 3/2002 |
| WO | WO 02/056006 A2 | 7/2002 |

OTHER PUBLICATIONS

Poole, Colin F., "5.6 Coupled–Column Systems," *The essence of chromatography*, 2003 Elsevier Science B.V., Amsterdam, The Netherlands, pp. 451–455.

Poole, Colin F., "8.4.2 Column Technology," *The essence of chromatography*, 2003 Elsevier Science B.V., Amsterdam, The Netherlands, pp. 664–668.

* cited by examiner

*Primary Examiner*—A. Michael Chambers
(74) *Attorney, Agent, or Firm*—Vincent K. Gustafson

(57) ABSTRACT

Microfluidic devices with multiple fluid process regions for subjecting similar samples to different process conditions in parallel are provided. One or more common fluid inputs may be provided to minimize the number of external fluid supply components. Solid materials such as chromatographic separation media or catalyst media is preferably provided in each fluid process region. Solid materials may be supplied to the devices in the form of slurry, with particles retained by porous elements or frits. Different fluid process regions may having different effective lengths, different solid material types or amounts, or may receive different ratios of common fluids supplied to the device. The flow resistances of dissimilar fluid process regions may be balanced passively with the addition of impedance elements in series with each fluid process region.

41 Claims, 43 Drawing Sheets

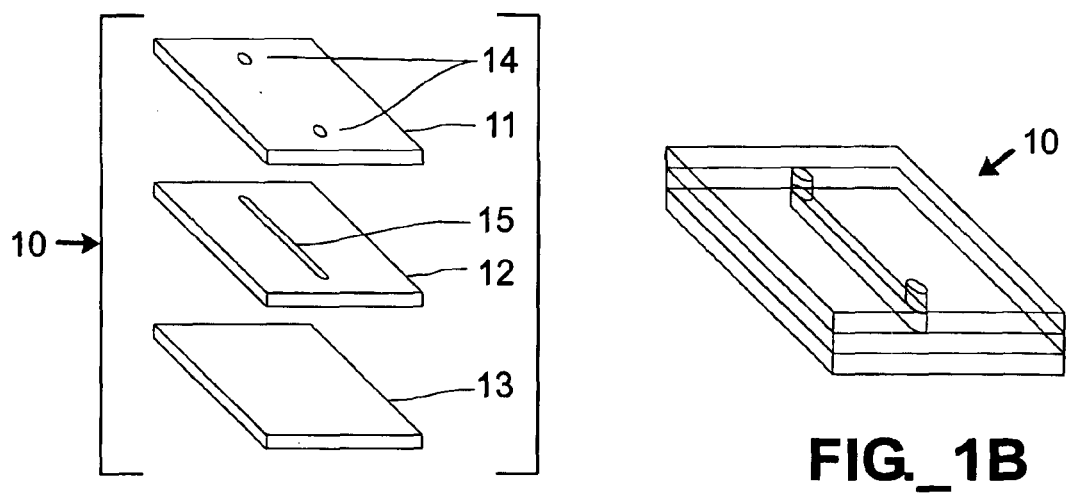
FIG._1A
FIG._1B

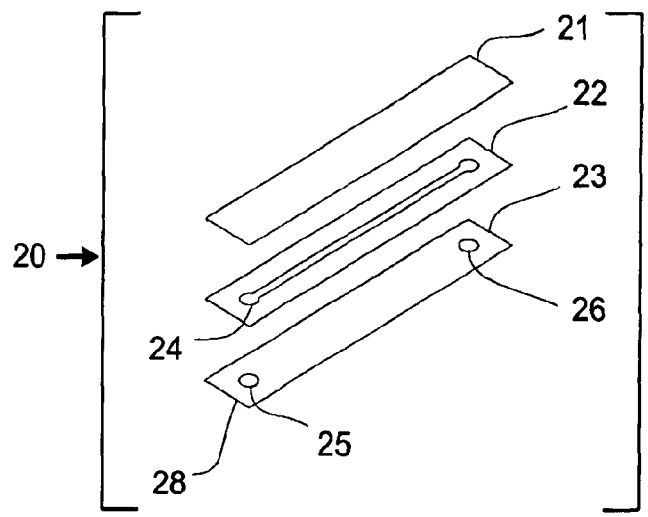
FIG._2A
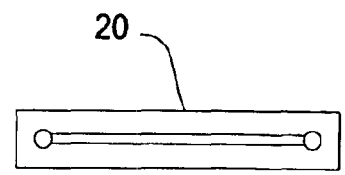
FIG._2B
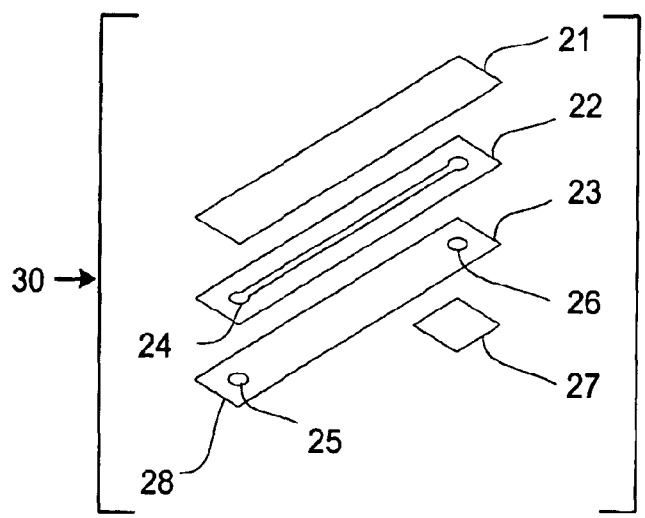
FIG._2C
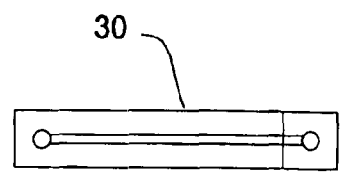
FIG._2D

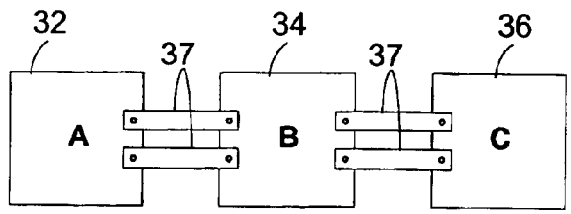
FIG._3A
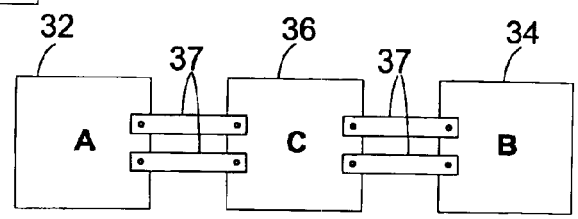
FIG._3B
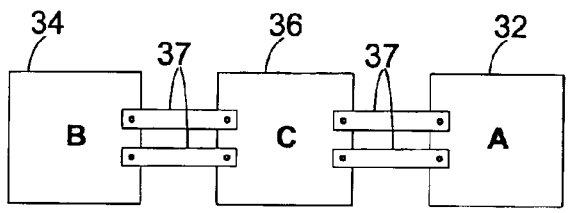
FIG._3C
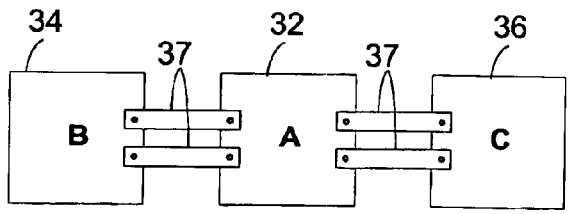
FIG._3D
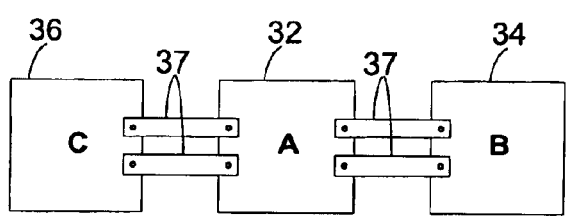
FIG._3E
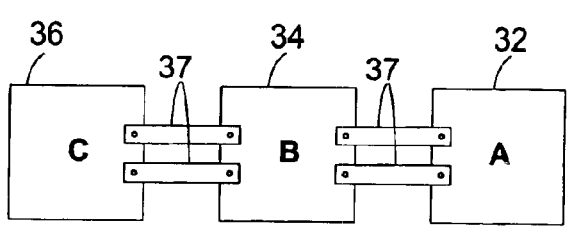
FIG._3F

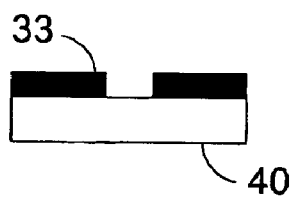
FIG._4A
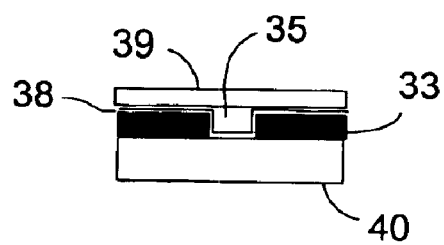
FIG._4C
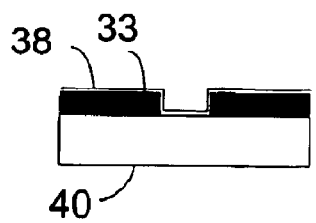
FIG._4B
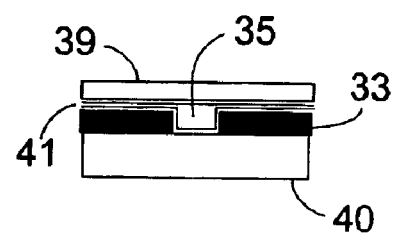
FIG._4D
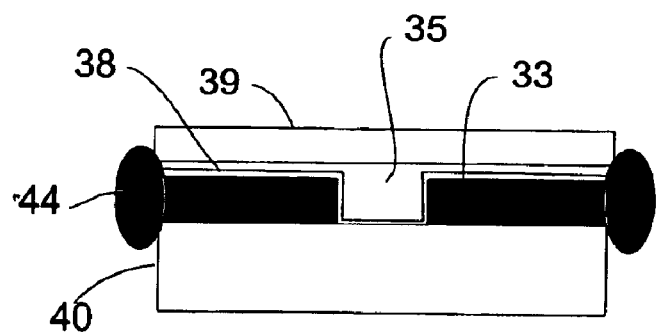
FIG._4E

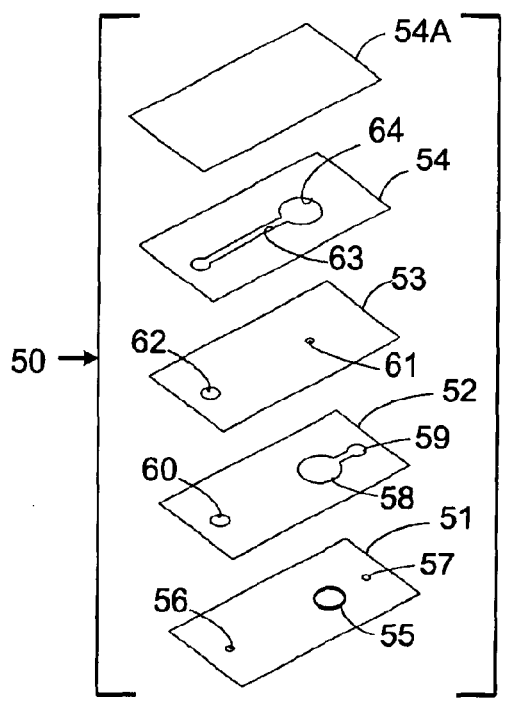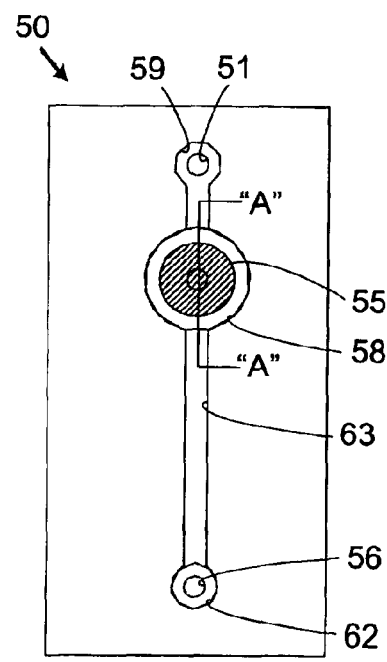
FIG._5A
FIG._5B
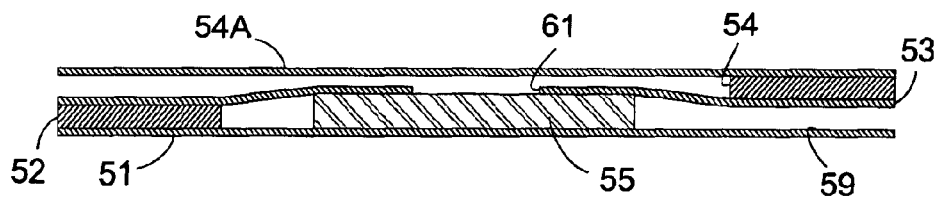
FIG._5C

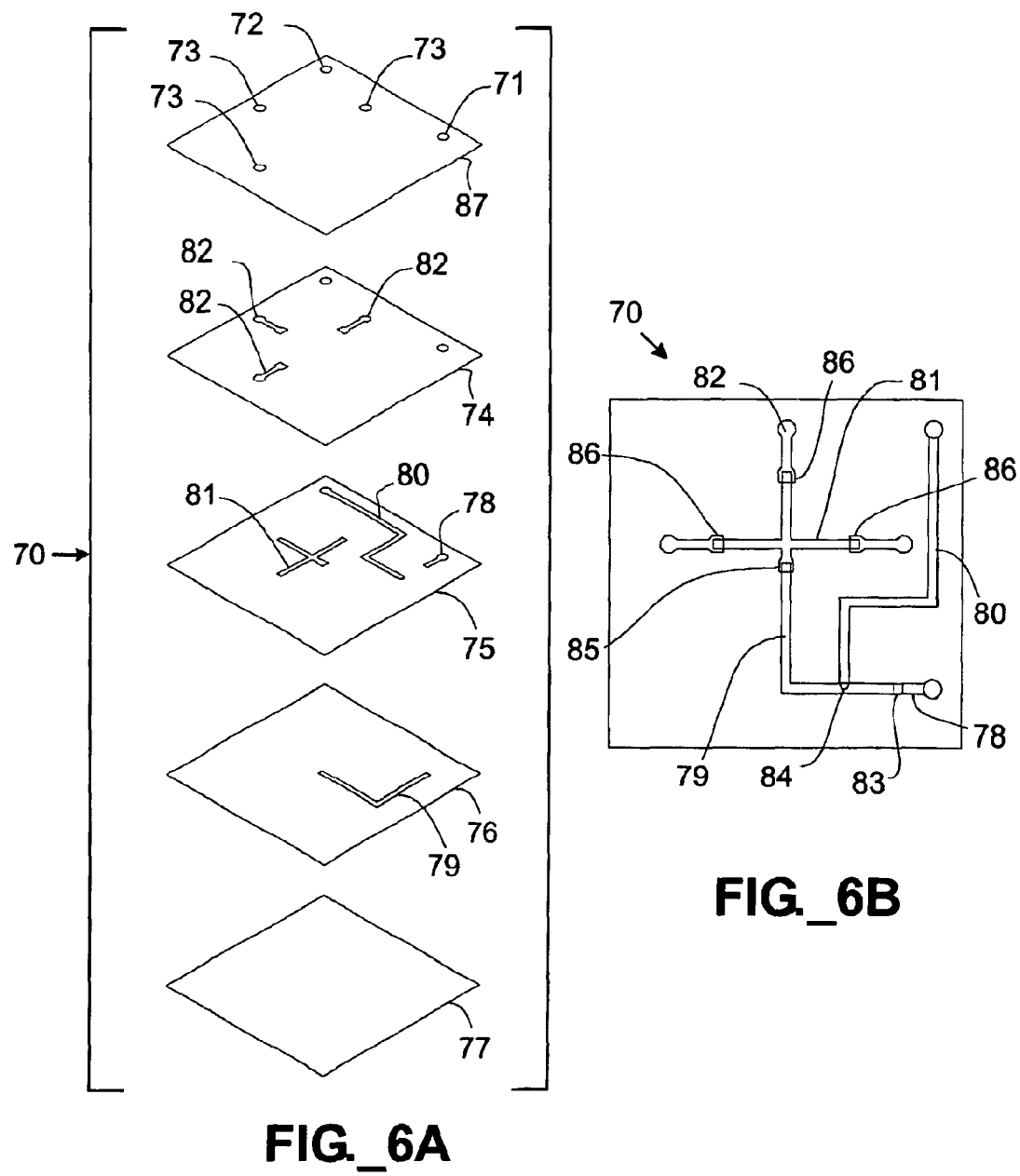
FIG._6A
FIG._6B

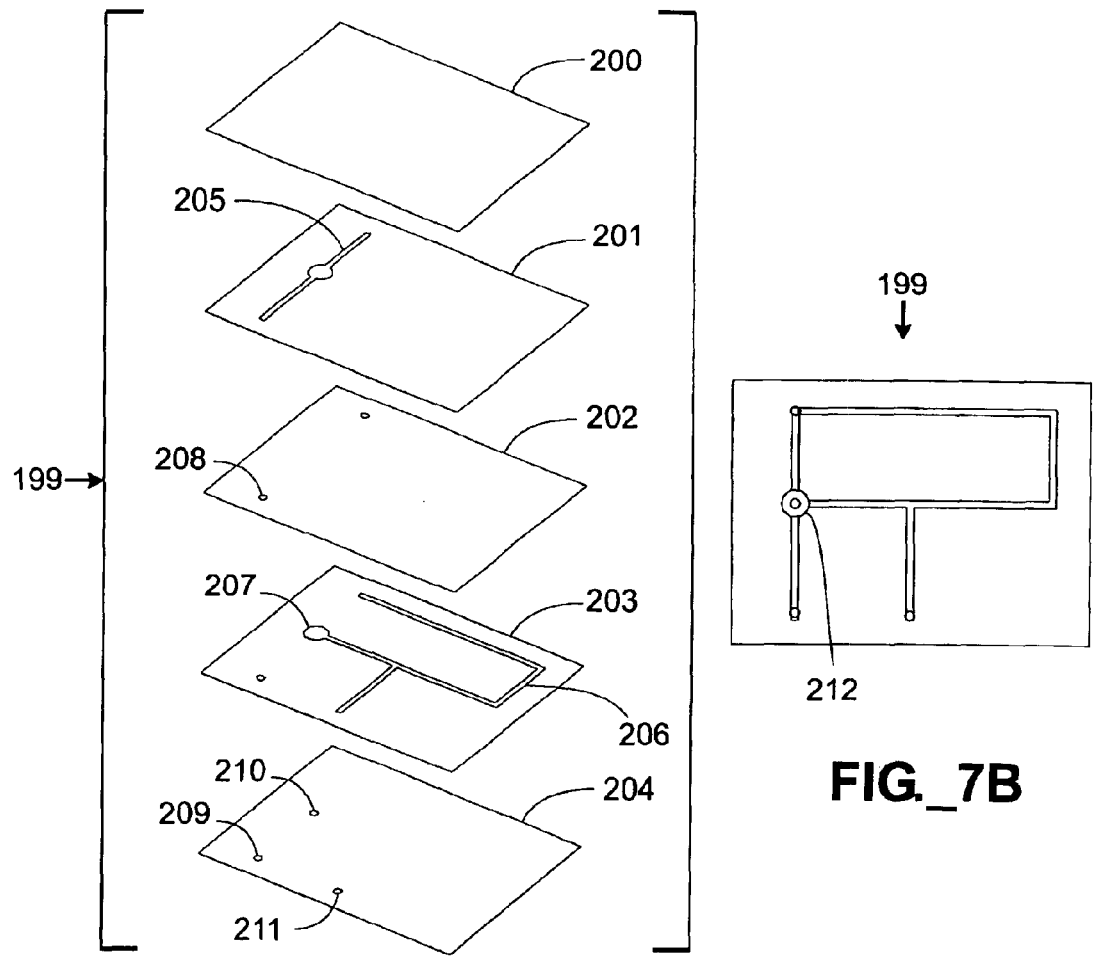
FIG._7A
FIG._7B

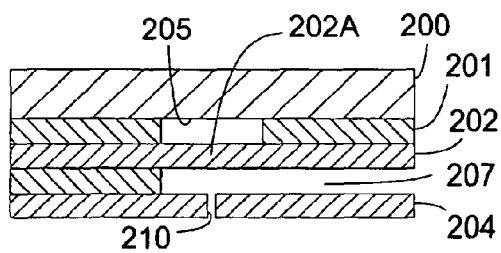
FIG._7C
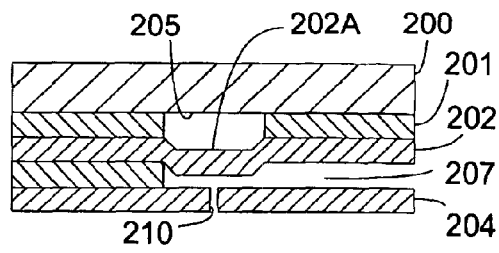
FIG._7D
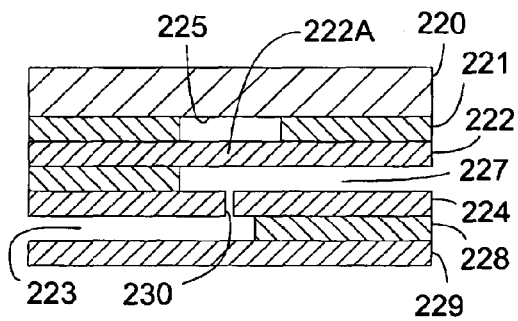
FIG._7E
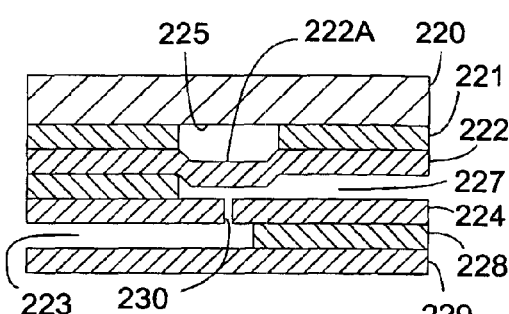
FIG._7F

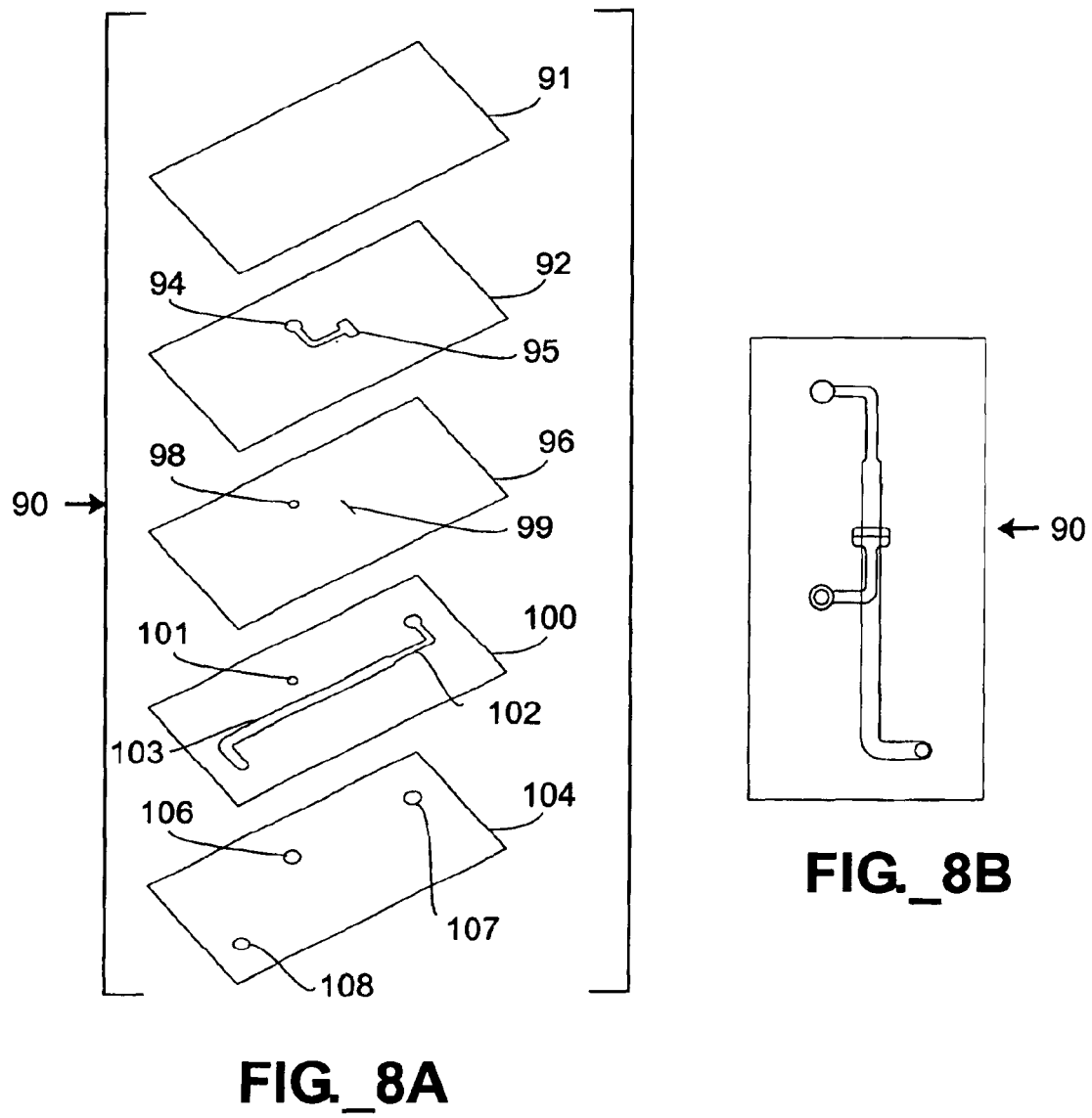
FIG._8A
FIG._8B

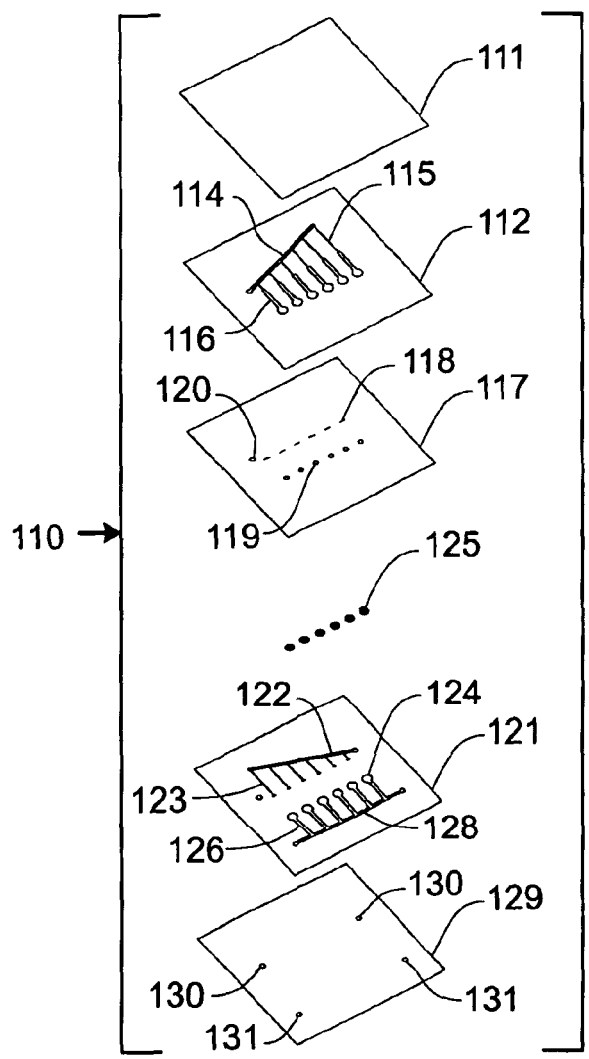
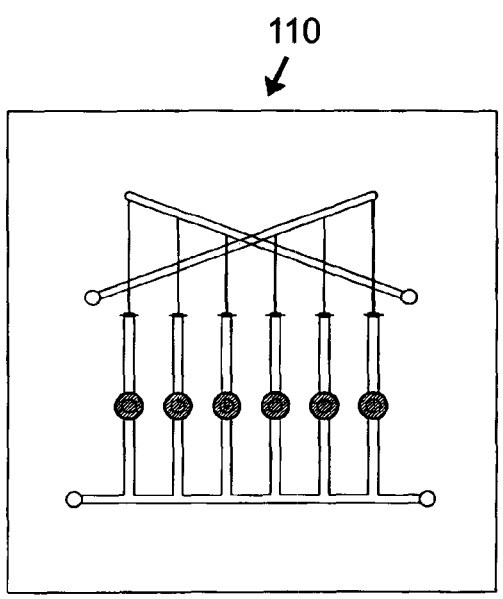
FIG._9A
FIG._9B

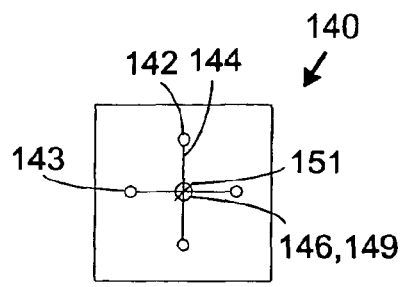
FIG._10A
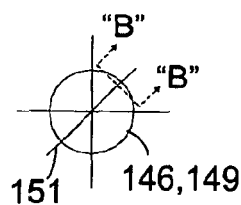
FIG._10B
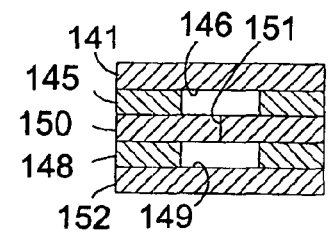
FIG._10C
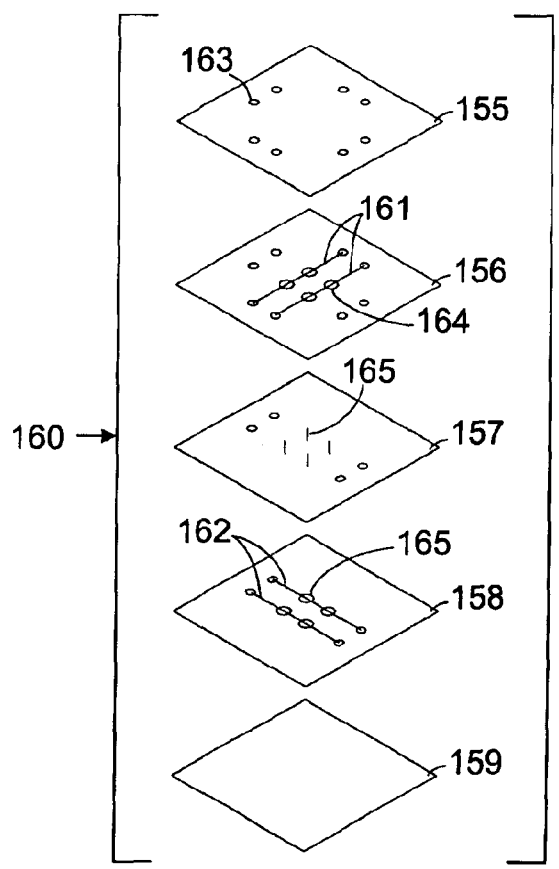
FIG._11A
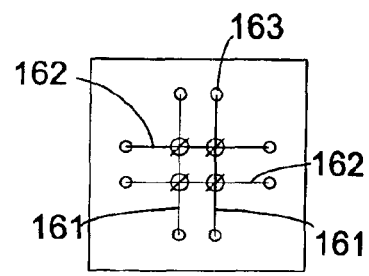
FIG._11B

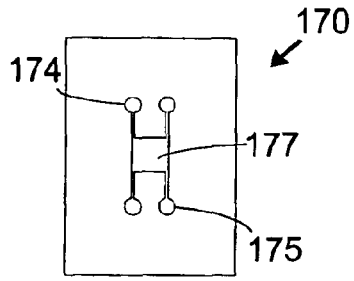
FIG._12A
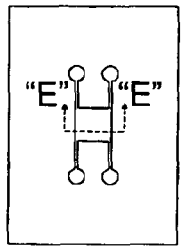
FIG._12B
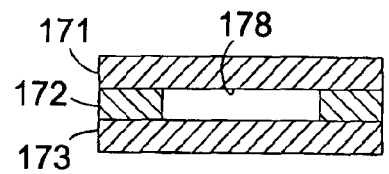
FIG._12C
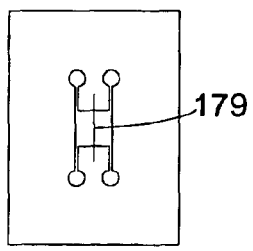
FIG._12D
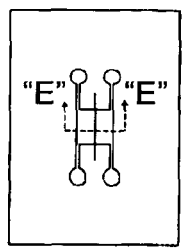
FIG._12E
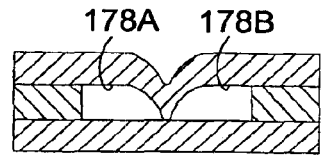
FIG._12F
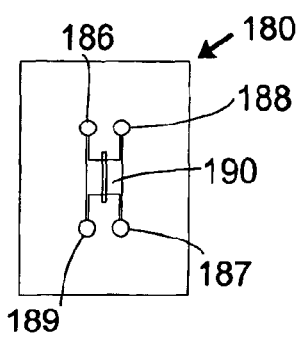
FIG._12G
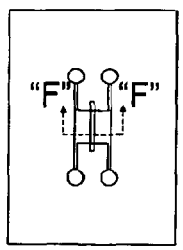
FIG._12H
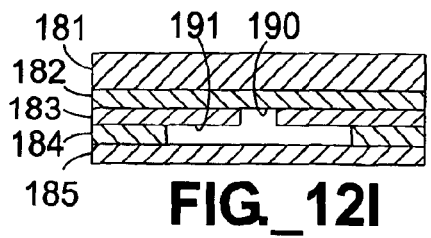
FIG._12I
FIG._12J

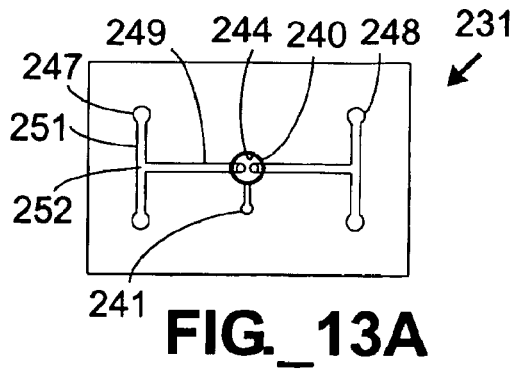
FIG._13A
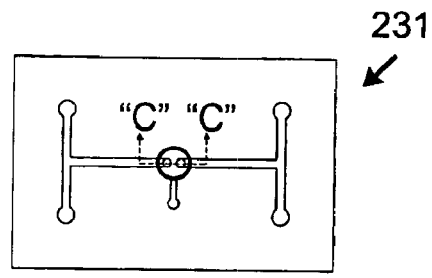
FIG._13B
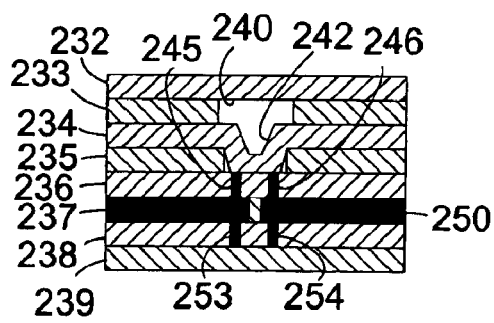
FIG._13C
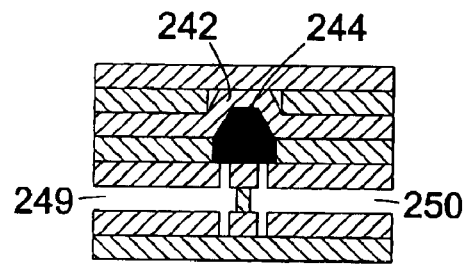
FIG._13D
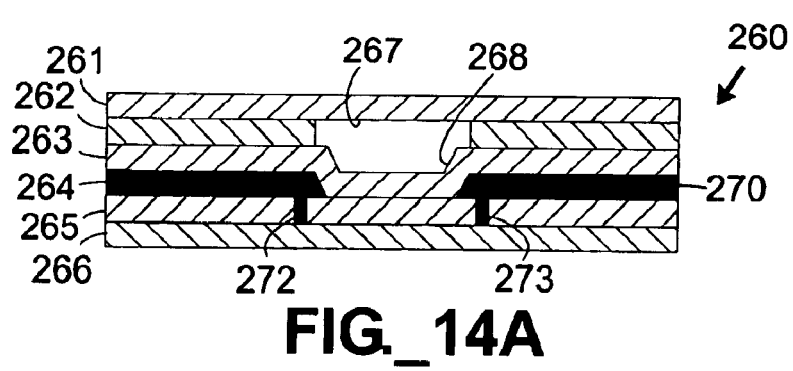
FIG._14A
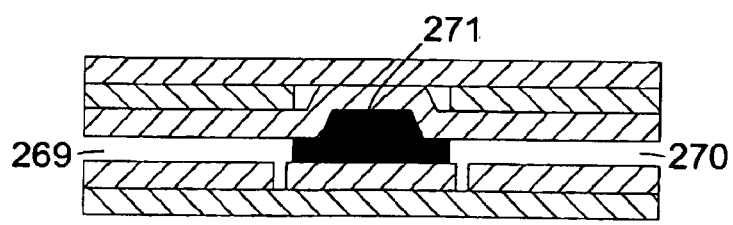
FIG._14B

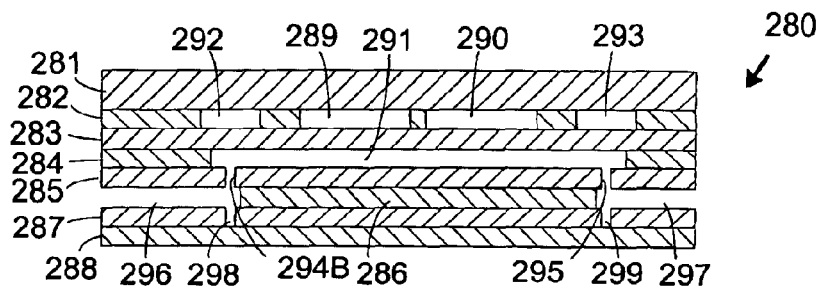
FIG._15A
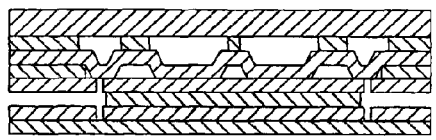
FIG._15B
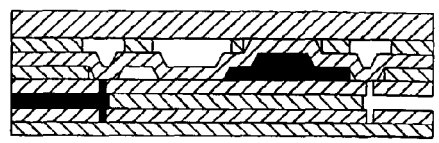
FIG._15E
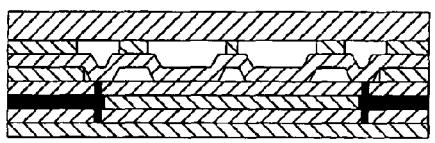
FIG._15C
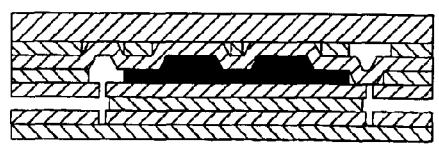
FIG._15F
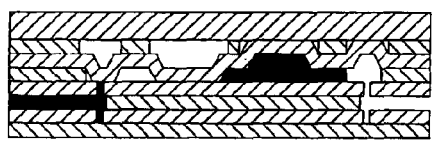
FIG._15D
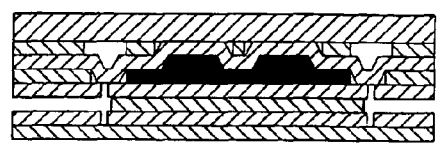
FIG._15G

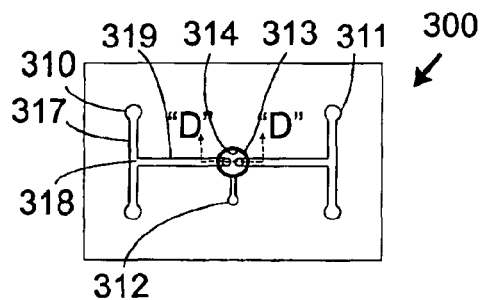
FIG._16A
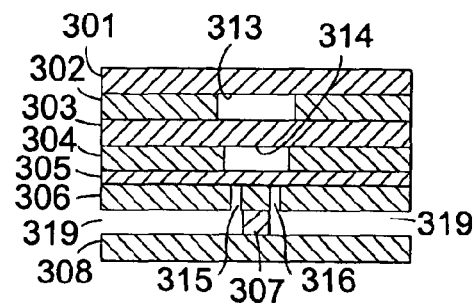
FIG._16B
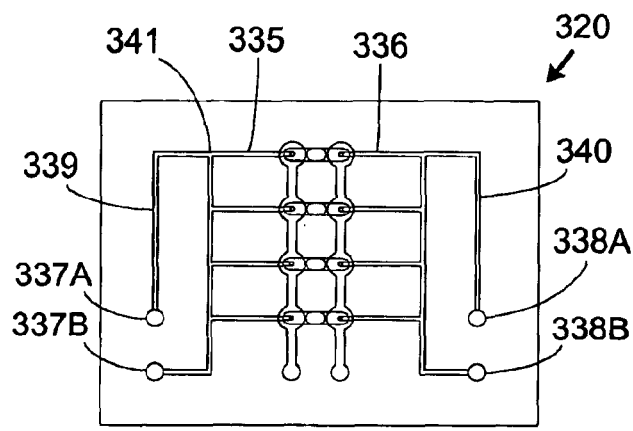
FIG._17A
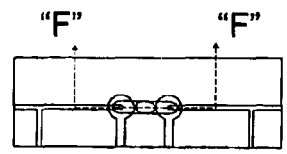
FIG._17B
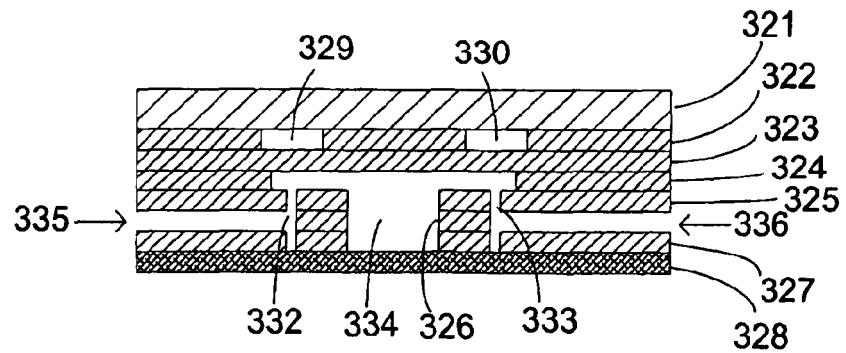
FIG._17C

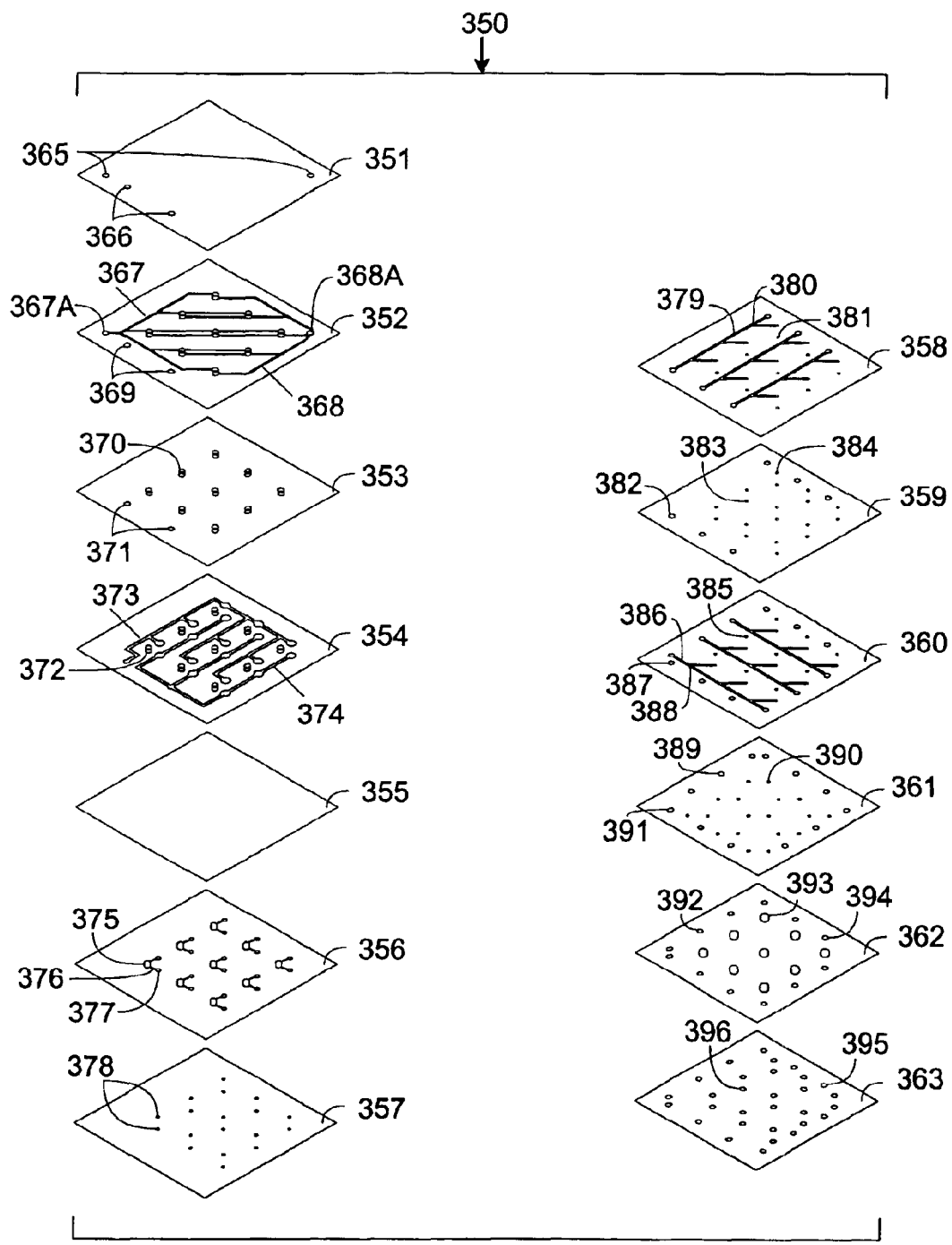
FIG._18A

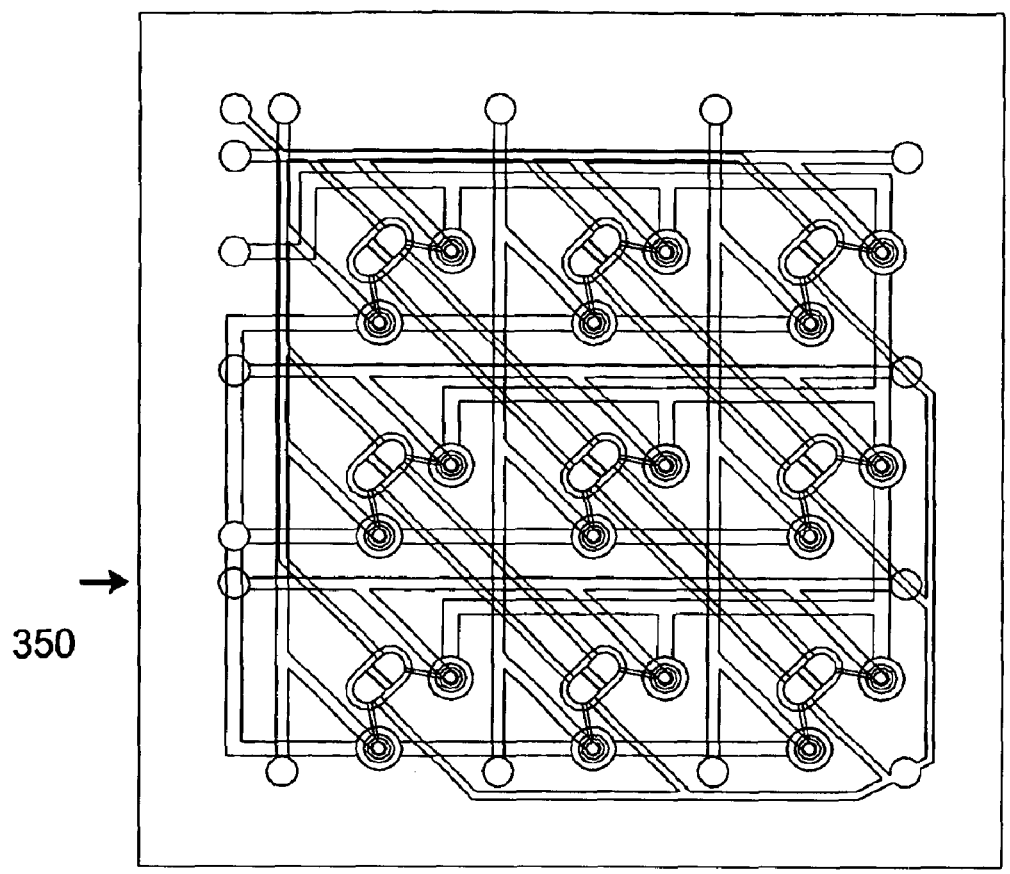
FIG._18B
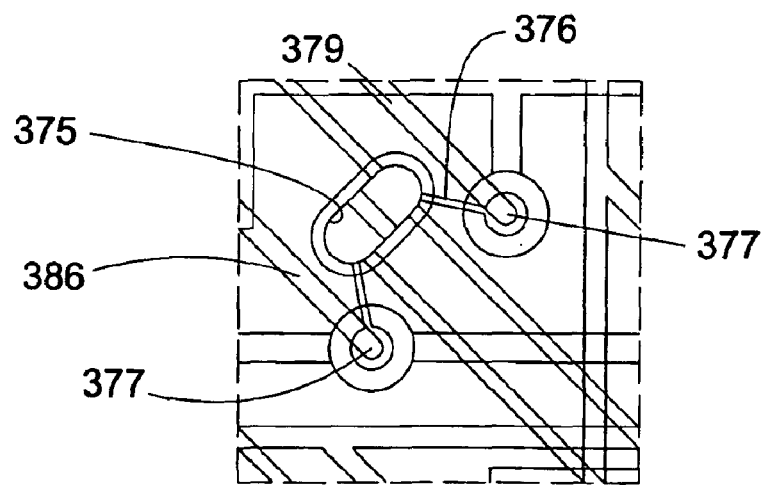
FIG._18C

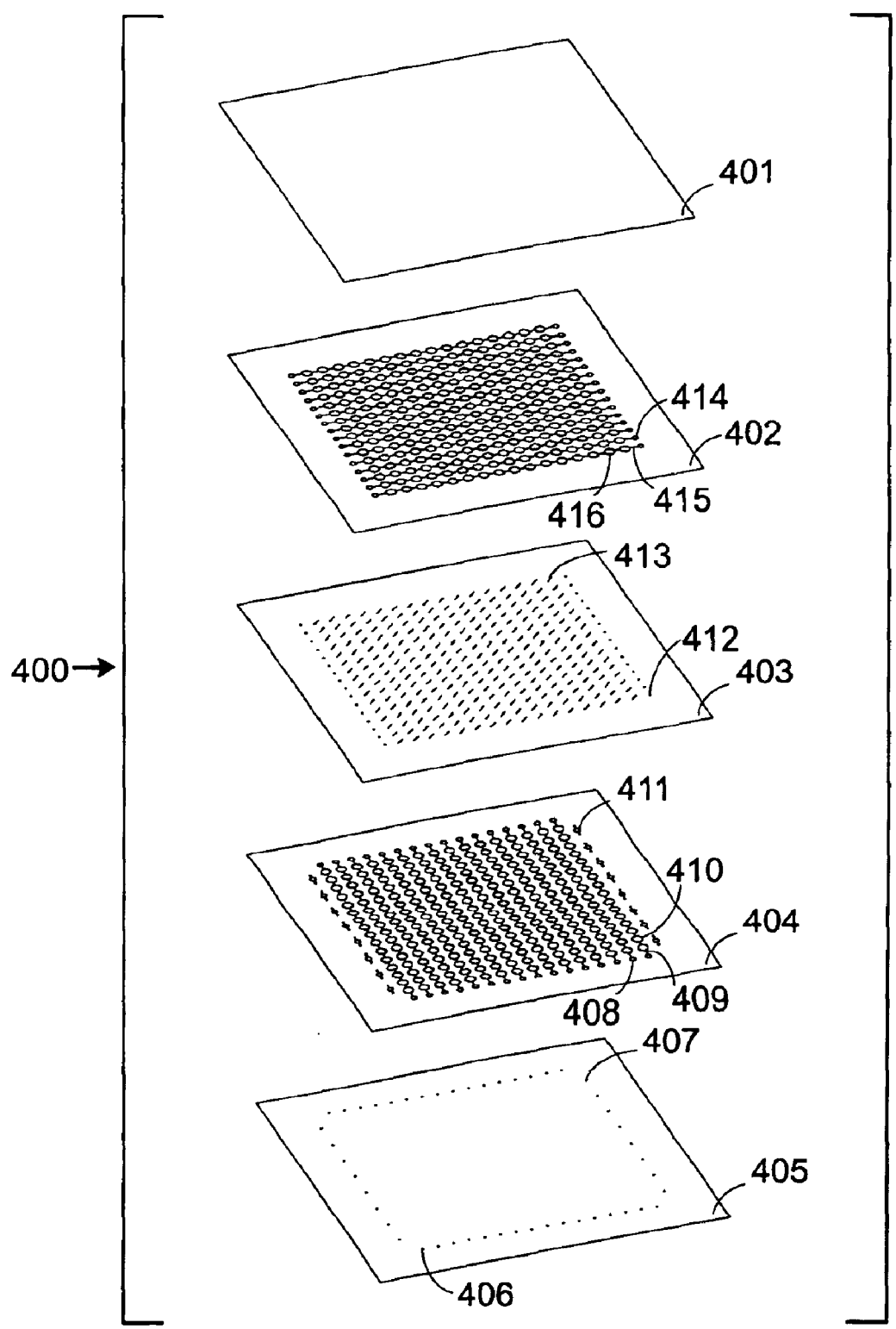
FIG._19A

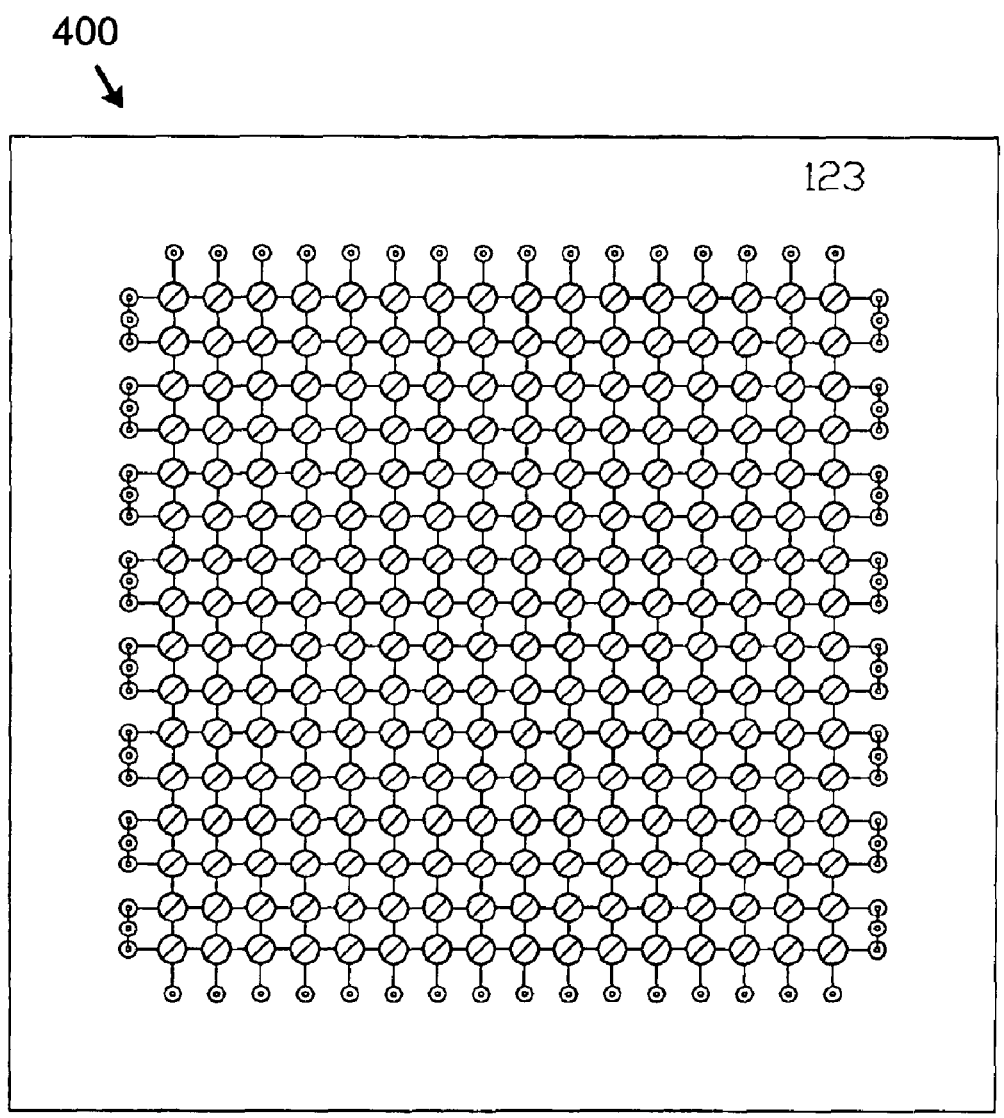
FIG._19B

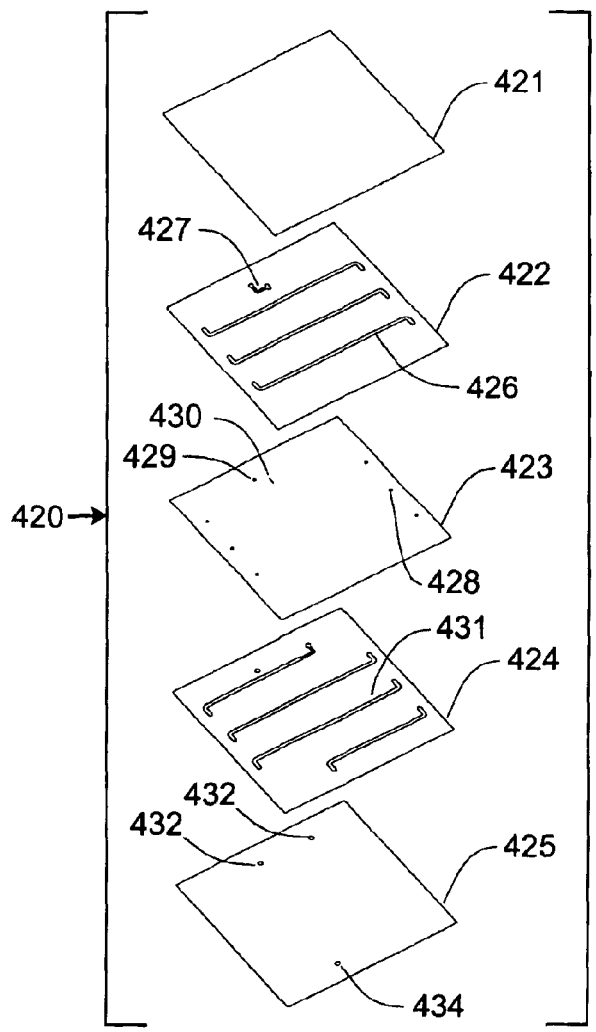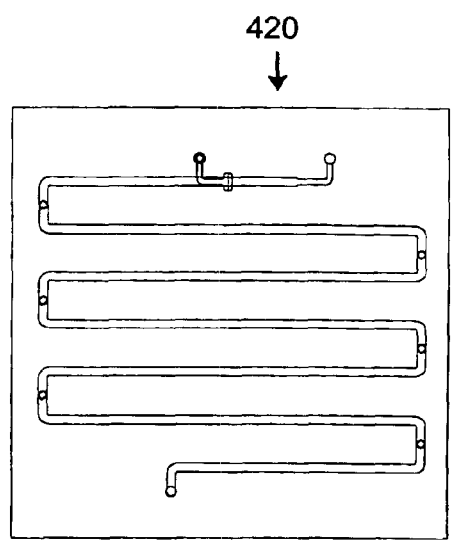
FIG._20A
FIG._20B

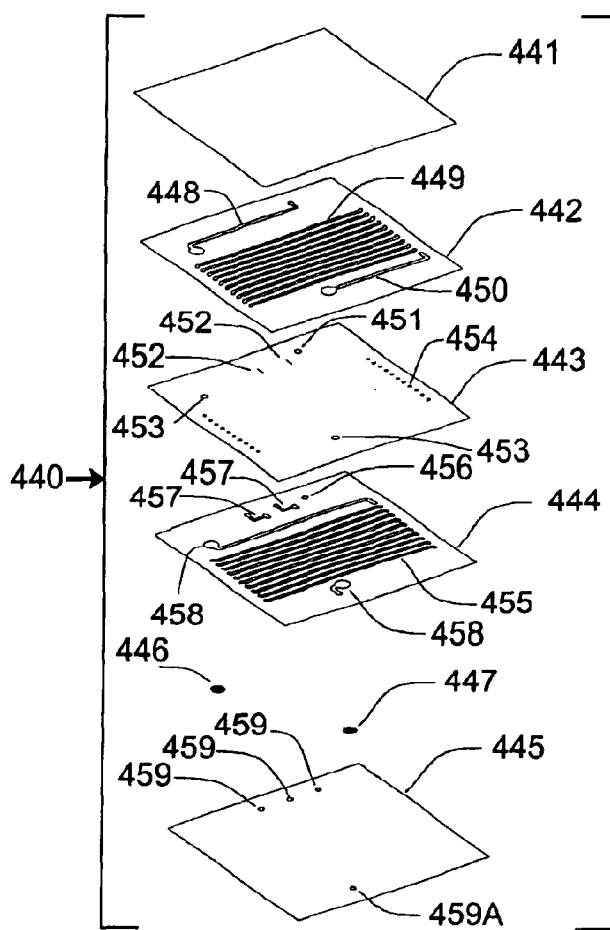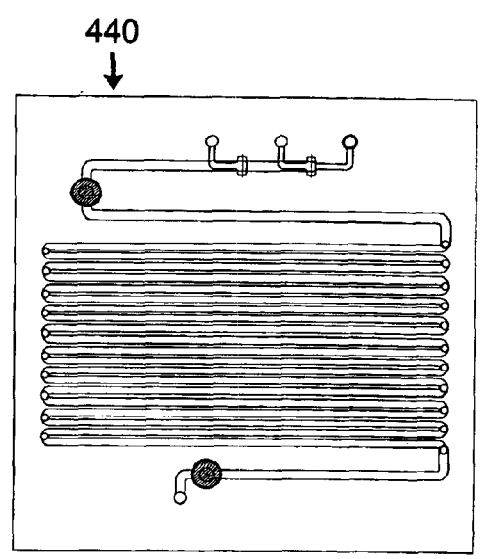
FIG._21B
FIG._21A

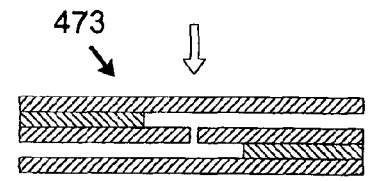
FIG._22C
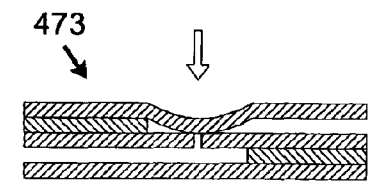
FIG._22D
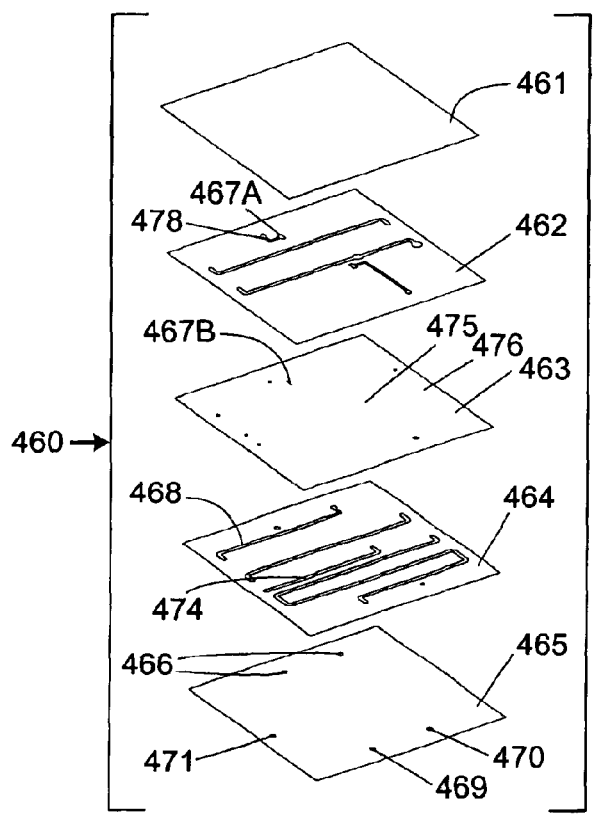
FIG._22A
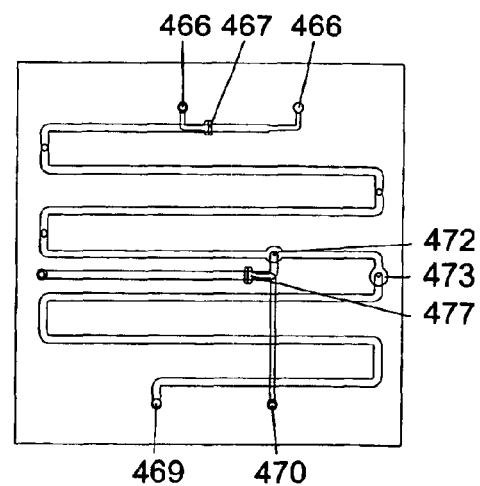
FIG._22B

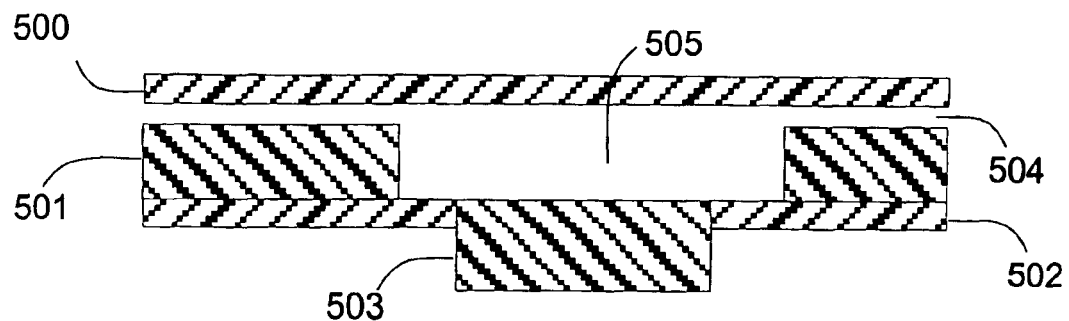
FIG._23A
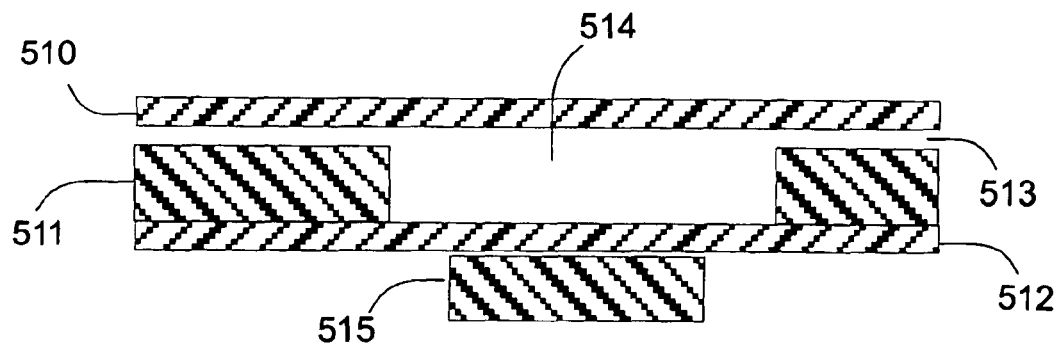
FIG._23B
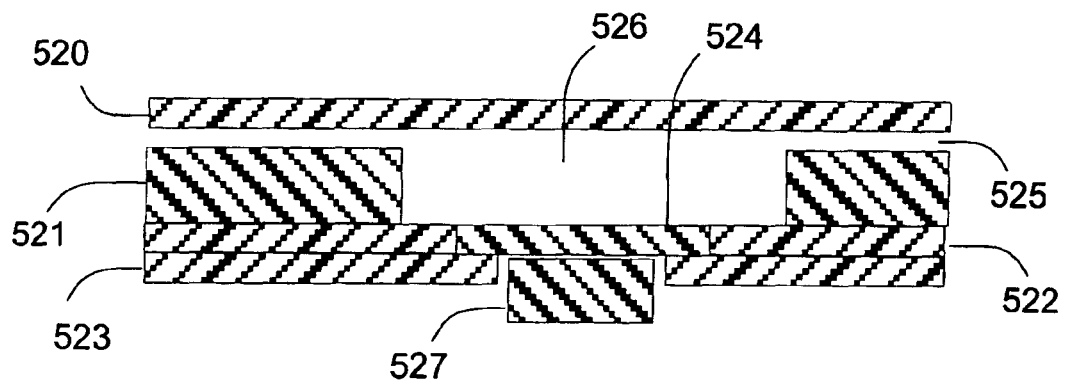
FIG._23C

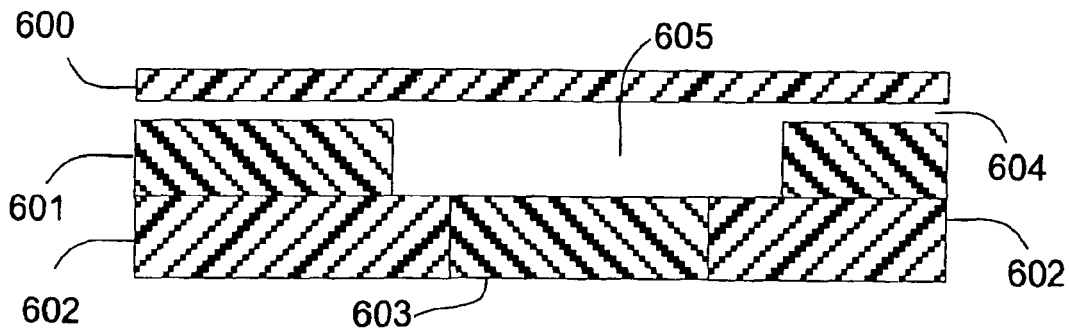
FIG._24A
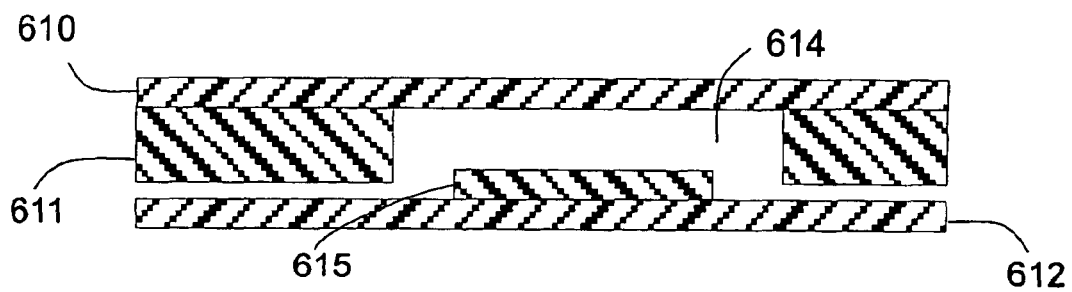
FIG._24B
FIG._24C
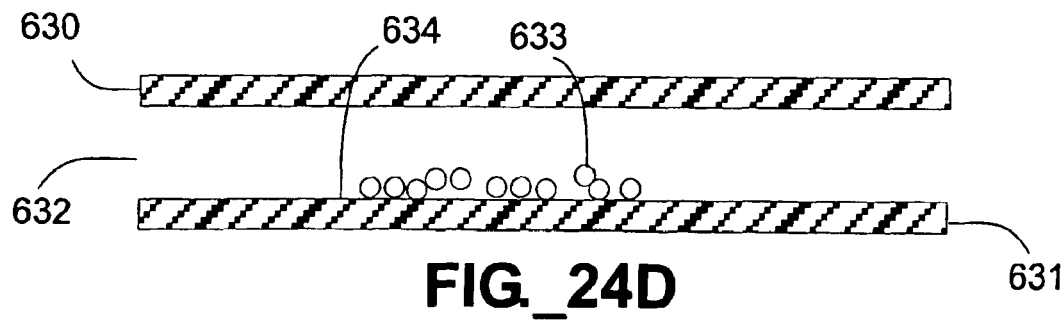
FIG._24D

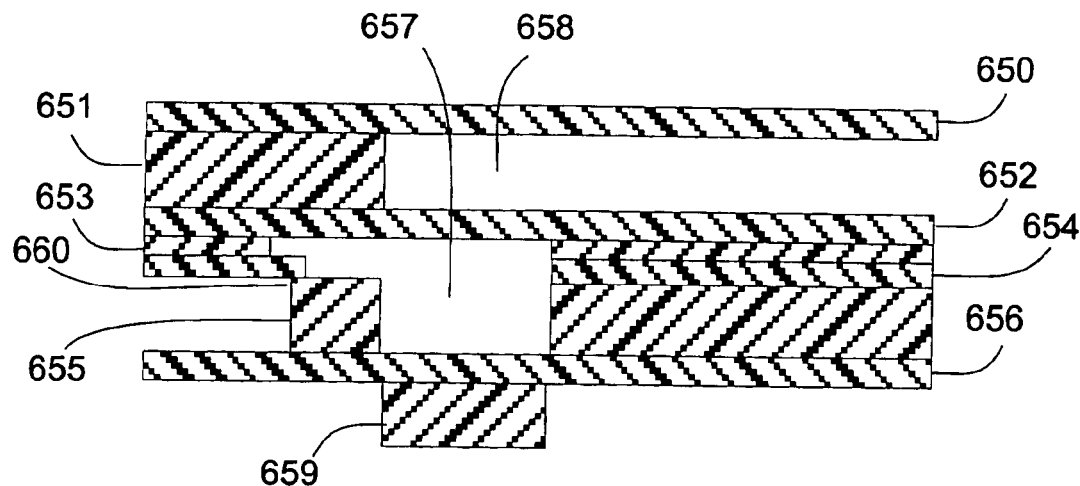
FIG._25A
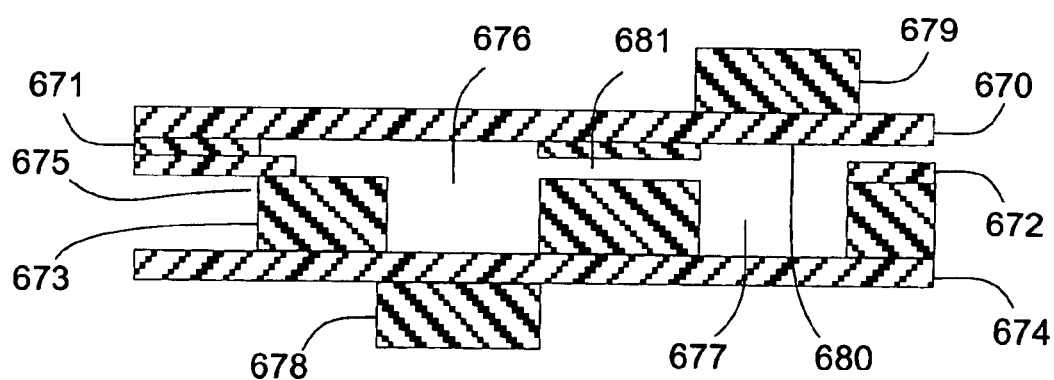
FIG._25B

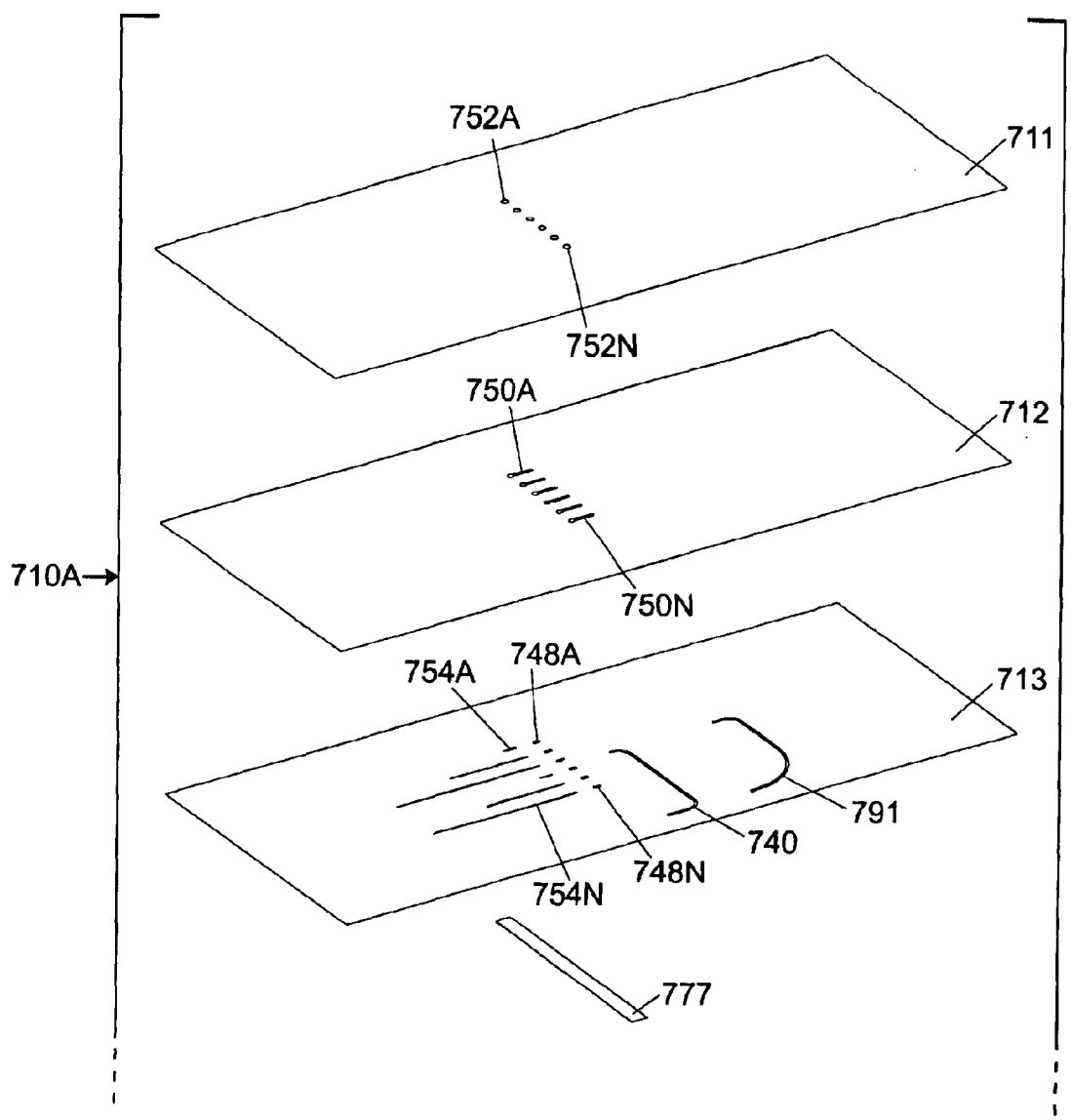
FIG._26A

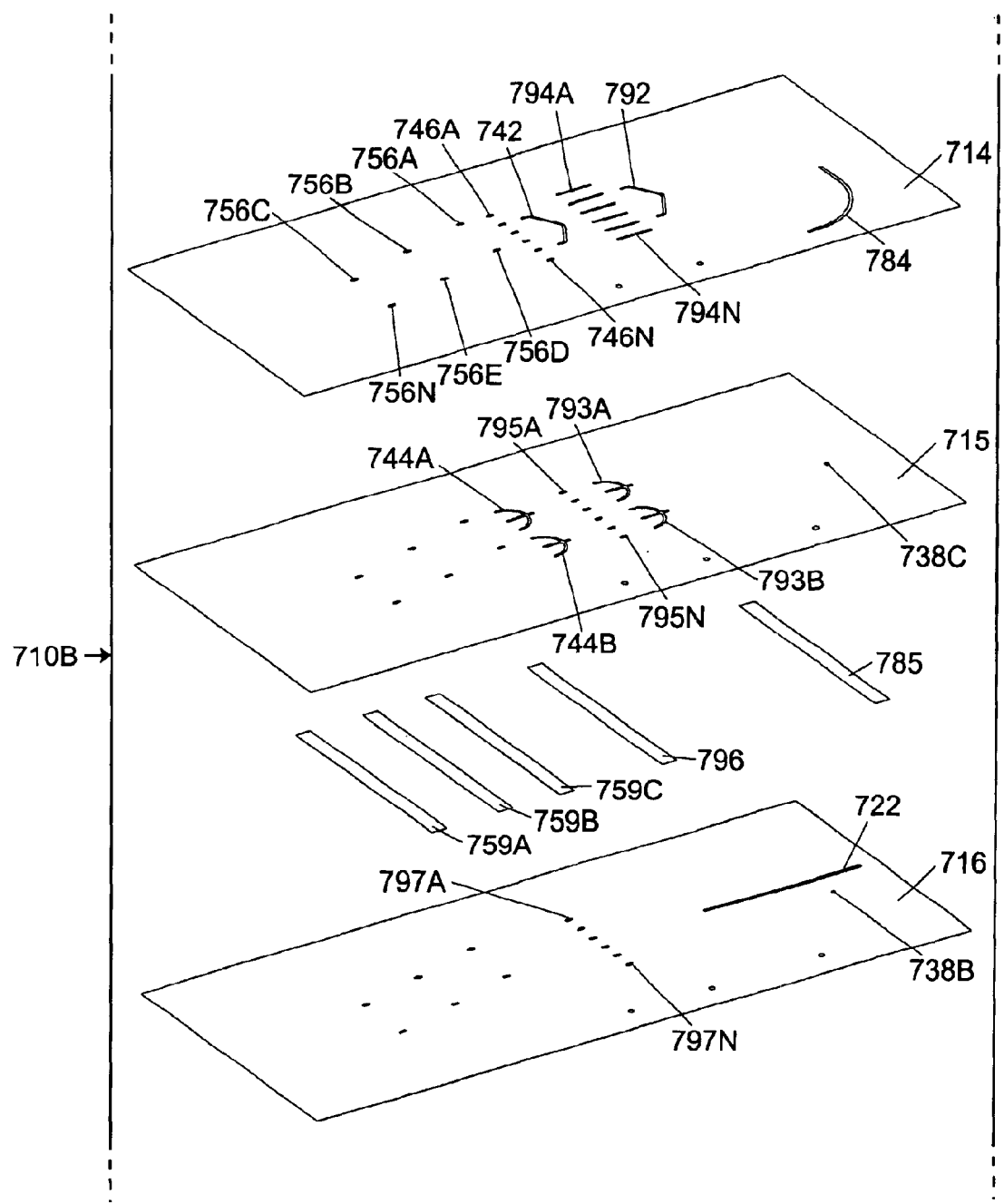
FIG._26B

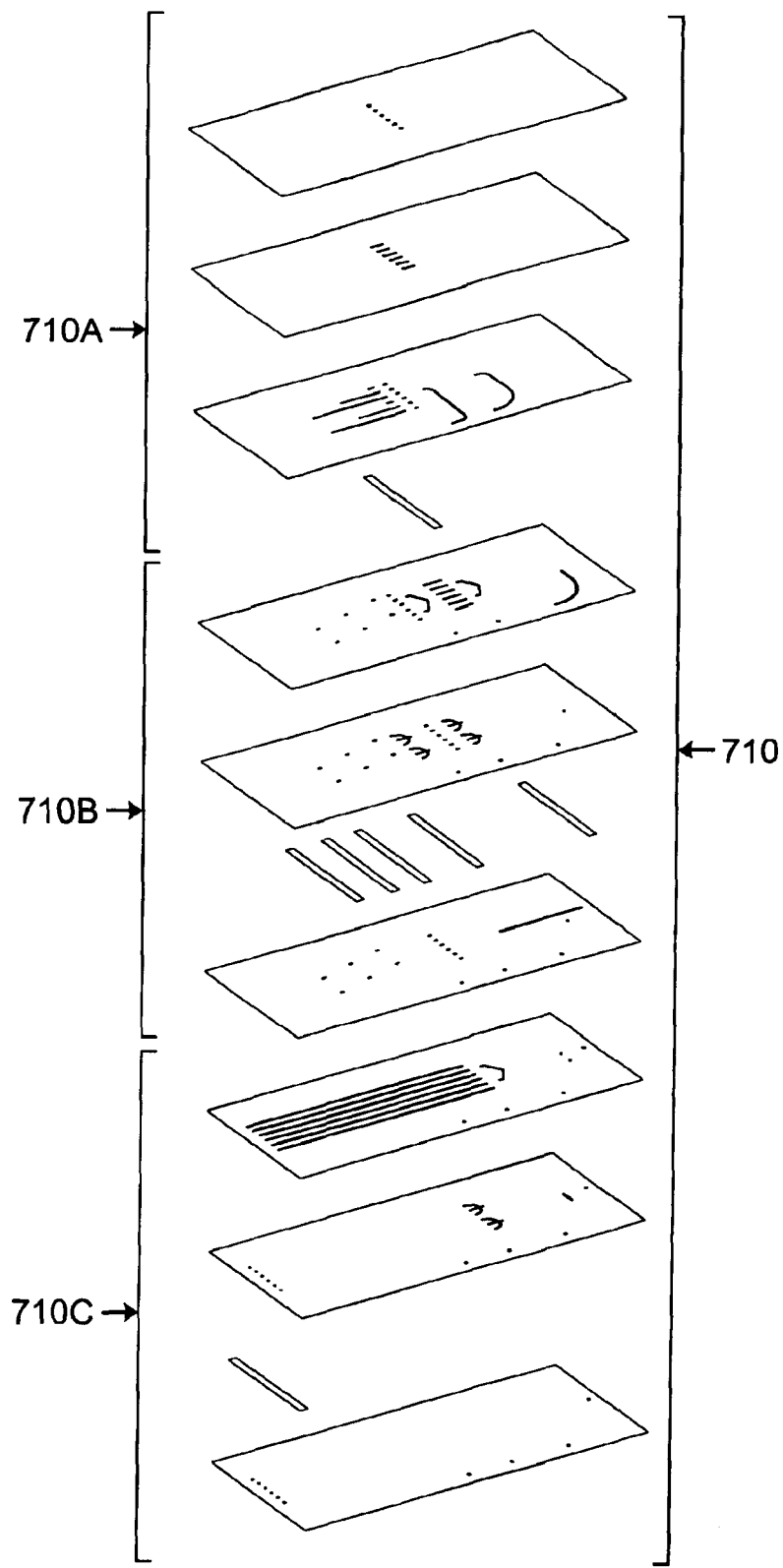
FIG._26D

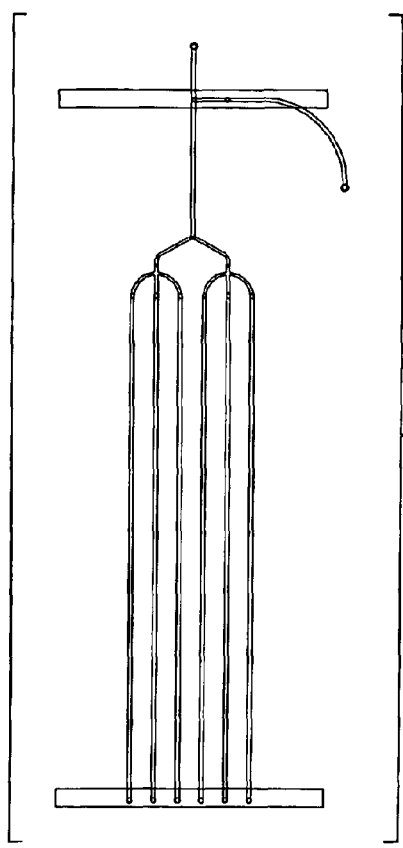
FIG._26F
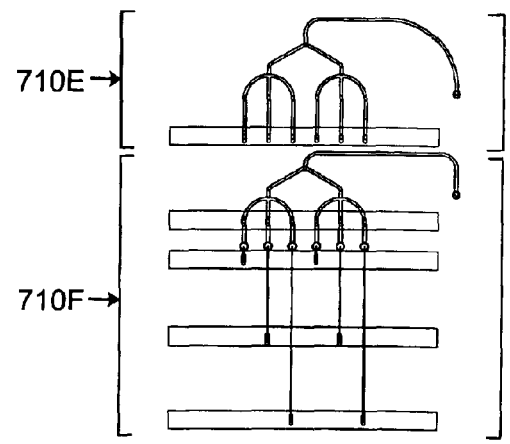
FIG._26G

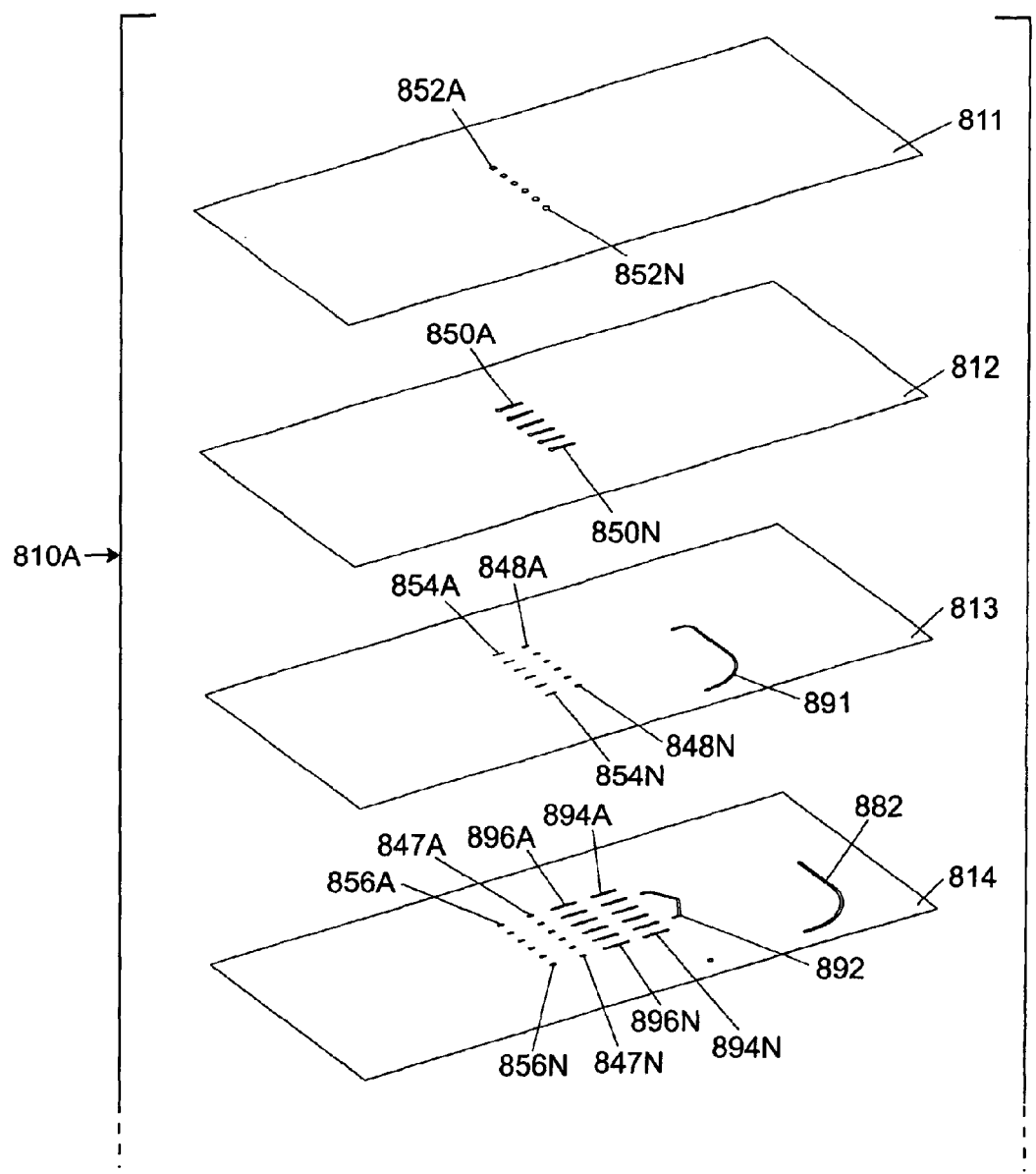
FIG._27A

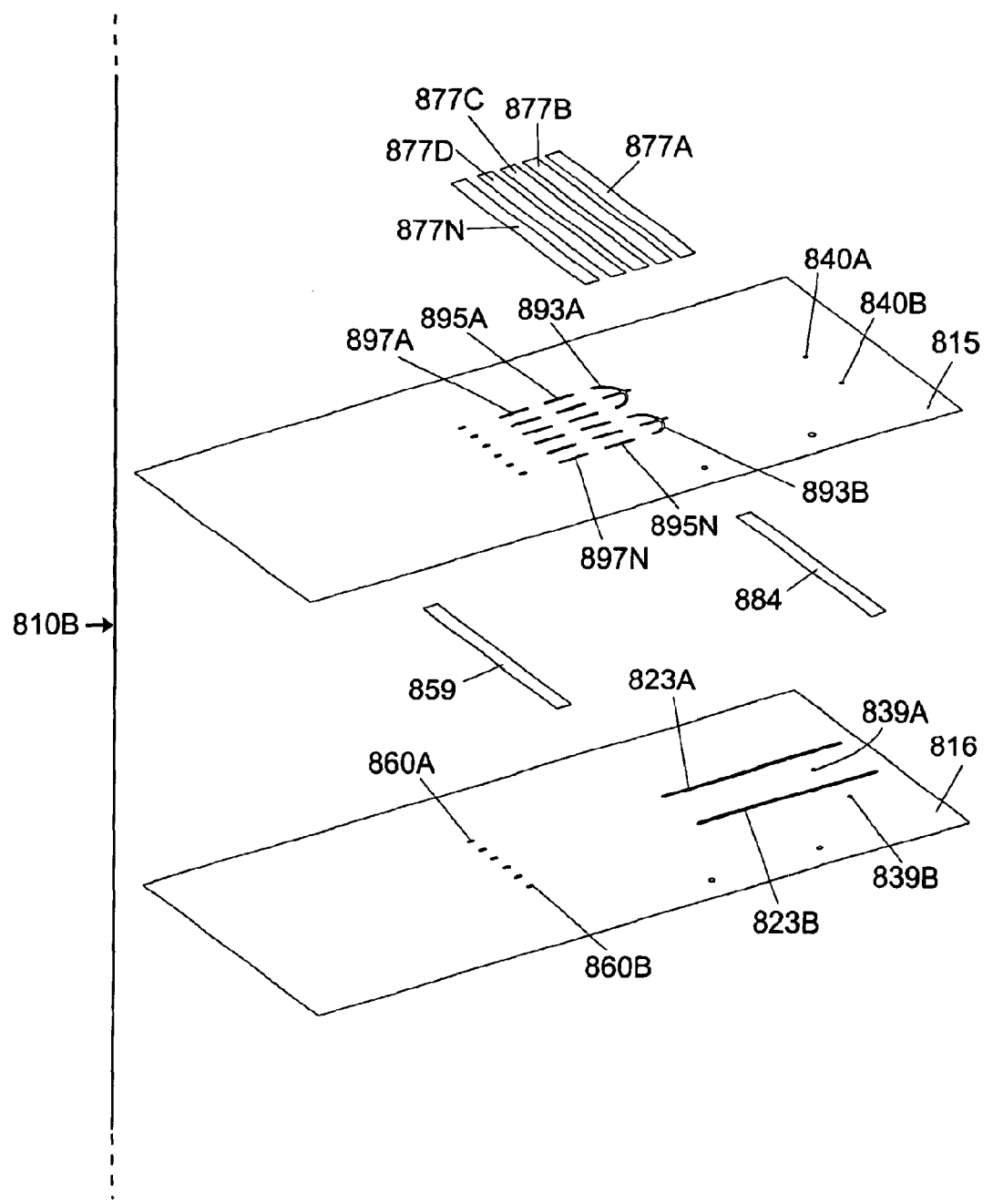
FIG._27B

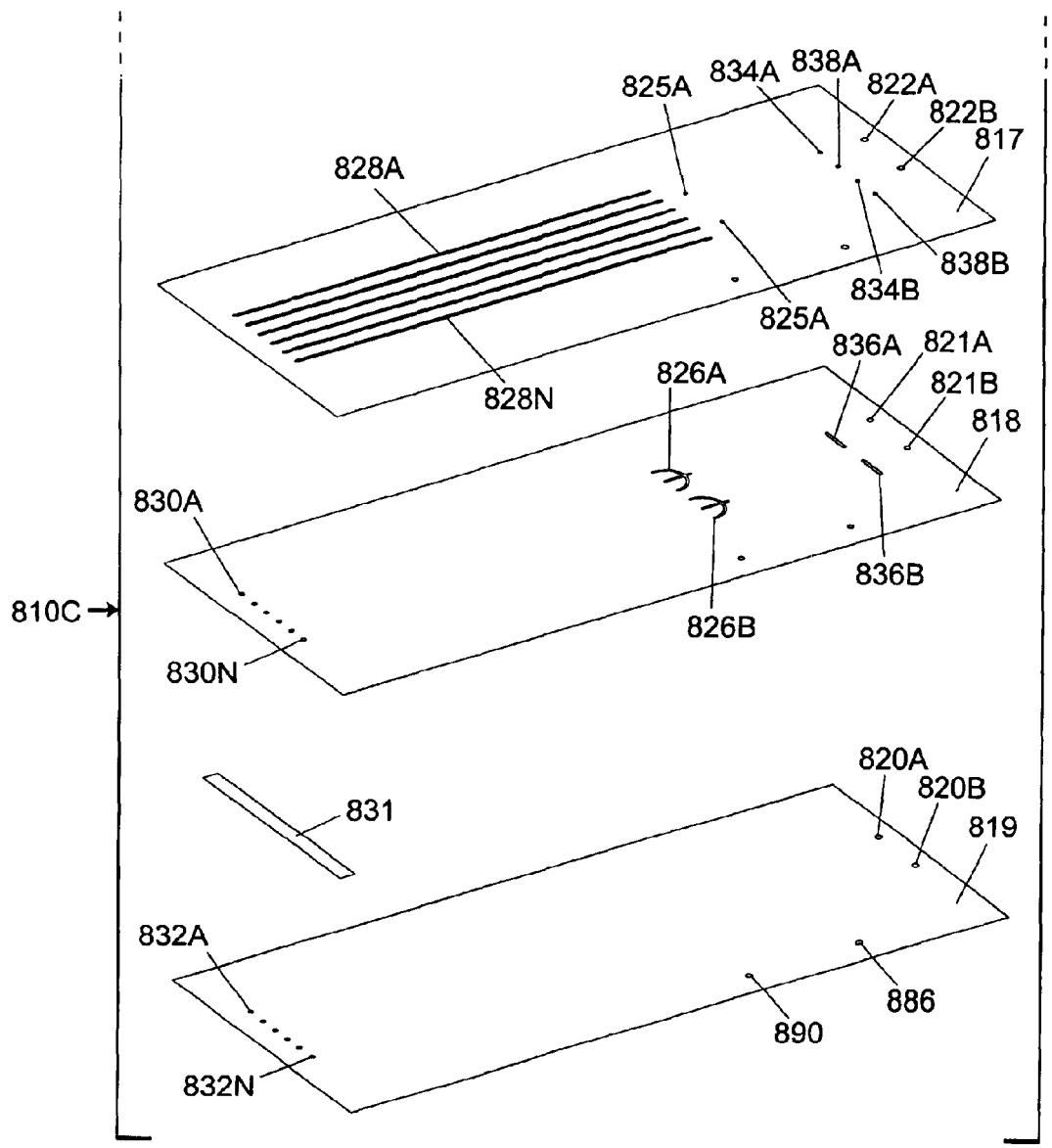
FIG._27C

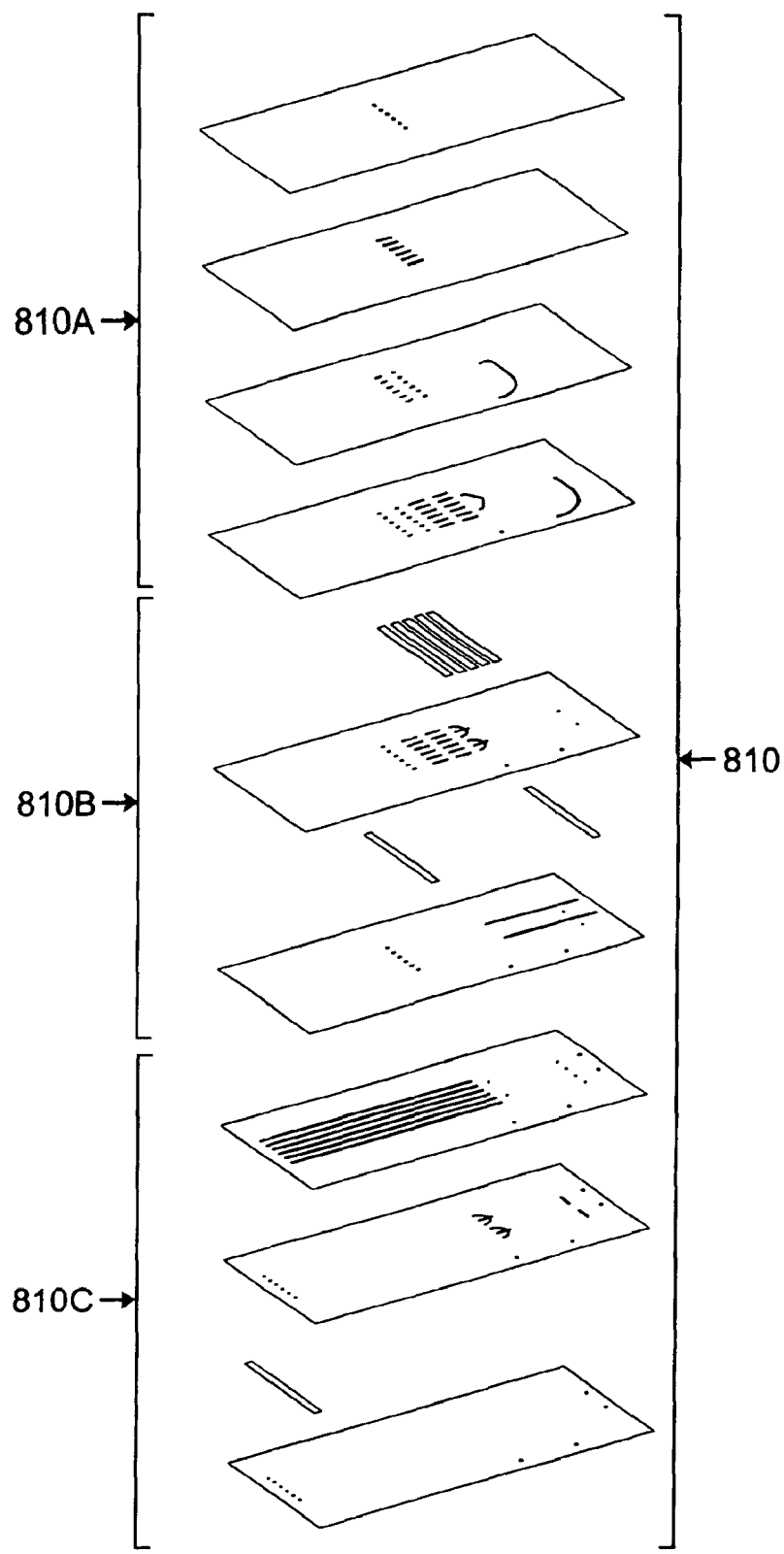
FIG._27D

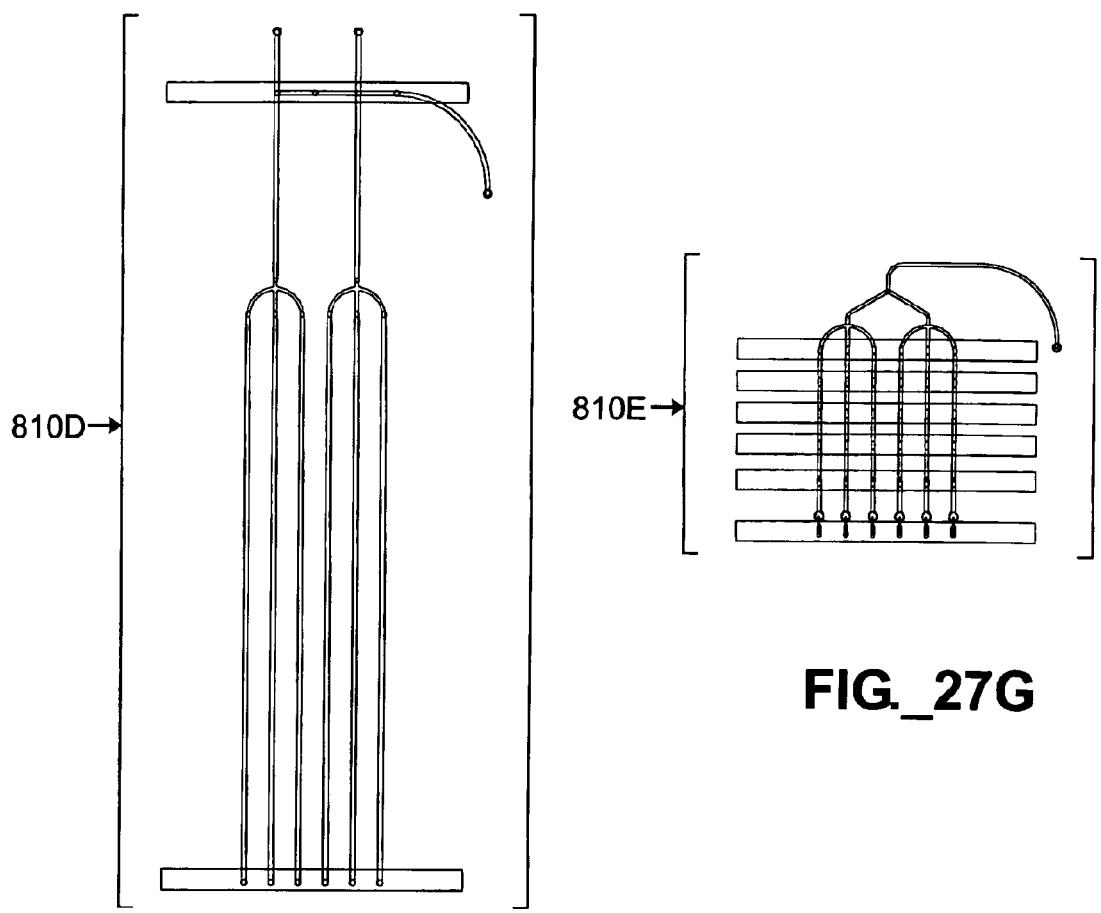
FIG._27G
FIG._27F

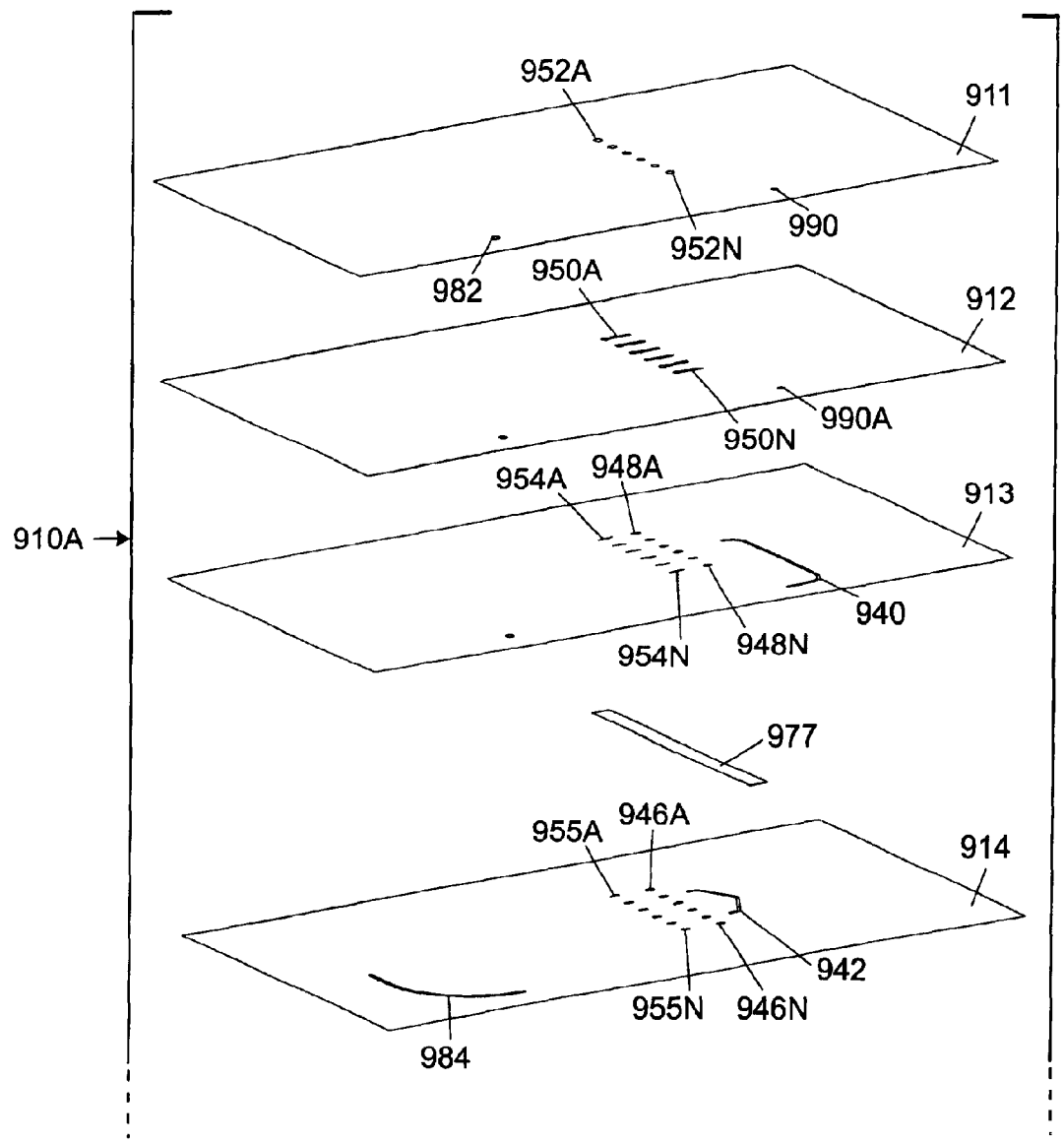
FIG._28A

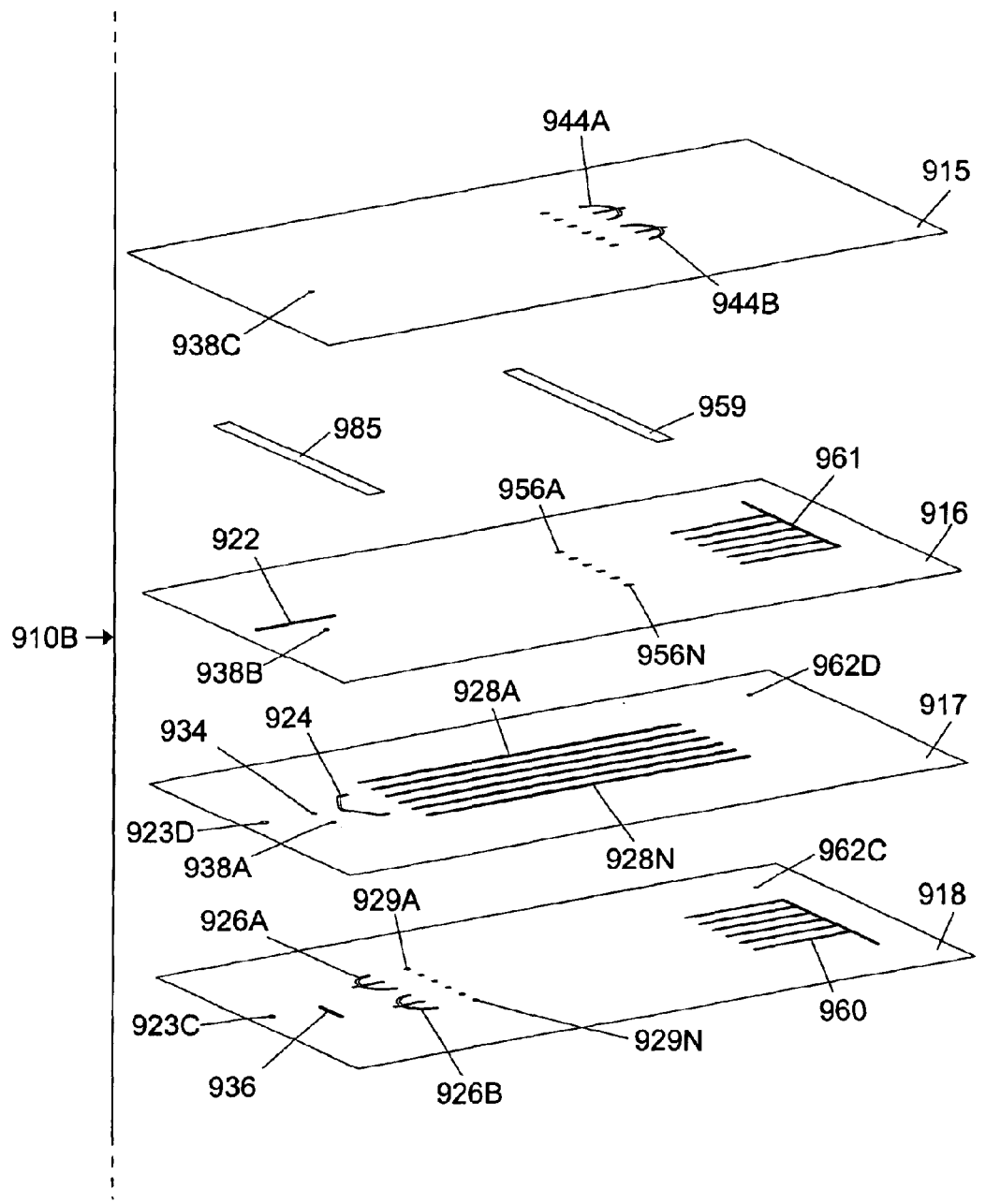
FIG._28B

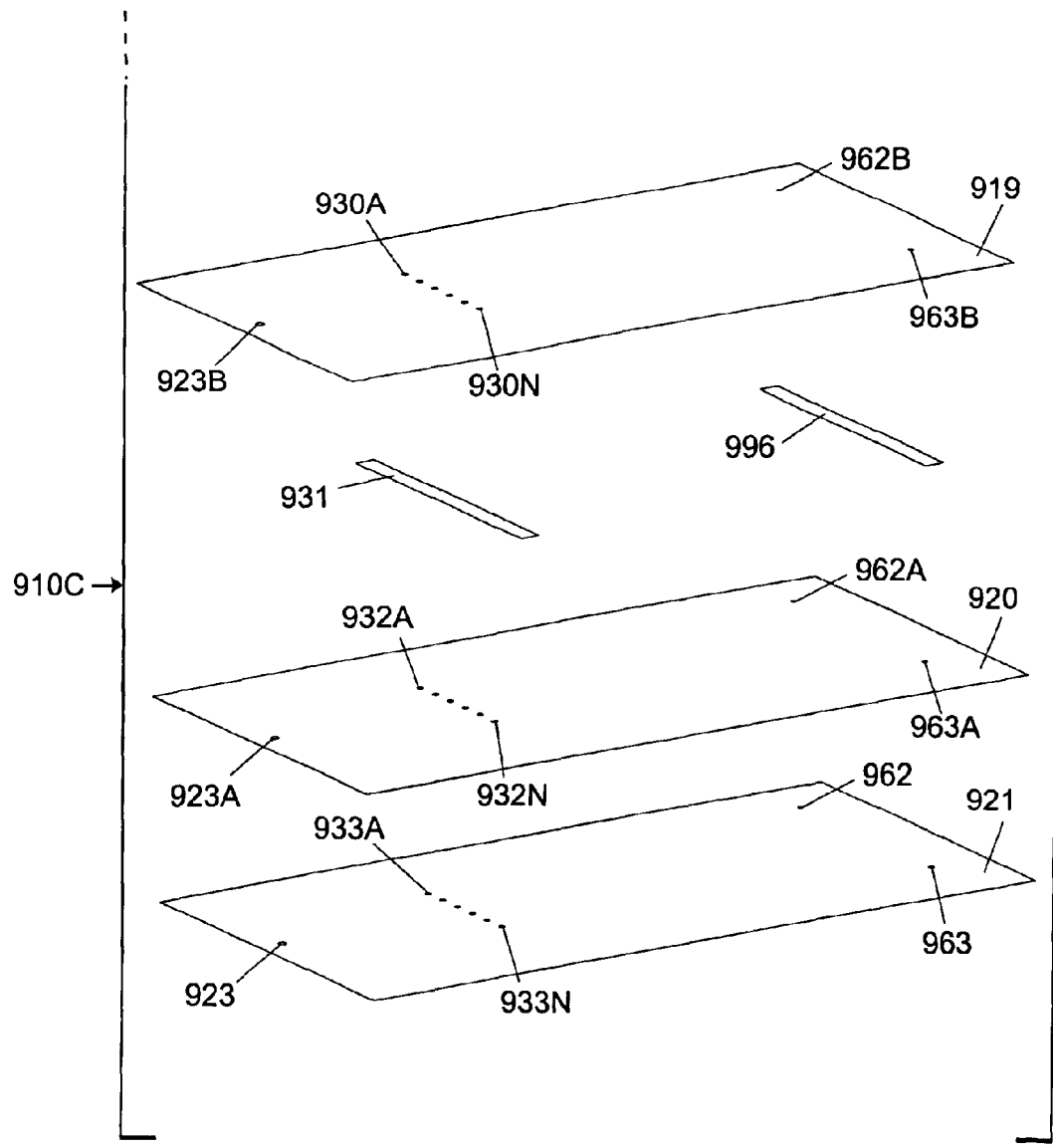
FIG._28C

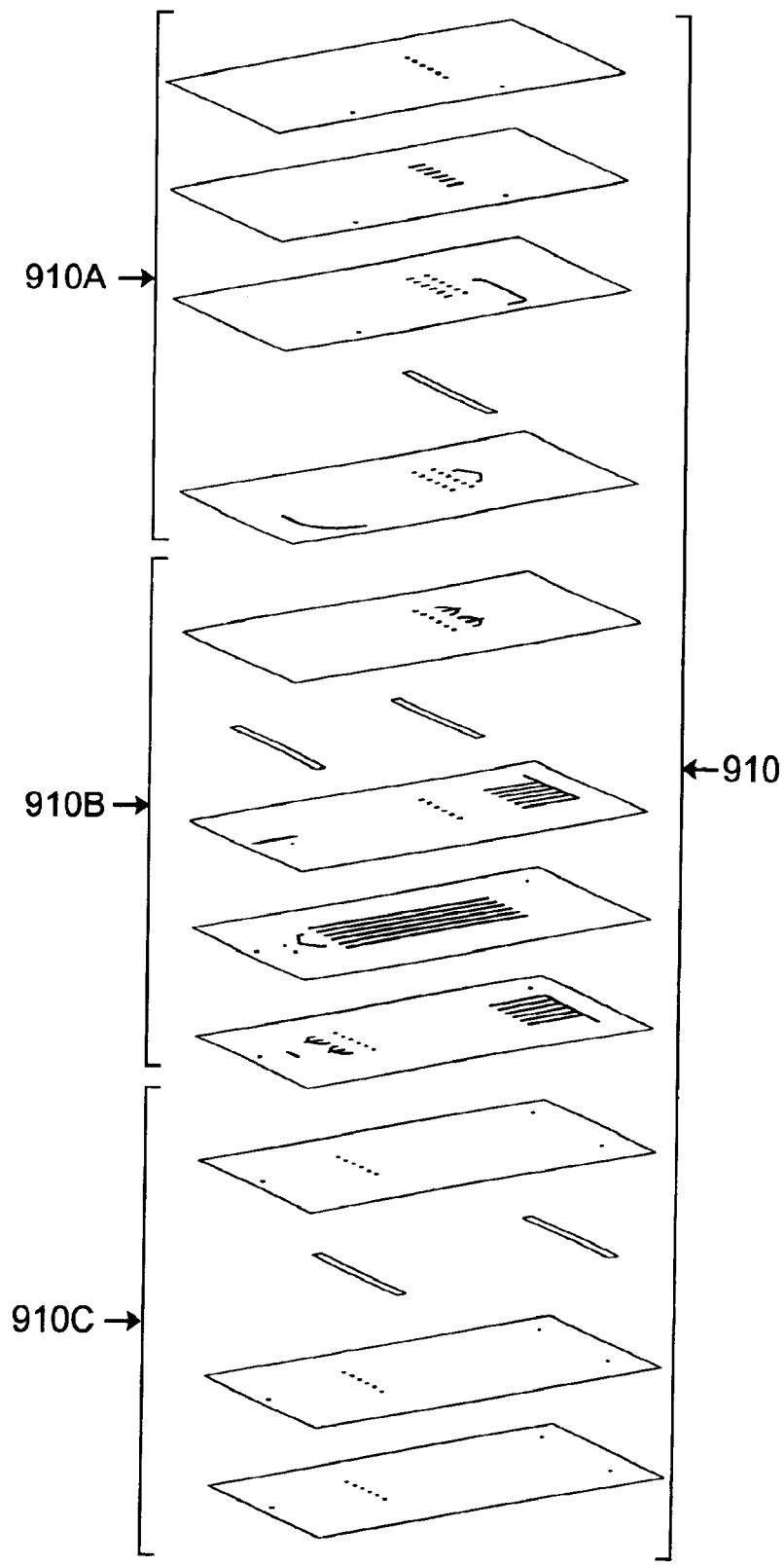
FIG._28D

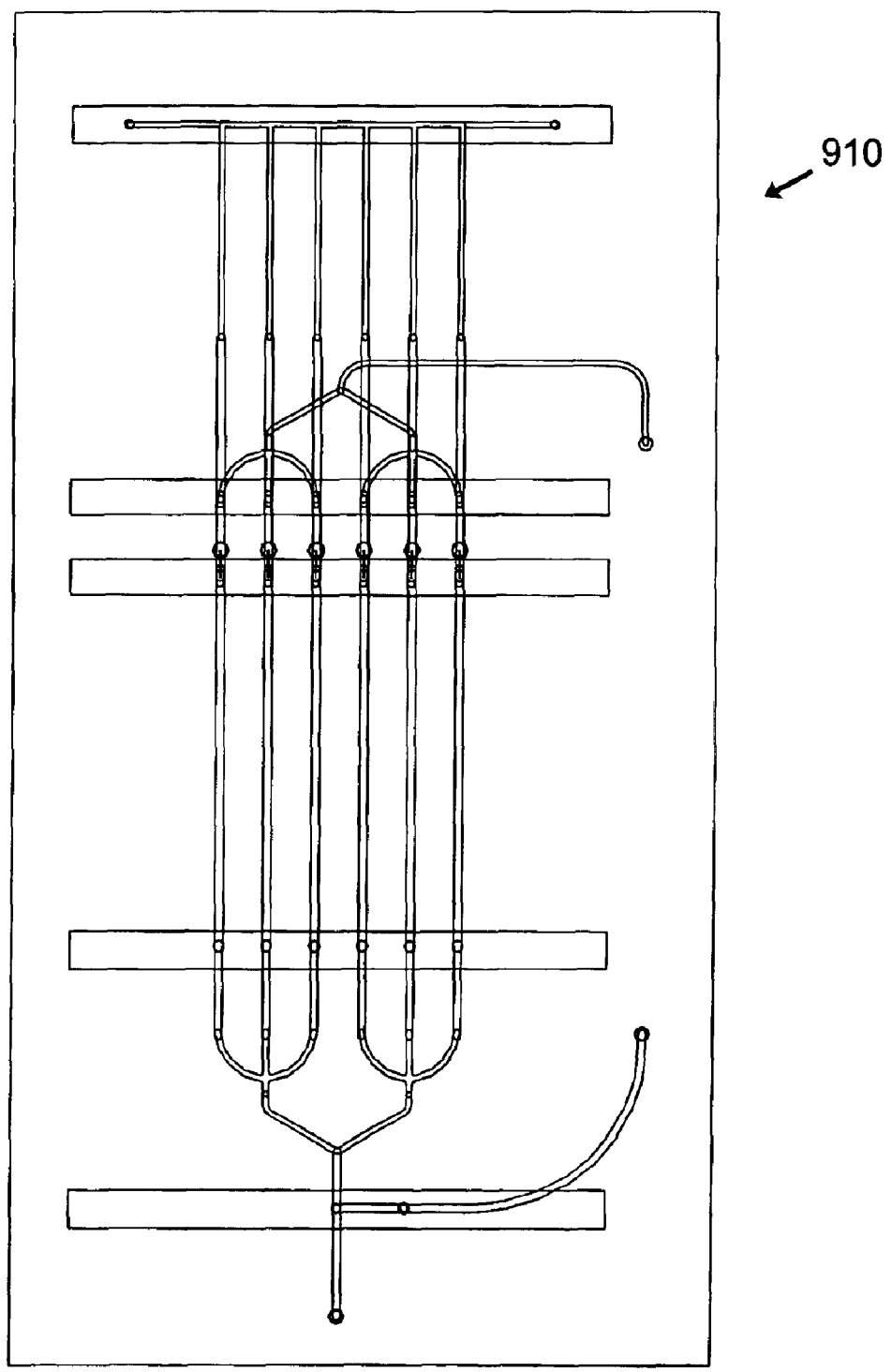
FIG._28E

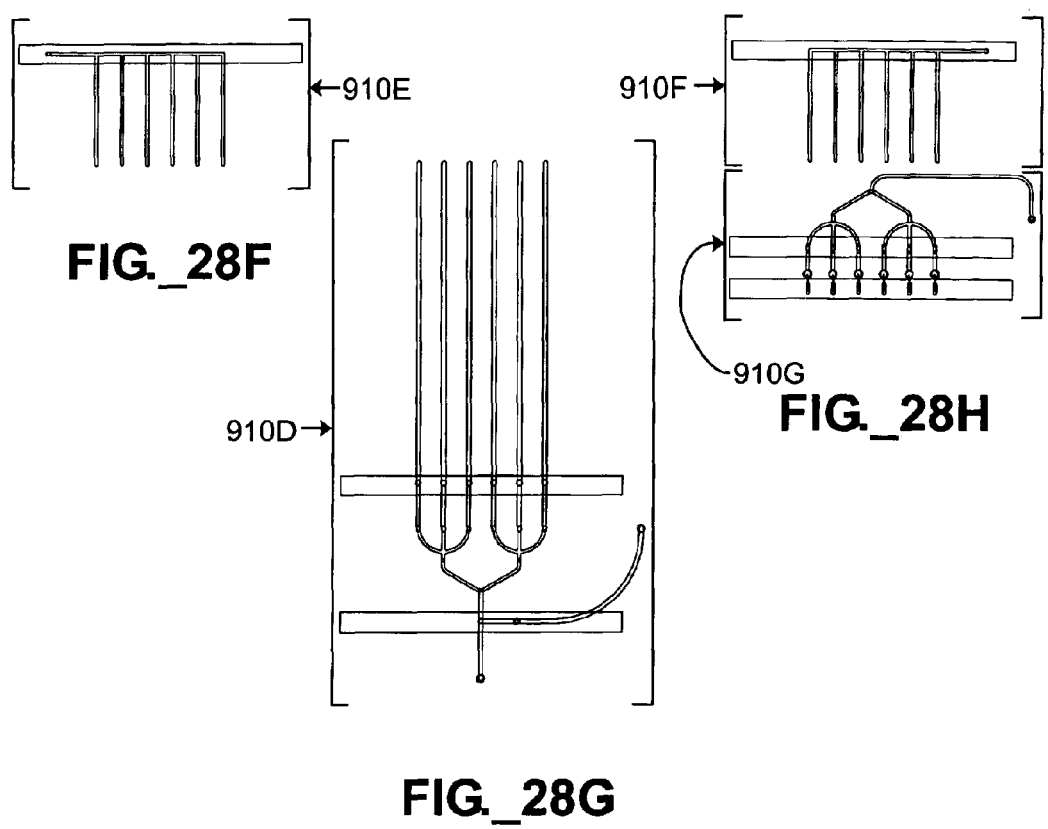
FIG._28F
FIG._28G
FIG._28H

MICROFLUIDIC DEVICES FOR METHODS DEVELOPMENT

STATEMENT OF RELATED APPLICATION(S)

This application claims priority to U.S. patent application Ser. No. 60/296,882, filed Jun. 7, 2001, and is a Continuation-In-Part of U.S. patent application Ser. No. 10/165,448 filed Jun. 7, 2002, now U.S. Pat. No. 6,729,352.

FIELD OF THE INVENTION

The present invention relates to devices that may be used to develop or optimize various analytical or synthesis operations, typically by subjecting similar samples or reagents to different process conditions in parallel.

BACKGROUND OF THE INVENTION

There has been a growing interest in the manufacture and use of microfluidic systems for the acquisition of chemical and biological information. In particular, when conducted in microfluidic volumes, complicated biochemical reactions may be carried out using very small volumes of liquid. Among other benefits, microfluidic systems are characterized by improved reaction response time, reduced sample volumes, and lower reagent consumption. When volatile or hazardous materials are used or generated, performing reactions in microfluidic volumes also enhances safety and reduces disposal quantities.

Traditionally, microfluidic devices have been constructed in a planar fashion using techniques that are borrowed from the silicon fabrication industry. Representative systems are described, for example, in some early work by Manz et al. (Trends in Anal. Chem. (1990) 10(5): 144–149; Advances in Chromatography (1993) 33: 1–66). In these publications, microfluidic devices are constructed by using photolithography to define channels on silicon or glass substrates and etching techniques to remove material from the substrate to form the channels. A cover plate is bonded to the top of the device to provide closure. Miniature pumps and valves can also be constructed to be integral (e.g., within) such devices. Alternatively, separate or off-line pumping mechanisms are contemplated.

More recently, a number of fabrication methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., Analytical Chemistry (1998) 70: 4974–4984; McCormick et. al., Analytical Chemistry (1997) 69: 2626–2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., Journal of Micromechanical Microengineering (1994) 4: 186–191), and commercialized by Micro-Parts (Dortmund, Germany). Jenoptik (Jena, Germany) also uses LIGA and a hot-embossing technique. Imprinting methods in PMMA have also been demonstrated (see, Martynova et al., Analytical Chemistry (1997) 69: 4783–4789). These techniques, however, do not lend themselves to rapid prototyping and manufacturing flexibility. Moreover, the tool-up costs for both of these techniques are quite high and can be cost-prohibitive.

Laboratory processes including synthesis and analysis are characterized by numerous variables capable of affecting the results of the particular process. Considerable resources—in terms of labor, materials, equipment, and time—are expended in developing and optimizing new synthetic and analytical processes. Typically, a first experiment is performed according to a first set of process conditions, followed by performance of a another experiment with a slightly modified set of process conditions, followed by a performance of subsequent experiment(s) with further modified process conditions.

It would be desirable to reduce the expenditure of resources to develop and optimize new processes. In particular, it would be desirable to provide devices capable of subjecting similar samples or reagents to different process conditions in parallel. Ideally, such devices would utilize one or more common inputs from external devices such as pumps to minimize equipment cost. Additionally, such devices would be substantially non-reactive in the presence of various chemicals and substances, capable of withstanding elevated operating pressures, and economical to fabricate in small or large quantities.

BRIEF DESCRIPTION OF THE DRAWINGS

FIG. 1A is an exploded perspective view of a microfluidic device fabricated with a stencil layer.

FIG. 1B is a top view of the assembled device of FIG. 1A.

FIG. 2A is an exploded perspective view of a microfluidic coupler fabricated with a stencil layer.

FIG. 2B is a top view of the assembled device of FIG. 2A.

FIG. 2C is an exploded perspective view of a microfluidic coupler fabricated with a stencil layer and including a semi-permeable membrane.

FIG. 2D is a top view of the assembled device of FIG. 2C.

FIGS. 3A–3F are schematic views illustrating six different configurations of a modular microfluidic system for performing a sequence of operations on a fluid with three microfluidic modules, with the modules being connected with multiple microfluidic coupling devices.

FIGS. 4A–4E are side cross-sectional views of the build-up of a microfluidic device fabricated with a coating or sealing layer.

FIG. 5A is an exploded perspective view of microfluidic device having an internal filter element.

FIG. 5B is a top view of the device of FIG. 5A.

FIG. 5C is a side cross-sectional view of a portion of the device of FIGS. 5A–5B taken along section line "A"—"A" as provided in FIG. 5B.

FIG. 6A is an exploded perspective view of a five-layer microfluidic device capable of dividing and metering a fluid sample.

FIG. 6B is a top view of the assembled device of FIG. 6A.

FIG. 7A is an exploded perspective view of a five-layer microfluidic device capable of delivering a relatively constant flow rate of fluid over a large range of pressures.

FIG. 7B is a top view of the assembled device of FIG. 7A.

FIG. 7C is a cross-sectional view of a portion of the microfluidic device of FIGS. 7A–7B with the regulatory region in the open position.

FIG. 7D provides the same cross-sectional view as FIG. 7C, but with the regulatory region in the closed position.

FIG. 7E is a cross-sectional view of an alternate embodiment of the device of FIGS. 7A–7B that includes a separate control channel for regulating fluid flow with the regulatory region in the open position.

FIG. 7F provides the same cross-sectional view as FIG. 7E, but with the regulatory region in the closed position.

FIG. 8A is an exploded perspective view of a five-layer microfluidic mixing device.

FIG. 8B is a top view of the assembled device of FIG. 8A.

FIG. 9A is an exploded perspective view of a five-layer microfluidic mixing device.

FIG. 9B is a top view of the device of FIG. 9A.

FIG. 10A is a top view of a microfluidic device capable of metering discrete amounts of two fluids in subchambers disposed in different layers, and then combining the contents of the subchambers to yield one fluidic combination.

FIG. 10B is an expanded top view of a central portion of the device of FIG. 1A.

FIG. 10C is a cross-sectional view of a portion of the device of FIG. 10A along section lines "B"—"B" shown in FIG. 10B.

FIG. 11A is an exploded perspective view of a five-layer microfluidic device capable of combining discrete amounts of up to four fluids to yield up to four fluidic combinations.

FIG. 11B is a top view of the assembled device of FIG. 11A.

FIG. 12A is a top view of a three-layer microfluidic device capable of metering discrete amounts of two fluids in subchambers disposed in the same layer, and then combining the contents of the subchambers to yield one fluidic combination.

FIG. 12B is a top view of the device of FIG. 12A illustrating section lines "E"—"E".

FIG. 12C is a cross-sectional view of a portion of the device of FIGS. 12A–12B along section lines "E"—"E".

FIG. 12D is a top view of the device of FIGS. 12A–12B following a laser heating step to partition the central chamber into two subchambers.

FIG. 12E is a top view of the device of FIG. 12D illustrating section lines "E"—"E".

FIG. 12F is a cross-sectional view of a portion of the device of FIG. 12E along section lines "E"—"E".

FIG. 12G is a top view of a five-layer microfluidic device capable of metering discrete amounts of two fluids in subchambers disposed in the same layer, and then combining the contents of the subchambers to yield one fluid combination.

FIG. 12H is a top view of the device of FIG. 12G, illustrating section lines "D"—"D".

FIG. 12I is a cross-sectional view of a portion of the device of FIGS. 12G–12H along section lines "F"—"F", the device having one unpartitioned chamber.

FIG. 12J provides the same view as FIG. 12I, except that the device chamber is partitioned by deflection of a portion of the lower deformable layer to contact an adhesive surface in a central device layer.

FIG. 13A is a top view of an eight-layer microfluidic device capable of combining discrete amounts of two fluids, the device including a deformable membrane that controls the admission of the fluids into a central chamber.

FIG. 13B is a top view of the device of FIG. 13A, illustrating section lines "C"—"C".

FIG. 13C is a cross-sectional view of a portion of the device of FIGS. 13A–13B along section lines "C"—"C" with the deformable membrane in an extended position to prevent the admission of two fluids into a central chamber.

FIG. 13D provides the same view as FIG. 13C, except that the deformable membrane is in a retracted position to permit the two fluids to enter the central chamber.

FIG. 14A is a cross-sectional view of at least a portion of a six-layer microfluidic device capable of combining discrete amounts of two fluids, the device including a deformable membrane illustrated in an extended position to prevent the admission of fluids into a central chamber.

FIG. 14B provides the same view as FIG. 14A, except that the deformable membrane is in a retracted position to permit the two fluids to enter the central chamber.

FIG. 15A is a cross-sectional view of at least a portion of an eight-layer microfluidic device capable of combining discrete amounts of two fluids, the device including a flexible membrane capable of deformation in multiple regions.

FIGS. 15B–15G provide cross-sectional views of the device of FIG. 15A in various states of operation to combine discrete amounts of two fluids.

FIG. 16A is a top view of an eight-layer microfluidic device having integral porous membranes, the device being capable of combining discrete amounts of two fluids.

FIG. 16B is a cross-sectional view of a portion of the device of FIG. 16A along section lines "D"—"D".

FIG. 17A is a top view of a multi-layer microfluidic device capable of combining metered amounts of two fluids to yield four discrete combinations.

FIG. 17B is a top view of a portion of the device of FIG. 17A, illustrating section lines "F"—"F".

FIG. 17C is a cross-sectional view of a portion of the device of FIG. 17A along section lines "F"—"F".

FIG. 18A is an exploded perspective view of a thirteen-layer microfluidic device capable of combining discrete amounts of three different samples and three different reagents to yield nine discrete combinations.

FIG. 18B is a top view of the assembled device of FIG. 18A.

FIG. 18C is an expanded top view of a portion of the device of FIGS. 18A–18B.

FIG. 19A is an exploded perspective view of a five-layer microfluidic device having eight fluid inputs along one axis and sixteen fluid inputs along another axis, the device permitting discrete amounts of fluids to be combined in many combinations.

FIG. 19B is a top view of the assembled device of FIG. 19A.

FIG. 20A is an exploded perspective view of a five-layer microfluidic device having a mixer and a long composite reactor channel.

FIG. 20B is a top view of the assembled device of FIG. 20A.

FIG. 21A is an exploded perspective view of a five-layer microfluidic device having two mixers for mixing three fluid streams, two interference-fit filters, and a long composite reactor channel.

FIG. 21B is a top view of the assembled device of FIG. 21A.

FIG. 22A is an exploded perspective view of a five-layer microfluidic reactor device having a diverter.

FIG. 22B is a top view of the assembled device of FIG. 22A.

FIGS. 22C–22D are cross-sectional views of the valve portions of the device of FIGS. 22A–22B, in the open and closed states, respectively.

FIGS. 23A–23C are partial cross-sectional views of various embodiments of heating and/or cooling elements in use with microfluidic devices.

FIGS. 24A–24B are partial cross-sectional views of microfluidic devices having a stencil layer formed with catalyst materials.

FIGS. 24C–24D are partial cross-sectional views of microfluidic devices having catalyst materials contained within the device.

FIGS. 25A–25B are partial cross-sectional views of microfluidic condensing devices.

FIG. 26A is an exploded perspective view of a first portion, including the first through third device layers, of a microfluidic methods development device having two groups of three parallel fluid process regions in fluid communication with a common slurry supply inlet and two common fluid supply inlets by way of three fluid distribution networks, with each group of fluid process regions having three process regions of different effective lengths due to sample loading channels having staggered lengths.

FIG. 26B is an exploded perspective view of a second portion, including the fourth through sixth device layers, of the device of FIG. 26A.

FIG. 26D is a reduced scale composite of FIGS. 26A–26C showing an exploded perspective view of the device of FIGS. 26A–26C.

FIG. 26F is a top view of a first portion of the device of FIGS. 26A–26E, including a slurry inlet and slurry distribution network for supplying slurry to multiple fluid process regions during fabrication of the device.

FIG. 26G is a top view of a second portion of the device of FIGS. 26A–26E, including a first common fluid inlet, a first fluid distribution network, a second common fluid inlet, and a second fluid distribution network, all used for distributing two fluids among multiple fluid process regions during operation of the device.

FIG. 27A is an exploded perspective view of a first portion, including the first through fourth device layers, of a microfluidic methods development device having two groups of three parallel fluid process regions in fluid communication with a common fluid supply inlet by way of a fluid distribution network, with each group of three process regions having a dedicated slurry supply inlet and distribution network to permit different solid materials to be provided to each group of three fluid process regions.

FIG. 27B is an exploded perspective view of a second portion, including the fifth and sixth device layers, of the device of FIG. 27A.

FIG. 27C is an exploded perspective view of a third portion, including the seventh through ninth device layers, of the device of FIGS. 27A–27B.

FIG. 27D is a reduced scale composite of FIGS. 27A–27C showing an exploded perspective view of the device of FIGS. 27A–27C.

FIG. 27F is a top view of a first portion of the device of FIGS. 27A–27E, including two slurry inlets and associated distribution networks for supplying a different slurry to each group of three fluid process regions during fabrication of the device.

FIG. 27G is a top view of a second portion of the device of FIGS. 27A–27E, including a common fluid inlet and fluid distribution network for distributing a fluid among all of the fluid process regions during operation of the device.

FIG. 28A is an exploded perspective view of a first portion, including the first through fourth device layers, of a microfluidic methods development device having six parallel process regions in fluid communication with two common fluid supply inlets by way of two fluid supply distribution networks, the device being adapted to provide mixtures with different ratios of the two fluids to each fluid process region.

FIG. 28B is an exploded perspective view of a second portion, including the fifth through eighth device layers, of the device of FIG. 28A.

FIG. 28C is an exploded perspective view of a third portion, including the ninth through eleventh device layers, of the device of FIGS. 28A–28B.

FIG. 28D is a reduced scale composite of FIGS. 28A–28C showing an exploded perspective view of the device of FIGS. 28A–28C.

FIG. 28E is a top view of the assembled device of FIGS. 28A–28D.

FIG. 28F is a top view of a first portion of the device of FIGS. 28A–28E, including a common first fluid inlet and a first fluid distribution network for supplying different amounts of the first fluid to each fluid process region during operation of the device.

FIG. 28G is a top view of a second portion of the device of FIGS. 28A–28E, including a common slurry inlet and associated slurry distribution network for supplying slurry to each fluid process region during fabrication of the device.

FIG. 28H is a top view of a third portion of the device of FIGS. 28A–28E, including a common second fluid inlet and second fluid distribution network for supplying different amounts of the second fluid to each fluid process region during operation of the device, and a common sample inlet and sample distribution network.

DETAILED DESCRIPTION

Definitions

Figure 26C:
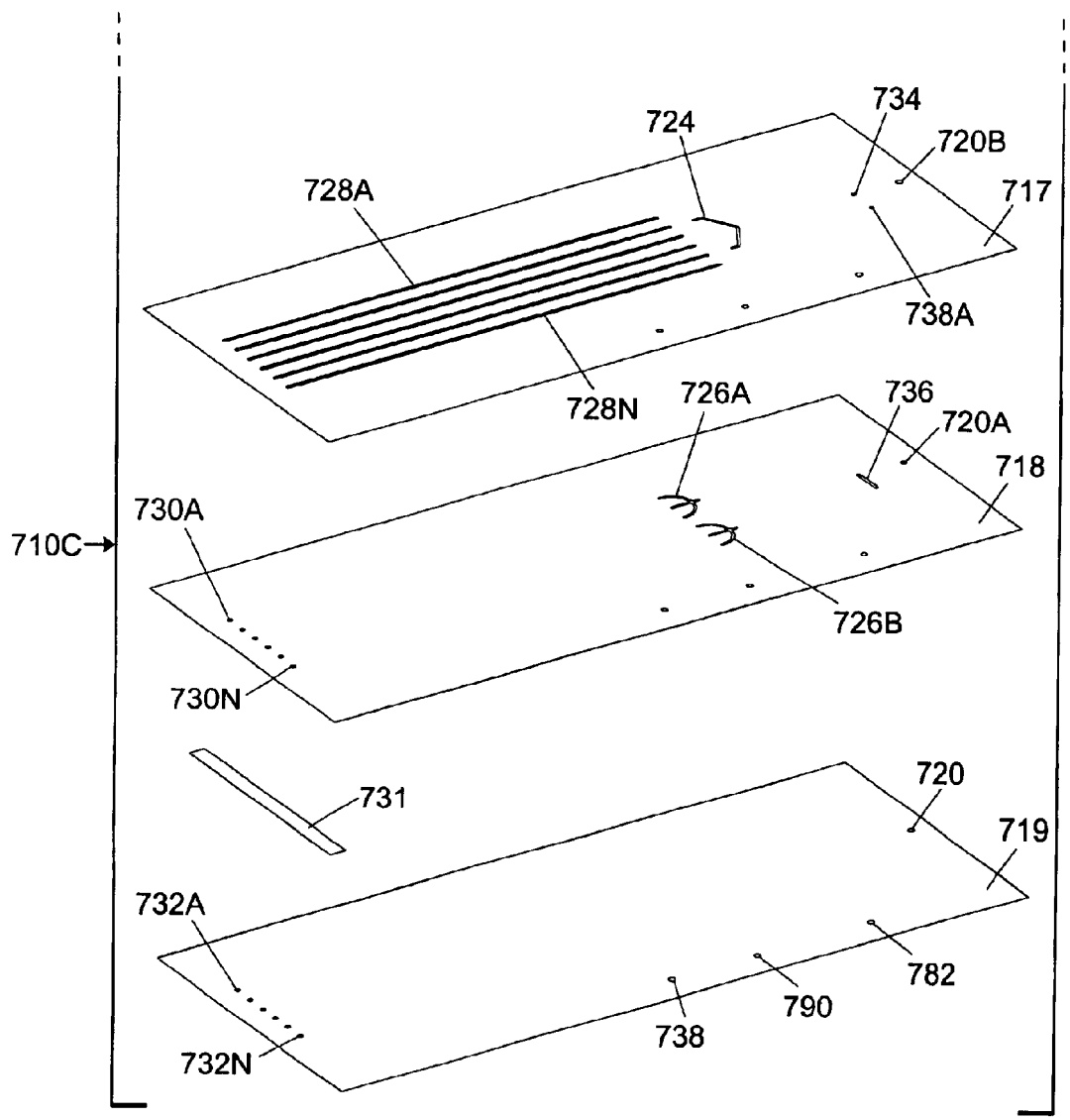
FIG. 26C is an exploded perspective view of a third portion, including the seventh through ninth device layers, of the device of FIGS. 26A–26B.

The term "adhesiveless" as used herein refers to the state of lacking any substance adapted to stick, bond, or otherwise adhere one surface to another.

The term "analysis" refers to the separation, extraction, purification, and/or identification of one or more ingredients of a substance.

The terms "channel" or "chamber" as used herein are not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" and "chambers" may be filled or may contain internal structures comprising, for example, valves, filters, and similar or equivalent components and materials.

The terms "chromatography column" and "column" may be used interchangeably herein and refer to a device or portion thereof comprising stationary phase material that is capable of separating at least a portion of an analyte in a fluid.

The term "flexible" as used herein means able to endure strain, particularly due to being bent, folded, or stretched, without breaking or suffering permanent injury. "Flexible"

as used herein may or may not include the further properties of being resilient or elastic.

The term "fluid process" as used herein refers to a series of actions or operations utilizing a fluid, characterized by any analysis or synthesis.

The term "fluid process region" as used herein refers to a region adapted to perform a fluid process.

The term "interpenetrably bound" as used herein refers to the condition of two adjacent polymer surfaces being bound along a substantially indistinct interface resulting from diffusion of polymer chains from each surface into the other.

The term "microfluidic" as used herein is to be understood to refer to structures or devices through which fluid(s) are capable of being passed or directed, wherein one or more of the dimensions is less than 500 microns.

The term "microfluidic system" as used herein refers to a microfluidic path, often including one or more microfluidic devices, capable of carrying or holding fluids. A microfluidic system may be composed of one or more subsystems.

The term "multiplexed" as used herein refers to multiple microfluidic systems on a given contiguous device wherein some or all of the systems are in fluid communication with one another.

The term "parallel" as used herein refers to the ability to concomitantly or substantially concurrently process two or more separate fluid volumes, and does not necessarily refer to a specific channel or chamber structure or layout.

The term "self-adhesive tape" as used herein refers to a material layer or film having an integral adhesive coating on one or both sides.

The term "substantially metal-free" as used herein means substantially free of metals, metal ions, and organometallic compounds.

The term "substantially sealed" as used herein refers to the condition of having a sufficiently low unintended leakage rate and/or leakage volume under given flow, fluid identity, or pressure conditions. Types of unintended leakage include leakage or pooling that accumulates in unintended regions between device layers and leakage to an environment outside a microfluidic device. A substantially sealed microstructure is contemplated to have one or more fluidic ports or apertures to provide desirable fluidic inlet or outlet utility.

The term "stencil" as used herein refers to a preferably substantially planar material layer or sheet through which one or more variously shaped and oriented portions have been cut or removed through the entire thickness of the layer, and which removed portions permit substantial fluid movement within the layer (as opposed to simple throughholes or vias for transmitting fluid from one layer to another layer). The outlines of cut or removed portions form the lateral boundaries of microstructures that are formed when a stencil is sandwiched between other layers such as substrates or other stencils.

The term "synthesis" as used herein refers to molecular rearrangement, addition, or subtraction of molecular species, generally including either chemical or biological transformation. Biological transformations include bioanalytical methods for the detection and quantification of molecular species of interest, also referred to herein as bioassays or assays.

Microfluidic Devices Generally

Certain embodiments of the present invention utilize microfluidic devices comprising sandwiched stencils. Stencil fabrication involves the lamination of at least three device layers including at least one stencil layer or sheet defining one or more microfluidic channels and/or other microstructures. A stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied. Additionally, one or more materials are preferably used to coat, seal, and/or adhere the stencil and/or substrate layers, to assist in forming useful microstructures.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Referring to FIGS. 1A–1B, a simple microfluidic device 10 is constructed by sandwiching a stencil 12 between two substrates 11, 13. Referring to FIG. 1A, an enclosed channel 15 is constructed by defining a channel 15 in the stencil layer 12 and sandwiching the stencil 12 between two substrates 11, 13, here represented by a bottom substrate 13 and a top substrate 11. Alternatively, stencil layers may be stacked directly on one another, rather than being immediately sandwiched between substrates. Substrates and stencil layers may be either rigid or flexible. Inlet and outlet apertures may be provided in the device 10. In this embodiment, two apertures 14 are defined in the top substrate 11. The assembled device is shown in FIG. 1B. Inlet and outlet apertures can be open to the environment surrounding the device, can lead to an adjacent stencil and/or substrate layer, or can lead to another modular device by way of a coupling device (discussed in further detail hereinafter).

The chemical nature of the individual stencil and substrate materials, and thus the chemistry of a microstructure used within a microfluidic module can be "tuned" for particular applications. A stencil material can be hydrophilic, hydrophobic, or ionic in nature. Stencil layers and substrate layers can be flexible. In various preferred embodiments, a stencil and substrate materials are selected from the group consisting of vinyl, filter material, paper or fabric, foil, and foam or foam sheets. In other preferred embodiments, stencil and substrate layers are formed from polymeric materials. Suitable polymers include, but are not limited to, polycarbonate, acrylic, polyurethane, polyethylene, including high-density polyethylene (HDPE) and ultra-high molecular weight polyethylene (UHMW), polypropylene (PP), polyvinylidene fluoride (PVDF), polytetrafluoroethylene (PTFE), nylon, polyethersulfone (PES), acetal copolymers, polyesterimides, polysulfones, polyphenylsulfones, ABS, polyvinylidene fluoride, polyphenylene oxide, and derivatives thereof. Further suitable materials include MYLAR™, polyester, polyimide (e.g., KAPTON™). Composite materials may also be used. In an especially preferred embodiment, the polymer is a fluorinated polymer, since fluorinated polymers often have superior resistance to aggressive solvents such as organic solvents. Additional materials will be mentioned hereinafter. Selection of particular materials for a desired application depends on numerous factors including: the types, concentrations, and residence times of substances (e.g., solvents, reactants, and products) present in regions of a device; temperature; pressure; pH; presence or absence of gases; and optical properties.

Adhesiveless Microfluidic Device Fabrication

In another attachment method, device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices. Further examples of adhesiveless methods for directly bonding layers of unoriented polypropylene to form stencil-based microfluidic structures are disclosed in commonly assigned published U.S. Patent Application Publication No. 2003/0106799 (Ser. No. 10/313,231, filed Dec. 6, 2002), which is hereby incorporated by reference as if set forth fully herein.

In addition to the use of adhesives and the adhesiveless bonding methods discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Microfluidic Coupling Devices

Referring to FIGS. 2A–2D, a microfluidic coupling device may be fabricated from multiple material layers. A microfluidic coupling device generally provides a fluidic interface to one or more external (preferably microfluidic) devices. Referring to FIGS. 2A–2B, a microfluidic coupling device 20 is formed from a first substrate layer 21 having an upper surface defining the top of the device 20, and from a second substrate layer 23 having a lower surface defining the bottom of the device 20. The coupling device also has at least one stencil layer 22 disposed between the first and second substrate layers 21, 23. The stencil layer 21 has at least one channel 24 formed in it, with at least one dimension less than about 500 microns. Preferably, each layer forming a microfluidic coupling device such as the device 20 has a height of between about 1 and 500 microns and a length and width each at least 100 times larger than the height. Various materials may be used for the stencil and substrate layers. In one example, stencil layer 21 is constructed from a MYLAR® material, stencil layer 22 from double sided tape and stencil layer 23 from single sided tape with a MYLAR® backing. In this manner, the top and bottom surfaces of the channel 24 are both MYLAR® material. The channel 24 is in fluid communication with a first aperture 25 defined in the second substrate layer 23. Although not required in all cases, the device 20 contains a second aperture 26 in the second substrate layer 23. The second aperture 26 is in fluid communication with the channel 24. In some embodiments, the second aperture may be located in the first substrate layer 21. Alternatively, all or a part of either substrate layer can be a semi-permeable membrane that allows gas to pass, but substantially prevents liquid from crossing. Other membranes that trap solid particles such as precipitate but permit liquid to pass may be used. In addition to coupling microfluidic modules or devices, microfluidic couplers may be used to collect samples.

Preferably, an adhesive is used to connect a microfluidic coupler with one or more external devices. More preferably, an adhesive used to couple the microfluidic coupler to the microfluidic device is non-permanent, so as to permit a coupler to be attached to a microfluidic device, fluid to be transferred by way of the coupler, and then the coupler to be removed. Using removable adhesive with a coupler facilitates removal of a sample from a device by removing a sample-containing coupler from a device. In another preferred embodiment, coupling between a microfluidic coupler and a microfluidic device is established with a tacky substance such as silicone.

In one embodiment utilizing a microfluidic coupler, the microfluidic coupling device is flexible. An entire microfluidic coupling device can be constructed of various films, papers, tapes, plastics and the like such that the coupling device is flexible. Flexibility can aid in alignment of the microfluidic coupling device to another microfluidic device or can facilitate coupling between two external microfluidic devices. The material used also can be malleable. Malleability aids in sealing a microfluidic coupler with another device, especially in cases where one or more mating surfaces are uneven.

The microfluidic coupler 20 of FIG. 2A can be constructed such that the lower surface of the second substrate 23 is adhesive so as to mate with another device (not shown) along one or more of the apertures 25, 26. The device 20 may also be constructed such that the upper surface of the first substrate layer 21 is adhesive. In one embodiment, a coupler has two apertures, one in the first substrate layer and one in the second substrate layer, and both the upper surface and lower surface are adhesive. Such an embodiment allows for rapid connection of the coupler to other microfluidic devices. The adhesive used may be either permanent or removable. In such an embodiment, the coupler may further include a backing layer removably adhered to the adhesive lower surface of the second substrate or a portion of that surface. The backing material protects the adhesive material until such a time as the microfluidic coupling device is to be attached to another microfluidic device. The backing material can be any suitable plastic, paper or foil.

A microfluidic coupler may also include a semipermeable membrane 27 covering the second aperture 26, as shown in FIGS. 2C–2D. The semipermeable membrane 27 allows gases to pass, but will not substantially allow a liquid to pass. For example, a suitable semipermeable membrane will allow air to pass through it, but will not allow water to pass. A suitable semipermeable membrane can have pores of a sufficient size to achieve the desired effect. In one embodiment, the semipermeable membrane is a polymeric material with a pore size of less than about 75 microns, and preferably less than about 10 microns. Examples of such filter materials include X-7744, a 7 micron pore size T3 sheet from Porex Technologies (Fairburn, Ga.) and GORE-TEX®-type materials.

In one embodiment, the first aperture 25 of the microfluidic device 20 shown in FIG. 2A is used as an inlet port, and the second aperture 26 is used as a vent for air escape. Alternatively, the second aperture 26 can be used as an exit port rather than a vent. The inlet port 25 can be directly coupled to another microfluidic device (not shown) using an adhesive. An adhesive can either be on the coupling device 20 or on the microfluidic device to which the coupling device 20 is to be attached.

In another preferred embodiment, porous materials can be used at an outlet of a microfluidic coupler to add impedance to the system. These materials can be chosen so that their properties are such that they have slight resistances to air or gas, and very large resistances to fluid flow. For example, pore size and material composition can be selected to produce the desired effects and impedances. Different materials can be used at various outlets. In this manner, the outlet materials can be used in conjunction with the overlap impedances to produce preferential fluid flow within a device.

In one embodiment, the bottom surface 28 of the microfluidic coupler 20 may be covered with an adhesive material along the inlet port 25 that allows the inlet port 25 to be connected to an outlet port of an external microfluidic device (not shown). Alternatively, the coupler surface 28 may be non-adhesive and the surface of the external microfluidic device to be coupled may be adhesive. In an alternative embodiment, mating surfaces of both the coupler and the external microfluidic are adhesive.

Adhesive can be placed on the bottom surface 28 of the microfluidic coupling device 20 in a number of ways. In a preferred embodiment, the bottom surface 28 of stencil layer 23 is inherently adhesive, such as an adhesive tape. In other embodiments, a coating is placed on the bottom surface 28 either before or after assembly. This coating can be accomplished in a number of ways, including spin coating, spray coating, etc Microfluidic Modules and Modular Systems One or more microfluidic tools may be integrated into modules, which may in turn be combined with other modules to form operative devices. One or more module combinations may be integrated into microfluidic devices, or combinations may be linked externally. For example, referring to FIGS. 3A–3F, multiple microfluidic modules 32, 34, 36 may be linked externally in various sequences using couplers 37. Providing discrete modules for performing different synthesis steps, wherein the modules interconnected in various arrangements by a user, permits reaction steps to be performed in a user-selected order. One benefit of this capability is that it enables each step in a multi-step synthesis reaction to be separately optimized. While simple serial arrangements of only three modules are provided in FIGS. 3A–3F, more complex arrangements involving larger numbers of modules are contemplated. For instance, individual modules may connect with two, three, or more other modules to provide complex networks.

In a preferred embodiment, a probe is used to define the channels and chambers of the stencil. In one embodiment, the probe is a cutting device mounted to, for example, a computer-controlled plotter. The probe selectively removes shapes from a material to form a stencil defining the lateral boundaries of microstructures (e.g., channels and chambers). In one embodiment, a heat probe is used to selectively melt or anneal heat-activated adhesive to form microstructures. In another embodiment, ultrasonic welding is used to create microstructures in layered stencils. For example, channels can be defined in two stencil layers. These layers can be "melted" together using ultrasonic welding.

When aggressive solvents such as organic solvents will be used with a microfluidic module or device according to the present invention, it is desirable to construct the module or device using relatively inert materials. Preferable construction materials include, but are not limited to fluorinated polymers (including, for example, FEP and PTFE), polypropylene, and polyethylene. In preferred embodiments constructed from multiple material layers, including those produced with sandwiched stencil methods, however, inert materials are challenging to work with because they are difficult to bind together. Specifically, these materials are usually characterized by low surface energies. To raise the surface energies of such materials to promote bindability, they may be surface treated. Desirable methods of surface treatment include: corona/plasma discharge; chemical treatment; and physical treatment. In a preferred embodiment, a microfluidic device was constructed employing a direct bonding method by heating sandwiched 2-mil layers of corona-treated FEP using a hot press at approximately 430° F. and 60 psi for approximately 40 seconds. In a more preferred embodiment, plasma-treated fluorinated polymers may be used.

In embodiments utilizing adhesives to bond layers of a microfluidic device intended for use with aggressive solvents, relatively inert adhesives are preferably used. Such adhesives include epoxies, acrylics (including UV-curable acrylics), polyurethanes, hot-melt adhesives, and certain rubber-based adhesives. Additionally, the adhesive bond line exposed to solvent in the resulting device is preferably thin to minimize interaction between the solvent and the adhesive.

In a preferred embodiment, a stencil layer is a flexible or elastomeric material, such as silicone, viton, or rubber, so as to enable tools including valving and pumping mechanisms. Pressure or mechanical force can be applied to a flexible layer to cause local bending or deformation, thereby blocking or partially obstructing a channel or chamber located above or below the flexible layer.

In a preferred embodiment, material forming a stencil is applied onto the substrate in only certain desired areas using printing techniques, such as, for example, silk screening. The material is then "cured" to form the channels and/or chambers. Examples include the use of an activatable or curable polymer as the stencil material. Another example is the use of paint or ink as the material. One example is the use of a Thick Medium heat-set acrylic from Genesis Artist Colors (Indianapolis, Ind.). In another embodiment, the entire surface of one of the substrates is coated with the stencil material. The stencil is then cured in areas where it is to remain and the rest of the material can be removed. In this embodiment, a curable epoxy material may be used. In a more preferred embodiment, the epoxy is a UV-curable epoxy. Alternatively, a two-part epoxy can be used, where the first part is patterned into place and the entire device is then soaked in the second part that only adheres to the stencil material in certain areas.

Coatings and Sealants

In a preferred embodiment, a sealant coat can serve to both coat and seal a microstructure. Referring to FIGS. 4A–4D, at least part of the surface of a stencil and/or substrate can be coated with a layer of sealant coat material. A cover plate substrate (which is preferably substantially planar during manufacture) can be layered upon the stencil to "cap" or complete the microstructure defined between the substrates. In FIG. 4C, the cover plate substrate is not coated. In FIG. 4D, the cover plate substrate is coated with a sealant coat material, which can be the same as or different than the other coatings used within the device. Referring to FIG. 4E, dabs of epoxy may be added to help adhere cover plate substrate, substrate, and stencil together. The epoxy can be added either before or after the sealant coat material has been cured. In another preferred embodiment, the layers of the device may be mechanically compressed (such as using clamps), separately or in addition to other device sealing methods. For example, gaskets can be used in conjunction with a compression device to help seal the microstructures. Mechanical sealing methods are especially desirable where coating materials do not serve to seal a microstructure.

Numerous suitable sealant coat materials having various desired properties can be used. The sealant coat material can be chemical and/or biological in nature, and can be hydrophobic or hydrophilic, depending on the application. Solids, liquids, gels and powders, or combinations thereof, can be used. Materials capable of carrying a surface charge can be used, as can neutral species. Sealants or coatings may serve additional functions, such as to provide filtration or impedance regions within a channel. Specific examples of coating materials suitable for use in devices described herein include Teflon®, Liquin®, Avatrel®, silicone, silicone mixtures, epoxies (including rubber masks), glue, liquid polymers, polymeric dispersions, plastics, liquid acrylic, paint, metals, oils, waxes, foams, photoresist, varnish, solder, and glass. Sealants can be chosen to protect a device from degradation by specific solvents or reactive molecules. Fluorinated polymers have excellent resistance to various solvents and chemicals, including organic solvents, and may be used. Examples include Teflon®, Avatrel®, polyvinylidene fluoride (PVDF), THV Fluorothermoplastic (Dyneon, St. Paul Minn.), Hostaflon TF 5035 (Dyneon), fluorinated ethylene propylene (FEP), polytetrafluoroethlyene (PTFE), and perfluoroalkoxy (PFA), among others. Alternatively, other coating materials can be used that specifically resist certain classes of solvents. Classes of solvents that may be used with devices as described herein include but are not limited to alcohols, aromatics, halogenated solvents (for example chlorinated solvents such as dichloromethane), ethers, polar protic, polar aprotic, hydrocarbon, and aqueous. Aqueous solvents may be acidic, basic, or neutral.

In a preferred embodiment, the sealant coat material is a polymer, such as, for example, polyethlyene glycol and cyanoacrylate. In other preferred embodiments, the coating material is biological in nature. Advantageously, in various applications, the biological coating material can be used to either promote or prevent adherence of materials. In certain embodiments, a biological coating material (e.g., a ligand) that specifically binds to certain biological materials is advantageously employed. Examples of biological coating materials useful with devices as described herein include proteins, antibodies, lipids, cells, tissues, nucleic acids, and peptides. More specific examples include avidin, streptavidin, polylysine, and enzymes. Other materials include lysis buffer for lysing cells and solid reagents. In another example, channels are heparinized to prevent clotting of blood samples. In certain embodiments, the coating materials are used to selectively bind materials that are present in the samples. In other preferred embodiments, coatings are used as catalytic materials. In another preferred embodiment, these catalytic materials are enzymatic in nature. Further in another embodiment, solid buffer materials are introduced to buffer a sample once it is injected.

The sealant coat material(s) can be deposited using one or more of a number of techniques. In a preferred embodiment, the sealant coat material(s) are spin-deposited onto a given substrate and/or stencil using a spinner or rotator. Specifically, an appropriate amount of a sealant coat material is placed on a substrate or stencil and the entire substrate or stencil is spun to produce a generally uniform sealant coat layer. In a preferred embodiment, the spin rate is between about 10 rotations per minute (rpm) and about 100,000 rpm. More preferably, the spin rate is about 500–20,000 rpm and, most preferably, is about 1,000–20,000 rpm. In order to make the coating thicker, multiple spin-deposition cycles can be used.

Alternatively, the sealant coat material can be deposited by spraying the sealant coat material onto a surface. For example, the sealant coat material can be ultrasonically sprayed through a nozzle or other orifice. In one embodiment, colloidal dispersions of the sealant coat material are prepared, the concentration being adjusted so that when sprayed onto a surface, a layer of desired thickness results. In another embodiment, the sealant coat material is sprayed directly onto a surface. In yet another embodiment, the sealant coat material is dissolved in an appropriate solvent and then sprayed onto the surface; when the solvent evaporates, the sealant coat material is left behind to form a coating layer. The sealant coat material can, alternatively, be applied by dipping a substrate and/or stencil into a volume of the sealant coat material. A single dip may produce a coating of desired thickness; in order to make the coating thicker, multiple dips may be applied. Alternatively, the sealant coat material can be deposited directly as a colloidal dispersion, or as a material dissolved in a solvent. In yet another preferred embodiment, the sealant coat material is stamped onto a surface. In all of these sealant deposition methods, the material may be further processed to ensure coating regularity or uniformity by methods such as pressing, rolling, scraping, and other equivalent methods known to those skilled in the art.

In another preferred embodiment, the material that is used to coat the surface of the microfluidic device is added to the device immediately prior to use, possibly after the device has already been constructed. For example, a coating material, such as a suspension or solvent containing solutes, particles, or beads, can be flushed through the microfluidic system immediately prior to use. Then further solvents and reactants may be added to the device to perform the desired synthesis. In a preferred embodiment, biological molecules can be flushed through the system immediately prior to use in order to prevent non-specific binding of molecules of interest such as proteins or nucleic acids. In another preferred embodiment, coating materials can be applied to the microfluidic system immediately prior to use that either promote or prevent cellular binding to surfaces. In this manner, cells can be localized within the microfluidic device where desired in order to perform cellular syntheses such as antibody production.

The embodiments described above are especially useful when the coating materials are damageable by light, air, or other environmental factors. For instance, certain coating materials may prove ineffective if exposed to oxygen or if they become dried out prior to use. Examples include, but are not limited to, collagen coatings used to promote cellular growth (which will be ineffective if dried prior to use) and certain catalyst materials which are susceptible to air, such as various palladium, rhodium, platinum, and other transition metal-based catalysts. These coating materials would be difficult to store for extended periods of time without problematic packaging. Thus, it may be necessary to add these coating materials to a microfluidic device immediately prior to use, or within a reasonable amount of time prior to use. The period of time before use that a coating should be added depends on the particular coating selected.

In another preferred embodiment, the coating material can be applied using traditional vacuum deposition or lithography techniques as would be known by one skilled in the art. In one embodiment, coating materials are applied through vapor deposition, CVD, or electron deposition.

In a preferred embodiment, the sealant coat material is patterned (e.g., by printing methods including silk screening techniques) onto a surface. In this embodiment, the sealant coat material can be used to coat only certain selected areas of the surface as defined by the silk screening mask. In another preferred embodiment, photoresist patterning can be used to achieve liftoff or etch patterning. The photoresist can then be removed to leave a coating only on certain areas of the surface. This procedure can be repeated as desired or necessary using different photoresist patterns and coating materials. In alternate embodiments, a variety of thin film deposition techniques can be used to deposit sealant coat materials. Such techniques include, but are not limited to, thermal evaporation, e-beam evaporation, sputtering, chemical vapor deposition, and laser deposition. These and other thin film deposition techniques are well known in the art. In addition, plating techniques can be used to deposit sealant coat materials. Such plating techniques include, but are not limited to, electroplating of metallic materials and chemical plating. The thickness of the sealant coat may be important in certain embodiments. Preferably, the thickness of the coating is sufficient to chemically protect the underlying surface and/or to adhere or seal an adjacent substrate and/or stencil. A potential problem of too thick a coating is the obstruction or blockage of microstructures, which can impede or prevent fluid flow therein. In certain embodiments, catalytic material may be added to certain portions of the microfluidic system to enhance synthesis in those portions.

In other embodiments, reactants of the synthetic protocol can be coated to certain portions of the device. In this manner, multi-step reactions may be accomplished without the necessity of inputting multiple reactants. In preferred embodiments, coating materials are composed of reactant materials in a solvent. These coatings are applied to certain portions of the microfluidic device prior, during or after construction. The solvent material evaporates or dries, leaving behind the reactant material for the reaction. For example, enzymes used during synthesis can be applied to regions of the microfluidic device during construction. The water may evaporate completely leaving behind the intact enzymes.

In other embodiments, the coating material can be composed of materials that do not act as reactants in the synthesis, but are required for the synthesis to be optimized. For example, salt can be dried in certain regions of the device as described above. In use, the microfluidic device brings solvent material into a region having a salt coating, then the salt dissolves into the solvent, and the presence of the salt enables the synthesis to occur or be enhanced. For example, many enzymatic reactions require the presence of salt for the enzymes to function properly.

In certain embodiments, the coating materials serve to alter the local surface free energy of the device. This can alter the manner in which the fluid interacts with the surfaces of microfluidic channels and devices and thus alter their function. For instance, coating materials can serve to change the chemical nature of a microfluidic channel. In certain embodiments, coatings may be used to render selected portions of the device hydrophobic or hydrophilic. In other embodiments, coating materials that alter their ionic character depending upon the solvent and/or the pH may be used (for instance, a silane material that is terminated with a carboxylic acid, amino, or hydroxy group).

Where the sealant coat material does not solely serve an adherence function, thinner coatings can be used. In fact, a molecular layer (or monolayer) may be preferable in certain instances. In a preferred embodiment, the sealant coat is a self-assembled monolayer of alkane thiols, which is particularly amenable to deposition on metal surfaces such as gold. Other similar thiols can be used. In another preferred embodiment, silanization reactions can be used to coat the substrates. Silanization is known to minimize adherence of certain biological materials such as nucleic acids and peptides. In yet another preferred embodiment, the microstructures are coated with a lipid bilayer or multilayer. In certain embodiments, these molecular monolayers are terminated with a biological molecule that is used to bind a molecule in the solution. Examples include nucleic acid-terminated alkane thiols and protein-terminated silanes.

It is sometimes necessary to adjust the viscosity of the sealant coat material prior to the coating step. In order to obtain a desired viscosity, some of the sealant coat materials may need to be diluted or thinned with other solvents or chemicals. Alternatively, the sealant coat materials can be heated prior to their deposition to alter their viscosity. Appropriate viscosity adjustments will be apparent to those skilled in the art.

Substrates and stencils to be coated are preferably cleaned prior to the coating and adhesion steps. Examples of cleaning techniques include soaking, sonicating, rinsing and plasma cleaning. Examples of cleaning materials include soap, surfactants, detergents, organic solvents and Freon®. In addition to surface cleaning or coating methods, surfaces can be chemically modified by corona/plasma discharge or chemical treatment.

In another preferred embodiment, flexible sealant coat materials can be used on certain layers of the device in order to enable valving and pumping mechanisms. A preferred flexible sealant coat material is silicone rubber. Pressure or mechanical force can be applied to the flexible layer to cause the material to bend and block a channel located above or below it. Three-dimensional structures can be formed using stencils defining channels and/or chambers.

In certain embodiments, the sealant coat materials can be chemically bonded to the underlying substrate and to the next layer. Alternatively, non-covalent chemical interactions can be used to hold the substrates together. The stencil material can be melted onto the underlying substrate or adhered using an adhesive or some other mechanism, such as heating. In other embodiments, the stencil can be mechanically pressed onto the underlying or adjacent substrate.

In another preferred embodiment, the stencils are not used as the fluidic devices themselves, but rather they (or a portion thereof) are used as forms to define a positive or negative mold. Various molding materials can be used, such as moldable polycarbonate or various silicones (see, e.g., Duffy et al.). Microfluidic devices can be prepared comprising microstructures formed using such molds.

Fabrication methods not employing stencils may be used to fabricate microfluidic synthesis modules or devices. Conventional techniques including etching, molding, embossing, and/or micromachining may be employed. Circuit-board-type substrates may be used to fabricate microfluidic synthesis devices. Elements or modules fabricated according to the above-mentiond techniques may or may not be subsequently layered.

In certain embodiments, a secondary mechanism may be used to help seal substrates and/or stencils together. In certain embodiments, these layers are held together mechanically. Examples include using nuts and bolts, tight-fitting pegs and holes, epoxy, BLU-TEK®, or an external clamp. Alternatively, pressure or vacuum can be used to accomplish this mechanical adhesion or sealing.

Functional Materials Disposed within Microstructures

In a preferred embodiment, a microstructure can be filled with any of a variety of filling materials, including reagents, catalysts, and separation materials. These filling materials, in certain embodiments, can be used to perform useful chemical and/or biological reactions. In a preferred embodiment, the filling materials are filters, which are useful for separating and/or purifying materials. These filters can be chemical or biological filters, or size-exclusion filters. These filters may bind unwanted material or, alternatively, may bind the material of interest so that it may be eluted off later. The filling materials can be hydrophobic or hydrophilic in nature, and can be charged or neutral. The filling material may be porous with various pore sizes. In a preferred embodiment, the filling material used to fill a channel or chamber is polymeric. Examples include, but are not limited to, polycarbonate, acrylic, polyurethane, high-density polyethylene (HDPE), ultra-high molecular weight polyethylene (UHMW), polypropylene (PP), polyvinylidene fluoride (PVDF), polytetrafluoroethylene (PTFE), Nafion®, nylon, and polyethersulfone (PES). In a preferred embodiment, the material used to fill the channel is a carbohydrate, such as agarose, alginate, starch, or carrageenan. The polymer may also be an electro-active polymer. In a preferred embodiment, the filling material is silica gel. In another preferred embodiment, the filling material is Sephadex® or Sephacil®. In another preferred embodiment, the material used to fill the channel is acrylamide or agarose. In another preferred embodiment, the material used to fill the channel is hydroxyapatite. In a preferred embodiment, the filling material used to fill the channel and/or chamber is a biological material. Examples include, but are not limited to, binding proteins, antibodies, antigens, lectin, enzymes, lipids, and any molecules that may interact specifically or nonspecifically with one or more of the species in the fluid.

In one preferred embodiment, the filling material is composed of a powder, such as charcoal or porous beads. In another preferred embodiment, the filling material is a reagent that is to be activated during the use of the device. Two examples are soluble reagents and catalysts. In another preferred embodiment, the filling material is a paper filter. This filter may be a commercially available material that is chemically modified to perform a specific function, such as binding a material or filtering a variety of materials. In another embodiment, the filling material is a solid catalyst, such as in the form of beads or a mesh. In still another embodiment, a catalyst is entrained in a liquid slurry and supplied to a microfluidic device having a filter or porous region. The filter or porous region traps the catalyst for use in facilitating a reaction within the device.

Various methods may be used to incorporate a filter into a microfluidic device. Filter configurations and materials may be selected to provide desired filtering utility. In certain applications, preventing leakage around the filter is not especially important. For these applications, physical placement of a piece of filter material in a channel may suffice for collecting or retaining a limited percentage of desired material. Modifications can be made to prevent substantial leakage around the filter. The stencil layer comprising the channel surrounding the filter may be composed of a material that reflows under application of heat or pressure. In another example, an entire device layer may be fabricated from filter material, with apertures in adjacent layers to provide fluid access to the filter. In certain instances, lateral wicking of the fluid into the filter layer is problematic. To address this, at least one stencil layer (defining one or more apertures) adjacent to the filter layer may be selected to prevent substantial lateral wicking of the fluid into the filter layer. For example, the adjacent stencil layer may be a hot melt material that flows into the filter material at desired locations and further seals the filter. Other localized chemical or physical treatment of the filter may be performed to reduce lateral wicking.

In a preferred embodiment, the material is composed of a single component that is already formed prior to being placed into a microstructure. Alternatively, the material can be formed from multiple components that can be separately placed into a channel; once in the channel, the materials can react to form the final filling material. Such curing can be accomplished in a variety of ways, and can be spontaneous or catalyzed by some other mechanism such as light, heat, a catalyst, solvent, drying, etc.

In one embodiment, the filling material is placed into the microstructures during the manufacturing process. In this manner, high-throughput techniques can be used to fill the channels. In one embodiment, high-throughput pick-and-place equipment, like that used in the electronics industry, is used to place the filter materials. In one embodiment, the filling material is patterned into the microstructures by, for example, silk-screening the material into the channels, or by using lithography, or by mechanically placing the material. In a preferred embodiment, an entire panel of devices can be coated simultaneously. A preferred panel size is approximately 18" by 24"; however, other panel sizes may be used. Fiducial marks may be placed on the panels for visual or optical alignment. Holes placed in the stencil may be used to align the stencil on the various machines used during the device manufacturing process. Silk screens comprising filter material are aligned with the devices on a panel.

In a preferred embodiment, a microfluidic device is used to concentrate samples. The device is constructed so that the volume of the wide channel/chamber and the large hole is about 2–100,000 times larger than the remaining filter chamber and channel volume. A large sample can be injected and washed many times. Then, a very small volume of eluent can be added to remove the sample that had been adhered to a filter material.

In one embodiment providing filtering utility, a microfluidic filter is specially constructed to minimize leakage around the filter. Referring to FIGS. 5A–5B, a microfluidic device 50 is composed of five layers. Starting at the bottom of FIG. 5A, a first layer 51 supports a filter element 55 and defines an inlet port 56 and an outlet port 57. The second layer 52 is a stencil layer that defines a chamber 58 having larger lateral dimensions than the filter element 55, but the layer 52 has a thickness that is smaller than the height of the filter element 55. The second layer 52, which is preferably made from a polymeric material, further defines a channel and via 59 in fluid communication with the outlet port 57, and a via 60 in fluid communication with the inlet port 56. The third stencil layer 53, which is preferably also made of a flexible polymeric material, defines a third layer aperture 61 that is substantially centrally located atop the filter element 55 but is smaller in size than the filter element 55. Because the filter height is greater than the height of the second layer that forms the chamber, the third layer material above the filter is pressed tightly against the filter 55. The third layer 53 also defines a via 62. The fourth stencil layer 54, which may be made from a polymeric material, defines a channel 63 terminating at a fourth layer aperture 64 that is adjacent to, and preferably larger than, the third layer aperture 61. The channel 63 may also be enlarged at the inlet side to mate with the via 62 in the third layer 53. The assembled device 50 is shown in FIG. 5B, a portion of which (along section lines "A—A") is shown in sectional view in FIG. 5C. In operation, fluid enters the device 50 through the inlet port 56, through vias 60, 62 into the fourth layer channel 63 and into the fourth layer aperture 64. From the fourth layer aperture 64, fluid flows into the third layer aperture 61 and is then forced through the filter 55. The third layer aperture 61 essentially determines the functional area of the filter 55, and can be varied accordingly. Upon exiting the filter 55, fluid flows through the second layer aperture 59 to the outlet port 57. The configuration of the device 50 prevents leakage in two ways: the membrane 53 above the filter 55 is tight against it, and the fluid pressure that builds up to push fluid through the filter 55 also pushes the membrane 53 even tighter against the filter 55. While the particular filter and surrounding chamber illustrated in FIGS. 5A–5C are illustrated as circular in shape, other shapes may be used. In other words, the foregoing design is by no means limited to filter materials and chambers that are circular in shape.

Microfluidic Metering

Providing accurate measurement of stoichiometric microfluidic volumes of reagents and solvents is highly desirable to perform syntheses on a microfluidic scale. FIGS. 6A–6B illustrate a microfluidic device 70 capable of sample metering and division. The microfluidic device 70 brings in a quantity of sample that has a large standard deviation, meters a known amount with a smaller standard deviation, divides the metered amount into three equal components, and brings the sample off-board for further analysis.

Referring to FIG. 6A, an inlet port 71, control port 72, and outlet ports 73 were created in a ⅛" thick polycarbonate base 87. Four stencil layers were created 74–77, each having channels 78–82 cut into them. In this example, single sided pieces of tape that consists of 3 mil (76-micron) polypropylene backing with permanent water based adhesive is used as the stencil material. The stencil layers were adhered together and onto the polycarbonate base. The assembled device is shown in FIG. 6B and contains four different types of overlap regions 83–86. All of the channels are 3-mils high, thus the overlap regions are 6-mils. At overlap 83, both channels are 40-mils wide and they overlap for 40-mils. At overlap 84, channel 80 is 40-mils wide and tapers down to 20-mils in the overlap region; channel 79 is 40-mils wide and channel 86 extends across 79 for 20-mils. Overlaps 85 and 86 are identical. The entry channels 79, 81 are 40-mils wide, the exit portions are 70-mils wide and the overlap is 40-mils in length.

In operation, a sample plug is injected at the inlet port 71 using a syringe pump at a constant flow rate. A fluidic impedance 83 is constructed immediately after the inlet to control the initial fluid flow. The fluid then passes into channel 79 and fills the channel until it reaches impedance 85. At this point, the excess fluid within the sample breaks through the microfluidic impedance at 84 before the microfluidic impedance at 85. The excess fluid passes down channel 80. Once all of the excess fluid has been sent to the waste channel 80, the control port 72 can be plugged, which increases the pressure within the channels. The amount of sample now ready for further analysis is defined by the volume of channel 79 between the two microfluidic impedances 84 and 85. If a different sample volume is desired, the microfluidic impedance 84 can be moved along channel 79 to alter the volume.

Once the air in channel 80 has been compressed sufficiently to build up enough pressure, microfluidic impedance 85 is overcome. The sample now enters chamber 81 and fills the entire chamber up to the impedances 86. Once this chamber has been completely filled, the output microfluidic impedances 86 are overcome and the samples can now be exported off the device for further analysis.

Pressure and/or Flow Regulation

Providing regulation capability to usefully vary flow to particular regions in a microfluidic system is desirable in certain synthesis methods. Compensating a microfluidic system for changes in relative pressure is one application. One technique for controlling the sensitivity of a microfluidic system to changes in relative pressure is to change the area of a regulatory region by way of a deformable membrane. A microfluidic chamber may be separated from another microfluidic chamber using a deformable membrane. Specific membranes can come in a wide variety of geometries and shapes. Microfluidic channels or segments thereof can overlap in a perpendicular format, at a non-perpendicular angle, or along parallel portions.

Referring to FIGS. 7A–7D, in one embodiment a microfluidic regulation device 199 is formed in five layers. The first layer 200 serves as a cover; the second layer 201 defines a channel 205 having a circular regulatory region; the third layer is a flexible membrane defining two vias 208 in fluid communication with the channel 205; the fourth layer 203 defines a channel 206 leading to a circular chamber 207 and; the fifth layer 204 defines an inlet port 209, and two outlet ports 210, 211. In use, fluid enters the device at inlet port 209 and travels to channel 205. The fluid then travels to channel 206 where it is split into two streams leading to the exit ports 210, 211. As the channel 205 is pressurized to deform the membrane 202, the unrestrained portion of the membrane 202A will deform downward into the channel segment 207. Depending on various factors including the area of the membrane subject to deformation, the force applied, and material properties such as flexibility of the membrane, deformation of the membrane portion 202A towards channel segment 207 may result in substantially complete blockage of fluid flow between channel segments 207 and the port 210. Alternatively, the membrane portion 202A may be deformed so as only to reduce fluid flow between channel segment 207 and port 210. Referring to FIG. 7D, the unrestrained membrane portion 202A is deformed so as to partially block fluid flow between segment 207 and port 210. Devices according to this design can be constructed with the port 210 in various positions relative to the path of the deformable membrane 202A. By placing the port 210 in a position near to the center of travel of the deformable membrane, a system can be constructed that can substantially block fluid flow through the through hole. The size and shape of the port will also affect the amount of pressure required.

In a preferred embodiment, the channel being controlled exits the regulatory region in a direction parallel to the direction of travel of the deformable membrane. Further material layers may be added to a flexible membrane regulation device, and the fluids on opposite sides of a membrane may be part of separate fluidic circuits. Referring to FIG. 7E, for example, a microfluidic regulation device is operated with a pressurized fluid, preferably air, contained in a first channel segment 225 adjacent to a flexible membrane layer 222. A rigid substrate 220 opposes the deformable membrane 222 along the first channel segment 225. A separate microfluidic circuit within the device permits fluidic passage between second and third channel segments 223, 227, which are connected with a hole 230 in an intermediary layer 224 adjacent to the unrestrained portion 222A of the flexible membrane. As the first channel 225 is pressurized, preferably with an external source (not shown), the deformable membrane portion 222A deforms downward to reduce the area of the second channel segment 227 adjacent to the hole 230, as shown in FIG. 7F. As the area of the second channel segment 227 is reduced, flow between the second and third channel segments 223, 227 is reduced. Further increases in pressure to the first channel segment 225 will completely block flow through the hole 230 within the device. The through hole 230 may be constructed in a variety of shapes to optimize regulation and/or shutoff characteristics. In different preferred embodiments, the through holes are circular and triangular in shape. Using this method, external control of flow (either regulation, shutoff or both) within a microfluidic device is provided.

Using these techniques, a system can be constructed in which deformation of the material results in either partial blockage or substantially complete blockage of the channel segment in response to a change in relative pressure. An elastic material can be used where reversible control of fluid flow is desired. Lowering the pressure in the higher relative pressure channel segment allows the deformable membrane to resume its neutral state, allowing unrestricted fluid flow. In some cases, it is desirable for the change in the microfluidic channel segment to be substantially permanent or irreversible. Such uses include shut-off valves to protect downstream components from damage caused by high flow or pressure. Upon increase in pressure in one channel segment, an inelastic material will be deformed towards the channel segment with lower pressure. The material will remain substantially in the deformed position.

A deformable membrane also can be made of materials with surface properties that alter its behavior. For example, a membrane can be tacky or have an adhesive coating. Such properties or coatings can be applied to one or both sides of the deformable membrane. Depending on the strength of the adhesive or degree of tackiness, the deformable membrane can operate as a variable switch. At low relative pressures, the membrane can act elastically. At high pressures, or for systems designed for the deformable membrane to physically contact the opposing wall of the adjacent channel segment, the deformation can result in a permanent closure of the adjacent channel segment. In another embodiment, the membrane used can be non-adhesive, but the surface against which it seals can be constructed with a tacky or adhesive surface. The degree of permanence of the closure relates to the elasticity of the membrane and the strength of the adhesive material used. Examples of the inelastic system include but are not limited to situations where the material is semi-malleable, for example, a metal foil, and situations where one or both of the surfaces have permanent or semi-permanent adhesives.

Flow Mixing in Microfluidic Devices

Mixing two or more fluidic streams is generally useful in performing synthesis efficiently, as well as in other contexts. On a microfluidic scale, mixing fluidic streams is generally difficult since surface effects tend to be dominant. A method and apparatus for mixing two or more microfluidic streams is provided herein. In one embodiment, an aperture permitting the passage of one microfluidic stream is placed in contact with a microfluidic channel containing another microfluidic stream. Preferably, the aperture is at least as wide as the channel; more preferably, the aperture is further configured as a slit. Further preferably, the fluid supplied to the aperture travels in a direction parallel to the flow within the channel. Referring to FIGS. 8A–8B, a microfluidic mixing device 90 is constructed in five layers. FIG. 8A is an exploded view of the five layers, and FIG. 8B is a top view of the assembled device 90. The first layer 91 serves as a cover; the second layer 92 defines a microfluidic channel 94 terminating in a wide aperture 95; the third layer 96 defines a via 98 and a slit 99 positioned below the aperture 95 in the second layer 92; the fourth layer 100 defines a via 101 and a narrow microfluidic channel 102 that expands into wide microfluidic channel 103; and the fifth layer 104 defines two fluidic inlet ports 106, 107 and one fluidic outlet port 108. In operation, two different fluids are introduced to the device 90 through the inlet ports 106, 107. The first fluidic stream is quickly directed to the wide channel 103 in the fourth layer 100. The second fluidic stream passes upward to the second layer 92, and then downward through the aperture 95 and slit 99 into the wide channel 103 in the fourth layer 100. When the first and second fluid streams are present in the wide channel 103, the second fluid stream is initially layered atop the first fluid stream. Since the width of the channel 103 is much greater than its height, layering one fluidic stream atop the other provides a large contact area between the two streams to promote rapid diffusion. In practice, complete mixing between two streams is routinely observed within devices constructed according to FIGS. 8A–8B within channel lengths of 2 inches or less, depending on factors including fluid flow rates. As with the other microfluidic tools disclosed herein, the slit mixer 90 may be integrated with other components into complex microfluidic devices. Various materials may be used for the layers of the device 90.

In another embodiment, microfluidic streams may be mixed in various proportions. For example, FIGS. 9A–9B illustrate a five-layer microfluidic device 110 according to an embodiment having two fluidic inlets, six unequal-length branch channels for each fluid, six mixer overlap regions, and six filters. FIG. 9A is an exploded view of the five layers, and FIG. 9B is a top view of the assembled device 110. Various materials may be used for the layers of the device 110. The first layer 111 serves as a cover. The second layer 112 defines a first supply channel 114 for directing a first fluid to six unequal-length branch channels 115. The supply channel 114 is significantly wider that the branches, preferably approximately equal to the sum of the widths of the branch channels 115. Each initially narrow branch channel 115 expands to a wider portion 116. The third layer 117 defines six mixer apertures 118 (configured as slits) at the end of each branch channel 116, six filter apertures 119, and a via 120. The fourth layer 121 defines a second supply channel 122 for directing a second fluid to six unequal-length branch channels 123. Each branch channel 123 terminates at widened portion positioned under a mixing aperture 118. The fourth layer 121 further defines six filter chambers 124 for holding filters 125, with each filter chamber 124 having a filter outlet channel 126. The six filter outlet channels 126 connect to a common outlet channel 128, which delivers fluid to outlet ports 131 in the fifth layer 129. The fifth layer 129 further defines inlet ports 130 for supplying fluids to the device 110. In operation, the device 110 receives two fluidic streams and splits each stream into six portions. For each stream, the flow rate of fluid leading to each of the six mixers is determined by the relative lengths of the channels leading to each mixer. Flow rate from a common supply is fastest to the shortest branch, and slowest to the longest branch (since the longest branch has a greater resistance to flow). Since the device 110 is configured to mix the contents of the shortest branch channel for the first fluid with the contents of the longest branch channel for the second fluid, and vice-versa, the resulting six mixtures each have different ratios of the first fluid to the second fluid. This may be useful, for example, for methods development. After mixing, the fluids are transported to individual filters 125. Preferably, the width of the outlet channels 126 is larger than the sum of the narrow branch channels 115, 123 to minimize flow resistance. In an alternative embodiment, the device may be constructed with in-layer filters downstream of the mixer overlap regions. In another alternative embodiment, catalyst materials may be substituted for the filters 125 to permit parallel synthesis.

Combinatorial Mixing/Synthesis

Combinatorial mixing is a valuable tool in performing synthesis. Various combinatorial mixers are disclosed herein. In one embodiment, a hydrophobic material defining a hole separates two adjacent chambers. When aqueous solutions are used, the hydrophobicity of the interface permits both chambers to be filled with fluid plugs without mixing. A pressure gradient can then be applied to force fluid through the hole in the hydrophobic layer to induce diffusion between the two plugs. In a preferred embodiment, the hole is actually a slit in which no material is removed from the intermediate dividing layer. In a more preferred embodiment, the slit is formed using a blade or die, rather than a laser, to minimize the removal of material from the intermediate layer.

Microfluidic devices as described herein may also be used to perform combinatorial syntheses of peptides, proteins, and DNA and RNA oligomers as currently performed in macrofluidic volumes. For example, the following may be performed: combinatorial synthesis and/or screening of plasmids, aptimers, proteins, and peptides; evaluating enzyme activity; and derivatizing proteins and carbohydrates. A broad spectrum of biochemical and electrophysiological assays may also be performed, including: (1) genomic analysis (sequencing, hybridization), PCR and/or other detection and amplification schemes for DNA, and RNA oligomers; (2) gene expression; (3) enzymatic activity assays; (4) receptor binding assays; and (5) ELISA assays. The foregoing assays may be performed in a variety of formats, such as: homogeneous, bead-based, and surface bound formats including microtiter-based assays using any of a number of detection schemes known to those skilled in the art. Furthermore, devices as described herein may be utilized to perform biological reactions, such as elucidation, prediction and manipulation of metabolic pathways in an organism under study using traditional tools, continuous production of biomolecules using specified enzymes or catalysts, and production and delivery of biomolecules or molecules active in biological systems such as a therapeutic agents.

Referring to FIGS. 1A–10C, a simple microfluidic combinatorial mixing device 140 is constructed in five layers. FIG. 10A is a top view of the device 140; FIG. 10B is an expanded top view of a portion of the device 140 illustrating section lines "B"—"B"; FIG. 1C is a cross-sectional view of a portion of the device 140 along section lines "B"—"B". The first layer 141 includes two pairs of ports 142, 143 each pair associated with a channel. A first channel 144 defined in the second layer 145 delivers fluid to a first chamber 146, and second channel 147 defined in the fourth layer 148 intersects the first channel 144 and delivers fluid to a second chamber 149. The first and second chambers 146, 149 are separated by the third layer 150, in which a slit 151 is defined along the boundary between the two chambers 146, 149. A fifth layer 152 defines the lower boundary of the second chamber 149. In a preferred embodiment, the first and fifth layers 141, 152 are made of a polymeric film, the second layer 145 is made of a double-sided tape, the third layer 150 is made of single-sided tape with the adhesive facing down, and the fourth layer 148 is made of single- or double-sided tape.

In operation, a first fluid plug is formed in the first chamber 146 when the first channel 144 is filled, and a second fluid plug in the second chamber 149 is formed when the second channel 147 is filled. The slit in the third layer 151 is held shut by the adhesive on the bottom side of the third layer 150. Once the plugs are formed, the ports 142, 143 to each channel 144, 147 are sealed (such as by heat sealing). Thereafter, the slit 151 in the third layer 150 is ruptured, breaking the adhesive seal between the chambers 146, 149 to allow the plugs to diffuse together. This rupture may be advantageously accomplished by bending the device 140 along the direction of the slit 151. Alternatively, establishing pressure differential between the chambers 146, 149 can rupture the adhesive seal.

One advantage of the design according to FIGS. 1A–10C is that it can be multiplexed without adding further layers or complexity. For example, FIGS. 11A–11B show a 2×2 combinatorial plug mixer sharing the same basic five-layer design as the device shown in FIGS. 10A–10C, except the device 160 has four channels 161, 162 in communication with eight ports 163 in the first layer 155, four chambers 164 in the second layer 156, four chambers 165 in the fourth layer 158, and four slits 166 defined in the third layer 157. Different fluids may be added to each of the four channels 161, 162. The chambers 164, 165 can then be sealed from the channels 161, 162. For example, a heat probe (not shown) may be used to locally seal the channels 161, 162. If different fluids are used in each of the four channels 161, 162, then the four mixing chambers 164, 165 will each have different plug combinations. Much larger and/or denser combinatorial mixers may be prepared according to the same basic design.

In another embodiment, a combinatorial mixer may be fabricated using a laser welding technique to weakly partition a mixing chamber into two subchambers. Referring to FIGS. 12A–12F, a combinatorial mixer 170 is formed in three layers. The first layer 171 has two pairs of ports 174, 175 each communicating with one of two channels 176, 177 defined in the second layer 172. The second layer 172 further defines a chamber 178 connecting the two channels 176, 177. Preferably, the first and third layers 171, 173 are formed from a thermoplastic film or from films coated with a thermoplastic polymer, and the second layer 172 is a double-sided tape. To partition the chamber 178, a laser (not shown) is applied to the first layer in a line, causing the thermoplastic material to melt locally without cutting through the first layer 171. Using this technique, the first layer 171 may be weakly bonded to the third layer 173 along the path 179 of the laser heating. FIGS. 12A and 12B show top views and FIG. 12C shows a cross-sectional view along section lines "E"—"E" (illustrated in FIG. 12B) of a chamber 178 before welding. FIGS. 12D–VF show these views after the chamber is partitioned. The resulting bond between the first and third layers is weak. Following laser welding to partition the chamber, the two resulting sub-chambers 178A, 178B are filled with fluid. To enable mixing between the fluids, there exist several different ways of breaking the seal between chambers. In one embodiment, the fluidic ports are sealed, such as by localized heating with a heat probe (not shown), and the seal between the subchambers 178A, 178B is broken by applying an external force or pressure to the chamber 178. In another embodiment, all but one of the fluidic ports are sealed. The unsealed port is then used to supply pressure from an external source (not shown). In yet another embodiment, all fluidic ports 174, 175 are sealed and an external suction is applied above the seal to break it.

In a similar embodiment, a chamber is partitioned into multiple subchambers with an adhesive bond. Referring to FIGS. 12G–12J, a combinatorial mixer 180 is formed in five layers 181–185. The first layer 181 is preferably a rigid substrate and defines two pairs of fluidic ports 186, 187 connected to one of two channels 188, 189, defined in the fourth layer 184. The second layer 182 is preferably a double-sided tape. The third layer 183 is preferably a non-adhesive film defining a central channel 190. The fourth layer 184 is preferably a double-sided adhesive defining a chamber 191 below the central channel 190 in the third layer 183. The fifth layer 185 is preferably a flexible film. To partition the chamber 191 into two sub-chambers 191A, 191B the fifth layer 185 is pushed and deformed upward to contact an exposed adhesive region in the second layer 182 above the central channel 190 defined in the third layer 183. Once contact is established, the fifth layer 185 locally adheres to the second layer 182, separating the chamber 191 into two subchambers 191A, 191B. FIG. 12I shows a cross-sectional view of a chamber 191 (along section lines "F"—"F" illustrated in FIG. 12H) before partitioning, and FIG. 12J shows this view after the chamber 191 is partitioned. The resulting adhesive seal between the second and fifth layers 182, 185 is weak, but maintains fluidic separation between the two subchambers 191A, 191B at low fluid pressures. Following formation of the subchambers 191A, 191B, fluid can then be filled independently into both subchambers. As was the case with the laser-sealed devices, several methods may be used to break the seal. In one embodiment, the fluidic ports are sealed and the seal between subchambers 191A, 191B is broken by applying pressure to one of the subchambers. In another embodiment, all but one of the fluidic ports are sealed. The open port is then used to supply pressure from an external source (not shown). In yet another embodiment, all inlets and outlets are sealed and an external suction is applied adjacent to the seal to break it. In a preferred embodiment, an additional channel is defined in a sixth layer (not shown) and placed below the fifth layer 185 along the adhesive seal region. Pressure can be applied to the additional channel to deform the third layer so as to partition the chamber, and vacuum can then be applied to break the seal.

In another embodiment configured similarly to those described immediately above, a clamp (not shown) is used to partition a chamber by pinching it closed along a centerline to permit multiple subchambers to be filled, and then the clamp is released to allow the two plugs to mix.

In another embodiment, a microfluidic combinatorial mixer may be fabricated with a collapsed chamber to which vacuum is applied so as to open the chamber and simultaneously draw fluid plugs into the chamber. Referring to FIGS. 13A–13D, a microfluidic combinatorial mixing device is fabricated in eight layers. FIGS. 13A–13B show top views of the device 231, and FIGS. 13C–13D show the device in operation in sectional views along the section lines "C—C" provided in FIG. 13B. Preferably, the first layer 232 is a rigid substrate, the second, fourth, and sixth layers 233, 235, 237 are double-sided tape, the third layer 234 is a flexible film such as latex, the fifth layer 236 is a film, the seventh layer 238 is single-sided tape with the adhesive facing down, and the eighth layer 239 is a hydrophobic porous membrane. The second layer 233 defines an actuation chamber 240 that may be de-pressurized and/or pressurized by an external source (not shown) connected to the device 231 at an actuation port 241 to deform the unrestrained portion 242 of the flexible third layer 234. Below the unrestrained portion 242 of the third layer membrane is a mixing chamber 244 in the fourth layer 235. Defined in the fifth layer 236 at the lower boundary of the mixing chamber 244 are fluidic inlet apertures 245, 246 for delivering fluid plugs to the chamber 244, the plugs supplied to the device 231 through external ports 247, 248 in communication with fluidic channels 251 in the sixth layer 237. Downward deformation of the flexible portion 242 covers the fluidic inlet apertures 245, 246 to prevent fluidic access to the chamber 244.

In operation, pressure is initially applied to the actuation chamber 240 to deform the flexible portion 242 so as to cover the fluidic inlet apertures 245, 246 and prevent fluidic access to the chamber 244. With the mixing chamber 244 closed, microfluidic streams are supplied to the device 231 through external ports 247, 248 into channels 251 and split using splitters 252 into channel segments 249, 250. The porous eighth layer 239 and vents 253, 254 defined therein permit the fluids to displace any air present in the device 231. Once filled, fluid in the channel segments 249, 250 may be isolated into plugs of discrete volume by purging the channels 251, such as with pressurized air or nitrogen. Once the plugs are formed, vacuum is applied to the actuation chamber to cause the flexible portion 242 to deflect upward. Referring to FIG. 13D, upward deflection of the flexible portion 242 creates a vacuum in the mixing chamber 244 that draws the plugs into the mixing chamber 244 to enable mixing to occur.

In a further embodiment utilizing a flexible membrane, two fluid plugs are formed behind a deformed flexible membrane, and the application of pressure behind the samples opens the mixing chamber and permits the samples the mix. Referring to FIGS. 14A–14B, which are cross-sectional views of a portion 260 of a microfluidic mixing device, the device is formed in six layers. Preferably, the first layer 261 is a rigid substrate, the second and fourth layers 263, 265 are double-sided tape, the third layer 264 is a flexible membrane such as 4-mil thick latex, the fifth 265 layer is single-sided tape with the adhesive facing down, and the sixth layer 266 is a hydrophobic porous membrane. The second layer 262 defines an actuation chamber 267 and the fourth layer 264 defines a mixing chamber 271, with the two chambers separated by a flexible membrane 268. Fluidic channel segments 269, 270 in the fourth layer 264 transport fluid to the boundaries of the mixing chamber 271. Vents 272, 273 are defined in the fifth layer 266 to permit air entrained in the device portion 260 to be displaced by liquid as it enters the channel segments 269, 270.

In operation, the actuation chamber 267 is pressurized from an external source (not shown) to deform the flexible membrane 268 downward to close the mixing chamber 271, as shown in FIG. 14A. The channel segments 269, 270 are then filled with fluids to be mixed. The fluids are free to flow up to the collapsed chamber due to the vents 272, 273. Once plugs are formed in the channel segments 269, 270 and the back pressure to the fluid is released, the pressure in the actuation chamber 267 is released. However, vacuum is not pulled, so the chamber remains collapsed. The plugs in the channel segments are then pressurized. The fluid then enters the mixing chamber 271 and deforms the flexible membrane 268 upward, as depicted in FIG. 13B. Once each plug is present in the mixing chamber 271, the pressure applied to each plug escapes through the vents 272, 273 and the plugs stop flowing.

In another embodiment, multiple collapsed chambers are used within a microfluidic mixing device to minimize the presence of air in the mixing chamber with the fluids to be mixed. Referring to FIGS. 15A–15G, one example of such a mixing device 280 is constructed in eight layers. Preferably, the first layer 281 is a rigid substrate; the second, fourth, and sixth layers 282, 284, 286 are double-sided tape; the third layer 283 is a flexible membrane such as latex; the fifth layer 285 is a film; the seventh layer 287 is a single-sided tape with the adhesive side down; and the eighth layer 288 is a porous film. More preferably, the eighth layer 288 is also hydrophobic. The second layer 282 defines two central actuator chambers 289, 290 disposed above a mixing chamber 291 (defined in the fourth layer 284) and two lateral actuator chambers 292, 293 disposed above fluidic apertures 294, 295. The fluidic apertures 294, 295 communicate fluids from channel segments 296, 297 to the mixing chamber 291. FIG. 15A shows a cross-sectional view of the mixing device 280 before any action is initiated.

Referring to FIG. 15B, to prepare for operating the device 281 the central actuation chambers 289, 290 above the mixing chamber 291 are pressurized first, preferably to approximately 10 psi, to locally deform the third layer membrane 283 and close the mixing chamber 291. Lower pressures may be used; however, a pressure of approximately 10 psi has been found to provide effective sealing. The lateral actuation chambers 292, 293 along the inlet apertures 294, 295 to the mixing chamber 291 are then pressurized, preferably to approximately 10 psi, to seal the apertures 294, 295. The combination of the lateral actuation chambers 292, 293 and flexible third layer membrane 283 operate as membrane valves. The reason that the central actuation chambers 289, 290 are pressurized before the lateral actuation chambers 292, 293 is to minimize the entrapment of air in the mixing chamber 291. Following pressurization of the chambers 289, 290, 292, 293, fluids are introduced into the first and second channel segments 296, 297 to form two plugs to be mixed. As the fluids are introduced into the channel segments 296, 297, any air present in the channels may be displaced through the vents 298, 299 and the porous eighth layer 288. The plugs are then introduced into the mixing chamber 291 one at a time. To introduce the first plug, the plug is pressurized to approximately 15 inches H$_2$O, then the first lateral actuation chamber 292 and the first central actuation chamber 290 are depressurized, permitting the plug to flow into one half of the mixing chamber 291, as shown in FIG. 15D. Following introduction of the first plug, the first lateral actuation chamber 293 is re-pressurized to seal the first plug into the mixing chamber 291, as shown in FIG. 15E, thereby preventing escape or evaporation. The preceding two steps are then repeated for the second plug: the plug is pressurized, the chambers 292, 289 are opened (as shown in FIG. 15F), the plug enters the mixing chamber 291, and the second actuation chamber 292 is re-pressurized to seal the mixing chamber 291. The final state of the device, with the two plugs present and sealed within the mixing chamber 291 due to pressurization of the lateral actuation chambers 292, 293 is shown in FIG. 15G.

In another embodiment, a vacuum chamber is created by providing a porous membrane between a mixing chamber and an actuation chamber. Referring to FIGS. 16A–16B, a microfluidic mixing device 300 is constructed in eight layers. FIG. 16A is a top view of the device, and FIG. 16B is a cross-sectional view of the device along section lines "D"—"D" provided in FIG. 16A. The first layer 301 is a substrate defining fluidic ports 310, 311 for communicating fluid to the device 300 and an actuation port 312 connected to an external vacuum source (not shown). Preferably, the second, fourth, and sixth layers 302, 304, 306 are double-sided tape; the third and fifth layers 303, 305 are hydrophobic porous membranes; the seventh layer 307 is single-sided tape with the adhesive facing down; and the eighth layer 308 is a film. The second layer 302 defines an actuation chamber 313, the fourth layer 304 defines a mixing chamber 314, and the sixth layer 306 defines fluidic inlet apertures 315, 316 that permit fluid to be supplied to the mixing chamber 314. A function of the third layer 303 is to prevent liquid from entering the actuation chamber 313. In operation, fluids are supplied to the device 300 at low pressure via the external ports 310, 311 and communicated to channels 317. A splitter 318 in each channel 317 splits the fluid to a channel segment 319 so as to form a fluid plug. The fifth layer 305 functions to stop plugs from entering the mixing chamber 314 as the plugs are metered. In a preferred embodiment, the fifth layer 305 is more porous than the third layer 303 so that fluid can be drawn into the mixing chamber 314, but prevented from entering the actuation chamber 313. Vacuum is then applied to the actuation chamber 313 to draw the fluid plugs through the porous fifth layer 305 into the mixing chamber 314, where the plugs mix.

Another embodiment for mixing microfluidic plugs utilizes a porous material, preferably a hydrophobic porous material, to vent a mixing chamber or other reaction area. Referring to FIGS. 17A–17C, a combinatorial microfluidic mixing device for making four mixtures from two fluids is constructed in eight layers. The device permits four plugs of each fluid to be metered off and then mixed in simultaneous fashion. FIG. 17A is a top view of the device 320, FIG. 17B is an expanded top view of a portion of the device showing section lines "F"—"F", and FIG. 17C is a sectional view of a portion of the device 320 along section lines "F"—"F". Preferably, the first layer 321 is a substrate; the second, fourth, and sixth layers 322, 324, 326 are double-sided tape; the third layer 323 is a flexible membrane such as a 4 mil thick latex film; the fifth layer 325 is a film; the seventh layer 327 is single-sided tape with the adhesive facing down; and the eighth layer 328 is a porous membrane. More preferably, the first layer 321 is a rigid solid to facilitate controlled pressurizing of actuation chambers 329, 330 in the second layer 322. The second layer 322 defines two actuation chambers 329, 330 positioned above fluidic apertures 332, 333 in the fifth layer 325, so that pressurization of the actuation chambers 329, 330 locally deforms the flexible third layer 323 to block the apertures 332, 333, operating as membrane valves. A mixing chamber 334 is defined in the fourth through seventh layers 324–327, with the lower boundary of the chamber 334 being the porous eighth layer 328. Upon delivery of the plugs to the mixing chamber 334, any air entrained in the chamber 334 will escape through the porous layer 328 but prevent the plugs from escaping. The fluidic apertures 332, 333 are laterally offset from the walls of the mixing chamber 334 in the fifth layer 325 to permit the apertures 332, 333 to be fully covered when the actuation chambers 329, 330 are pressurized.

In operation, one plug is provided to each channel segment 335, 336 at opposite sides of the mixing chamber 334. The plugs are supplied to the channel segments 335, 336 from inlet ports 337A, 337B, 338A, 338B in the first layer 321 and fluidic channels 339, 340. Along each side of the device, splitters 341 divide the fluidic streams into four segments 335, 336 wherein the plugs are formed. The aggregate volume of each plug should be slightly less than half the mixing chamber volume to permit both plugs to fit with a little room for air to escape on each side. Pressure is applied to the plugs from behind as they the plugs are conveyed to the mixing chamber 334; preferably, the applied pressure is less than the pressure applied to the actuation chambers 329, 330 to prevent the membrane valves from leaking. In a preferred embodiment, the actuation chambers 329, 330 are pressurized to approximately about 2–4 psi to close the valves, and the pressure applied to each fluid plug is less than 1 psi. However, the degree of pressure to be applied depends on the porosity and material of the porous eighth layer 328. There is a 'water intrusion pressure' at which water will permeate the porous membrane 328. The pressure applied to the fluid plugs advantageously does not exceed the water intrusion pressure of the porous eighth layer 328. In a preferred embodiment, a pressure of 0.3 psi applied to the fluid plugs is sufficient to move the fluid and does not exceed the water intrusion pressure for most hydrophobic porous membranes.

In addition to permitting gaseous reaction products to escape a microfluidic devices, porous interfaces such as porous membranes may also be used to supply desirable gases to a reaction area. For example, hydrogen gas may be supplied to a reaction area through a porous interface to permit various hydrogen-consuming (e.g., hydrogenation) reactions. A porous interface may also be used to supply a nitrogen blanket to a reaction area to provide an inert environment (e.g., if it is desired to prevent oxygen fouling of catalyst or other materials).

FIGS. 18A–18C show an example of a combinatorial microfluidic mixing device 600 according to one embodiment permitting three different samples and three different reagents, all of uncertain volumes, to be metered and mixed in a combinatorial manner in nine separate mixing chambers. Referring to FIG. 18A, the device 350 was constructed from thirteen layers, including a substrate and stacked stencils. The first layer 351 was a rigid 2-¼"×2-¼" square substrate having two pairs of ports 365, 366 for a control fluid such as "high pressure" (approximately 10 psi) air. The second layer 352, constructed from a 5.5 mil double-sided tape having a PET carrier and acrylic adhesive on both sides, was used to control valves within each mixing chamber 375. As used in connection with FIGS. 18A–18C, the term "valve" refers to the combination of a pressurizable chamber, a response chamber, and a deformable flexible membrane separating the chambers. Two separate networks 367, 368 of channels and chambers, each fed by vias 367A, 368A at opposite corners of the device 350, were defined in the second layer 352 to permit one side of each mixing chamber 375 to be simultaneously controlled by the high pressure control fluid. The third layer 353 was made of 2 mil biaxially oriented polypropylene film and defined nine pairs of membrane valve vias 370, one port of each pair being in fluid communication with one network in the second layer 352. The second layer 352 and third layer 353 further included vias 369, 371 to permit transmission of fluid from the ports 366 in the first layer 351 to the fourth layer 354. The fourth layer 354 was formed of the same double sided tape as used in the second layer 352, and was used to control membrane valve regions 377 adjacent to the mixing chambers 375. Similar to the second layer 352, two separate networks 373, 374 of channels and chambers, fed by the vias 371, were defined in the fourth layer 354 to permit one membrane valve region 377 corresponding to each mixing chamber 375 to be simultaneously controlled. The fifth layer 355 was a flexible membrane made of 4 mil latex film, used as the valving material in the mixing chambers 375 and membrane valve regions 377. The sixth layer 356 was constructed from the same double sided tape used in the second and fourth layers 352, 354. Defined in the sixth layer 356 were nine mixing chambers 375, each having two associated membrane valve cavities 377 and channels 376 to connect each membrane valve cavity to its associated mixing chamber 375. The seventh layer 357 was made of the same polypropylene film material used in the third layer 353, and defined nine pairs of vias 378 connecting to the membrane valve cavities 377 in the sixth layer 356. The eighth layer 358 was made of double sided tape (the same as the second, fourth, and sixth layers 352, 354, 356) and defined three networks 379 of branched channels (each incorporating three splitters 380) to divide three streams of fluid (e.g., reagents) into three plugs per channel. The ninth layer 359 was made of the same polypropylene film as was used in the third and seventh layers 353, 357, and included vent vias 384 (to permit air to escape downward when loading plugs), central fluid vias 383 to provide fluidic connection to the mixing chambers 375, and peripheral vias 382. The tenth layer 360 was made of double-sided tape (the same as used in the preceding even-numbered layers) and defined three networks 386 of branched channels, each incorporating three splitters 388 and functioning the same as the networks in the eighth layer 358 to divide three fluids (e.g., three samples) into a total of nine plugs. The tenth layer 360 further defined vias for communicating fluid to the ninth layer 359 and onward to the eighth layer 358. The eleventh layer 361 was made of single sided tape composed of a 1 mil polyester carrier with 0.8 mil of acrylic adhesive, adhesive side down. The eleventh layer 361 functioned to provide a smooth bottom surface for channels in the tenth layer 360, to provide vent vias 390, and peripheral fluid vias 389, 391, e.g., for samples and reagents. The twelfth layer 362 was made of a hydrophobic porous polyethylene film with pore sizes of 2.5–4.5 microns, and functioned to allow air to escape from plug channels, but keep fluid within the device 350. Since the porous film of the twelfth layer 362 was opaque, nine central windows 393 were cut in the film to facilitate observation or analysis of the mixing chambers 375 from below. Further defined in the twelfth layer 362 were peripheral fluid vias 392, 394, e.g., for samples and reagents. Finally, the thirteenth layer 363 was made of single-sided tape (the same material as layer 11) and functioned to cover the porous material of the twelfth layer 362 except where central vents 396 and peripheral ports 395 were defined. The assembled device 350 is shown in FIG. 18B, with a portion of the device enlarged in FIG. 18C to show additional detail.

To prepare the combinatorial mixing device 350 for operation, the device 350 was connected to a high-pressure air source and isolation valves (not shown) from above at the ports 365, 366, and to six fluid sources (delivering liquid and low-pressure air) from below at the ports 395. The high-pressure air sources were pressurized to approximately 10 psi to close the mixing chamber 375 valves and the associated membrane valves 377. The mixing chamber valves were of a "collapsed chamber" design, further discussed herein. In operation, with the valves 375, 377 closed, six liquid streams were injected into the device with syringes (not shown) using the ports 395 to completely fill the branched channel networks 379, 386 located in the eighth and tenth layers 358, 360. Thereafter, air (behind each liquid in the syringes) was forced into the ports 395 to purge excess liquids in the channels 379, 386 out of the device, leaving behind metered plugs of liquid filling only the channel branches. Thus, for each fluid stream, three plugs of a known volume were metered off from streams of indeterminate volume to form a total of eighteen plugs. Two plugs were formed adjacent to each mixing chamber 375, with each mixing chamber 375 having two mixing chamber 375 valves (actuated by the networks 367, 368) and two associated membrane valves 377 (actuated by the network 373, 374). Following formation of all eighteen plugs, they were moved into the mixing chambers in groups of nine. The following procedure applies simultaneously to each of the nine chambers, since the controls for each mixing chamber were connected in parallel. First, two high pressure air sources were released, reducing localized downward deflection of the flexible membrane in selected locations to open one mixing chamber valve and the corresponding membrane valve 377. With these valves open, one plug was forced into the chamber by pressurizing the fluid inlet to approximately 15 inches of water. Once the plug was in the chamber 375, the membrane valve was closed. This process was then repeated on the other half of the mixing chamber 375: as the other mixing chamber valve and corresponding membrane valve were opened, the plug was pushed into the chamber, and the membrane valve was closed. At that point, both plugs were present in the mixing chamber and they were free to diffuse together. Thus, a total of nine microfluidic mixtures are formed quickly in a compact 2-¼×2-¼ device 350. The device 350 is useful for performing, for example, multiplexed homogeneous assays or combinatorial synthesis.

In the embodiment shown in FIGS. 18A–18C, membrane valves were provided separate from associated mixing chamber valves to facilitate observation or analysis of the contents of the mixing chambers. Since neither the latex membrane comprising the fifth layer 355 nor the porous vent material of the twelfth layer 362 were optically clear, separating the membrane valves from the mixing chambers and providing windows through the twelfth layer 362 permitted an optically clear path to the mixing chambers to be maintained from below. Additionally, in certain applications it may be desirable to prevent evaporation of the resulting mixtures. Isolating the membrane valves (which permit evaporation) from the mixing chamber permits the channels connecting the membrane valves and mixing chambers to be sealed (such as by localized heat-sealing) to encapsulate the contents in the mixing chambers, thereby preventing their evaporation.

In further embodiments, microfluidic synthesis devices having high component densities may be constructed. For example, combinatorial mixers may be constructed in various formats and densities, including but not limited to formats such as: 8, 16, 24, or 64 mixing chambers within a square device having a side length of 2-¼ inches (having mixer densities ranging from 1.6 to 12.6 chambers/in$^2$, or 0.24 to 1.93 chambers/cm$^2$); 256 mixing chambers within a square device having a side length of 2-⅞ inches (having a mixer density of 31 chambers/in$^2$, or 4.7 chambers/cm$^2$); 96, 384, or 1536 mixing chambers within an area of 8 cm×12 cm (having mixer densities ranging from 1 to 16 chambers/cm$^2$, or 6.5 to 105 chambers/in$^2$). Referring to FIGS. 19A–19B, an array of 256 mixers was constructed in a single 5-layer square device 400 measuring 2-⅞ inches on each side. FIG. 19A provides an exploded view of the five layers, and FIG. 19B is a top view of the assembled device 400. Although a similar device could be constructed to receive sixteen fluidic inlets along each axis, the particular device depicted in FIGS. 19A–19B is configured to accept sixteen separate fluidic inlets 406 along one axis and eight separate fluidic inlets 407 along the other. This configuration results in two mixing chambers for each fluidic combination to provide intentional redundancy on the device. Such redundancy may be desirable to confirm synthesis results and/or reduce systematic error. The first layer 401 serves as a cover; the second layer 402 defines sixteen peripheral apertures 414 each along two sides of the layer, and sixteen linear channels 415 each having sixteen chambers 416; the third layer 403 defines sixteen peripheral vias 412 each along two sides of the layer 403, and 256 slits 413 to permit fluidic exchange between chambers 416 and 410 on the second and fourth layers 402, 404; the fourth layer 404 has sixteen channels 409 each having sixteen chambers 410, with eight peripheral apertures 411 each along two sides of the layer 404 for dividing each corresponding inlet stream in half; and the fifth layer 405 defines sixteen fluidic inlet ports 406 along two sides and eight fluidic inlet ports 407 along the remaining sides. In operation, fluids are introduced to the 256 chambers on the second and fourth layers 402, 404 and are prevented from mixing by the intermediate third layer 403. A pressure differential can then be applied to force fluid through the slits 413 in the third layer 403 to induce diffusion between the plugs. Two samples each of 128 different mixtures are formed. Alternatively, the device 400 may be deformed to cause the fluids to mix. Other methods of rupturing the slits may be used.

Microfluidic Reactors

Various microfluidic tools disclosed herein may be combined in complex microfluidic devices, for example, to perform synthesis reactions on a microfluidic scale. For example, FIGS. 20A–20B illustrate a five-layer synthesis device 420 according to one embodiment having a mixer and a long composite reactor channel. FIG. 20A is an exploded view of the five layers, and FIG. 20B is a top view of the assembled device 420. Preferably, the first layer 421 is a substrate; the second layer 422 defines segments 426 of the reactor channel and mixer elements 427; the third layer 423 defines vias 428 for the composite reactor channel along with a via 429 and a slit 430 for the mixer; the fourth layer 424 defines further segments 431 of the composite reactor channel; and the fifth layer 425 defines two inlet ports 432 and an outlet port 434. Various materials and construction methods may be to construct the device 420, although working devices embodying the design of FIGS. 20A–20B have been advantageously composed of layers of low-density polyethylene (LDPE) and ultra-high molecular weight polyethylene (UHMW PE) layers bonded together by heat-sealing using a conventional laminating machine. The resonance time is determined by the dimensions of the reactor channel and the pumping speed. For instance, the reaction time can be doubled by lowering the pumping speed by half or making the length of the reactor channel twice as long.

The device 420 of FIGS. 20A–20B was utilized to perform several different chemical reactions. Reactions performed in devices according to the design of FIGS. 20A–20B include: Tollen's Test for Aldehydes (depositing silver in the reactor channel); acid/base reactions such as reduction of methylene blue dye (testing for the presence of glucose); Diels-Alder reaction; and urethane formation. A more robust Wittig reaction was also performed in the device 420. In operation, two clear (liquid) streams containing the reactants were introduced to the device 420 via the inlet ports 432. The two streams came into contact in the second layer 422 by way of a mixer 427 (described herein in further detail) having a slit 430 in the third layer 423. Dark pink coloration due to formation of the ylid intermediate was observed a short distance downstream of the slit mixer 427, with colored intermediate entity of the Wittig reaction continuing to appear in the composite reactor channel but fading in color as the intermediate was converted to the olefinic product. The flow rates of the reactants were adjusted to complete the Wittig reaction within the device 420 so that only clear final products were observed at the outlet port 434. Surprisingly, observation of the microfluidic Wittig and Diels-Alder reactions revealed that the reactions required substantially shorter periods of time to go to completion compared with their execution in macrofluidic volumes.

Filter regions may be incorporated into microfluidic devices, such as to assist in performing synthesis or to promote analytical separation. For example, FIGS. 21A–21B illustrate a five-layer microfluidic device 440 for according to one embodiment having two mixers for mixing three fluid streams, two interference-fit filters, and a long composite reactor channel. FIG. 21A is an exploded view of the five layers, and FIG. 21B is a top view of the assembled device 440. Various materials may be used for the layers of the device 440. The first layer 441 serves as a cover. The second layer 442 defines a first channel 448 supplying fluid to a first filter 446, segments of a reactor channel 449 downstream of the first filter 446, and a second channel 450 supplying fluid to a second filter 447. The third layer 443 defines a via 451 for delivering fluid to the first channel 448, two mixer apertures 452, filter inlet apertures 453, and numerous peripheral vias 454 for connecting channel segments 449, 455, in the second and fourth layers 442, 444. The fourth layer 444 defines a via 456 for delivering fluid to the first channel 448, two pre-mixing channels 457 for supplying fluids to the mixer apertures 452, channel segments 455, and chambers 458 for holding filter elements 446, 447. Finally, the fifth layer 445 defines three fluidic inlet ports 459 and one fluidic outlet port 459A. In operation, three fluids are introduced to the device 450 through the inlet ports 459. The first fluid is provided to the first channel 448 in the second layer 442. The second and third fluids are conveyed to the mixer apertures 452, which are configured as slits, by way of the pre-mixing channels 457. Within the first channel 448, mixing and reaction between the three fluids are initiated. The mixture is transported to the first filter 446, which is used to remove insoluble impurities and/or precipitants from the reactants. Following the first filtration step, the reacting mixture travels through the channel segments 449, 455 and peripheral vias 454 forming the composite reaction channel. At the outlet of the reactor, the products flow through the second filter 447 to collect products of the reaction. The second filter 447 may be used, for example, to collect a precipitate if the reaction product is a solid, or the second filter 447 can have binding moieties on the surface to be used as an affinity filter if the reactants remain solubilized in the solution. With precipitate or other products removed from the product mixture, the remaining liquid exits the device through the outlet port 459A. A device 440 according to FIGS. 21A–21B was constructed and used to demonstrate a precipitation and filtration sequence using enzymatic resolution of a racemic amino acid (such as acylase-mediated resolution of phenylalanines wherein the resolved amino acid precipitates from the solution and is filtered out to be recovered at a later stage). In an alternative embodiment, catalysts may be substituted for (or combined with) one or both of the filters 446, 447 illustrated in FIGS. 21A–21B.

Further embodiments may utilize one or more diverters. For example, FIGS. 22A–22B illustrate a five-layer microfluidic device 460 according to an embodiment having two primary inlet ports 466, mixing regions 467, 477, a reactor channel 468, a primary outlet 469, a sampling/quenching port 470, a diverter region 472, a diverter channel 474, a shutoff valve 473, and a secondary outlet port 471 downstream of the diverter channel 472. FIG. 22A is an exploded view of the five layers 461–465, and FIG. 22B is a top view of the assembled device 460. Both the diverter region 472 and the shutoff valve 473 can be actuated by an external source, such as by an external physical piston (not shown) contacting the regions 472, 473. In operation, however, the diverter region 472 is designed to be normally shut (not diverting; fluid bypasses by flowing around the depressed portion of device layer 461 at diverter region 472 and continues to the primary outlet 469), and the shutoff valve 473 is designed to be normally open. These normal states are accomplished by applying pressure to the diverter 472 and not applying pressure to the shutoff valve 473. Initial operation of the device 460 is similar to that of the device 420 illustrated in FIG. 20A–20B. Two reactants are supplied to the device 460 through the primary inlet ports 466 and combined in the mixing region 467. The mixing region 467 may be any structure that sufficiently mixes the two fluids and preferably comprises an overlap portion 467A of channel 478 that communicates with reactor channel 468 through the a slit 467B in device layer 463. Thereafter, the device 460 may be utilized to divert a sample by activating the diverter 472 and shutoff valve 473, by releasing pressure to the diverter 472 and applying pressure to the valve 473. Sealing is established within the diverter region 472 and the valve region 473 by depressing the top stencil layer 461 just above the diverter region 472 and valve region 473, thereby deforming the stencil layer 461 to seal against the diverter aperture 475 and valve aperture 476 in layer 463.

Two fluids may be provided to the device 460 to interact with one another. When a sample is desired, the shutoff valve 473 is closed, and the diverter 472 is opened, while simultaneously introducing a flow of a fluid or gas that is desired to be mixed at mixing region 477 (which may be any mixing structure and is preferably a slit mixer structure similar to that described above with respect to mixing region 467) with the sample (e.g. a quenching agent, an analyte, an inert carrier) to direct the sample through the diverter channel to the secondary (diverter) outlet port 471. Once a sample is taken, the chip can be returned to its normal operation by shutting diverter 472 and opening the shutoff valve 473.

In one embodiment, both the diverter valve 472 and shutoff valve 473 are controlled by externally-applied pressure, according to FIGS. 22C–22D, which illustrate cross-sectional views of valve portions of the device 460. Actuation methods include, but are not limited to, pneumatic, hydraulic, electro-mechanical, magnetic and electro-static actuation means. Furthermore, actuation methods may be modified by the addition of material layers or providing actuation chambers within the device.

Microfluidic synthesis devices as described herein may be used to perform a wide variety of chemical and biological syntheses. Classes of chemical syntheses that may be performed on the devices include: (1) Amide bond forming reactions (such as formation of sulfonamide, guanidine, phosphoramide, thiourea, urea, and urethane, and amine acylation); (2) Aromatic substitution reactions (such as aryl-aryl coupling, Friedel-Crafts acylation and alkylation, nucleophilic substitution, and metal-promoted coupling); (3) Condensation reactions (such as formation of acetal, enamine, and imine, and Aldol and Claisen condensation and variations thereof); (4) Cycloaddition reactions (such as [2+2] cycloaddition, Diels-Alder, and 1,3-Dipolar addition); (5) Polar addition and elimination reactions (such as Grignard reactions, Michael addition, hydration, halogenation, and dehydration); (6) Heterocycle forming reactions (such as formation of benzimidazole, hydantoin, piperidine, imidazole, indole, iosxazole, lactam, and pyrazole); (7) Olefin forming reactions (such as elimination, Wittig and related reactions); (8) Oxidation reactions (such as those involving the use of transition metal oxidants, PCC, peroxide, and oxidations using oxygen/air/ozone/nitric acid); (9) Reduction reactions (such as dissolving metal, catalytic hydrogenation, and metal hydride); and (10) other reactions and processes including enzymatic resolutions, asymmetric synthesis and resolution using chiral templates or catalysts, and other reactions using functional group manipulation as applied to multi-step synthesis.

Thermal Exchange Utility

If it is desired to provide thermal exchange utility, heating and/or cooling elements may be used in conjunction with a microfluidic device to conduct heat to or from a microfluidic device or regions thereof. Such heating/cooling elements can be integrated into the microfluidic device or provided as external components that come into contact with the device. In a preferred embodiment, one portion of a heating device composes a portion of a microfluidic channel or chamber. Referring to FIG. 23A, a cross-section of a portion of microfluidic device is shown. The portion is composed of three stencil layers 500–502 and a heating element 503, which form a inlet/outlet channel regions 504 and a chamber 505. The top surface of the heating element 503 forms the bottom surface of the chamber 505. When the element 503 is heating, energy is transferred (by mechanisms including conduction and natural convection) into fluid occupying the chamber 505. In another preferred embodiment, the heating element is external to (i.e. not part of) the microfluidic device. Referring to FIG. 23B, a cross-section of a portion of microfluidic device is shown. The device portion is composed of three stencil layers 510–512, which form an inlet/outlet channel region 513 and a chamber 514. The top surface of a microfluidic heating element 515 is brought into contact with the microfluidic device. When the heating element 515 is activated, energy is conductively transferred through the bottom stencil layers 512 into the fluid occupying the chamber 514. The composition of stencil layer 512 can be tailored to optimize the thermal transfer rate between the heating element 515 and the chamber 514. In certain embodiments, stencil layers including layer 512 may be fabricated from metal to optimize thermal transfer. In other embodiments, thermally conductive polymers or other thermally conductive materials can be used. In certain embodiments, stencil layer 512 can be composed of materials that are poor thermal conductors in order to moderate the heat transfer. In other embodiments, the thickness of the stencil layer can be altered to change the thermal properties. In such an embodiment, a significant portion of the heat supplied by the element 515 may be conducted laterally, along the horizontal plane of stencil layer 512.

In one embodiment, an upper stencil layer 500 may also be composed of a thermally conductive material. A heat sink (not shown) may be added along the top surface of the device, above stencil layer 500. In this manner, utilizing a heater and/or heat sink, a thermal gradient can be generated within the microfluidic chamber 526. In this or other embodiments, a microfluidic device or portions thereof may be thermally cycled, such as is useful to perform processes such as PCR.

In certain embodiments, it may be desirable to heat a microfluidic device in only a localized region. Referring to FIG. 23C, a cross-section of a portion of microfluidic device is shown. The portion is composed of five stencil layers 520–524, which form an inlet/outlet channel region 525 and a chamber 526. Stencil layer 524 is composed of a substantially thermally conductive material so as to maximize the thermal conduction between the top surface of the heating element 525 and fluid in the chamber 524. Stencil 522 is composed of a material which is substantially non-conductive promote the flow of energy into the chamber 526. In this embodiment, horizontal (lateral) heat transfer within the layers of the device is minimized.

In another preferred embodiment, a conducting material is placed within a microfluidic chamber so that voltage may be applied through the conducting material to resistively heat the conducting material, and thus the contents of the chamber. The size and composition of the conductive material can be adjusted so as to provide the desired level of resistive heating for a given application. Temperature sensing elements may also be used to monitor temperature within a device and/or to enable feedback control of a fluid process.

Heating and cooling elements useful within devices as described herein may come in various forms, including but not limited to electric heaters, thermoelectric heaters and coolers (Peltier devices), resistive heaters, capacitively coupled RF heaters, heat sinks, fluidic circuit heaters, heatpipes, chemical heaters, and other types.

In certain embodiments, fluid within a microfluidic device is heated using an off-board heating mechanism. In some embodiments the heating mechanism does not come into physical contact with the microfluidic device. For example, electromagnetic radiation may be used to heat fluid within the device. In a preferred embodiment, the radiation is within the microwave spectrum. In another preferred embodiment, the radiation is within the infrared spectrum. Alternatively, an external heating mechanism may contact the device, including a sonic (preferably ultrasonic) heater used to induce heating of a fluid.

In an embodiment providing catalytic utility, portions of a microfluidic device are composed of one or more catalyst materials. The catalysts can be used to increase the reaction kinetics of a given reaction, or to drive a synthetic reaction towards a specific product.

Microfluidic Devices with Catalyst Materials

Various methods may be used to introduce catalyst materials into microfluidic devices. Various configurations include packed beds of catalyst materials, layers of catalyst materials, and depositions or coatings on targeted surfaces.

In a preferred embodiment, a microfluidic device comprises a stencil layer formed from catalyst materials. Referring to FIG. 24A, a cross-section of a portion of microfluidic device is shown. The device portion is composed of four stencil layers 600–603, which form an inlet/outlet channel region 604 and a chamber 605. Stencil layer 603 is composed of a catalyst material so that the top surface of the catalyst material forms the bottom portion of chamber 605. Fluid can be injected through the chamber 605 so that the fluid contacts the catalyst 603.

Importantly, utilizing methods provided herein for constructing microfluidic devices, various parameters may be manipulated to optimize the interaction of molecules and atoms in the solution with a catalyst surface. For example, the height of the microfluidic channel or chamber where the catalyst is located may be varied, the surface area and position of catalyst material may be varied, and the flow rate of fluid within the device may be controlled. In the embodiments shown, the height of the channel in the region near the catalyst is relatively small, so that while the fluid is located near the catalyst, Brownian motion (or diffusional motion) will bring substantially all of the molecules in contact with the surface at least once during their resonance time. Alternatively, the height of the channel can be adjusted so that for a given resonance time a known percentage of the molecules in solution will come into contact with a catalyst surface.

In another preferred embodiment, the catalyst material is positioned within a channel subject to microfluidic flow. Referring to FIG. 24B, a cross-section of a portion of microfluidic device is shown. The device portion is composed of three stencil layers 610–612, which form an inlet/outlet channel region a chamber 614. A catalyst material 615 is located within the flow chamber 614. In a preferred embodiment, the catalyst 615 is free floating within the chamber. In other embodiments, the catalyst 615 may be adhered in some manner, for instance using adhesive, to a stencil layer such as the bottom stencil layer 612.

In another preferred embodiment, catalyst material is provided in powder or bead form. Referring to FIG. 24C, a cross-section of a portion of microfluidic device is shown. The device portion is composed of two stencil layers 620, 621 and a porous plug 623 that form a flow channel region 622. The filter 623 is composed of a material that allows fluid to flow but blocks the flow of the catalyst material 624. In this embodiment, the porous plug 623 may further function as a filter to trap elements flowing within the fluid. For example, a device was constructed from polyethylene stencil layers having a paper filter plug inserted into a channel during manufacture. A suspension of Pd/C in water was introduced into the device so that the filter trapped the suspended particles but allowed the water to pass. This resulted in a well-defined and stable catalytic region through which further reaction solutions were beneficially passed.

Another preferred embodiment is shown in FIG. 24D. In this embodiment, catalyst materials 633 are adhered to the top layer 634 of a stencil layer 631 along the boundary of a channel 632. The catalyst materials 633 may adhere to the surface 634 through intermolecular bonds or through the use of adhesives. Other adherence mechanisms may possibly be used. In some embodiments, the catalyst materials larger than certain regions of the microfluidic device are provided to advantageously lodge the catalyst materials within a region of the device. Other methods for placing catalyst materials within a microfluidic device may be used. For instance, a catalyst material may be entrained in liquid and flowed into a device as a slurry or solution, and the solution may be evaporated.

Catalysts that may be used with microfluidic devices as described herein include but are not limited to transition metals. Reactions types using the aforementioned catalysts include: ammination, aziridation, carbon-carbon bond formation, carbon-hetero atom bond formation, cyclization, cyclopropanation, decarbonylation, epoxidation, hydroboration, hydroformylation, hydrogenation, metathesis and oxidations. Microreactors embedded with a catalyst may furthermore serve a variety of purposes, including rapid generation valuable data such as, kinetic, thermodynamic, catalyst screening for optimum activity, selectivity and determining catalytic turnover.

Condensation Utility

In another embodiment, a microfluidic condenser is provided. This condenser can be used in a variety of ways, including as one component of a distillation device, a reflux device, or other types of devices used for performing synthetic reactions. Referring to FIG. 25A, a cross-section of a portion of microfluidic device is shown. The device portion is constructed from seven stencil layers 650–656. Stencil layer 652 is composed of a filter material that blocks the flow of the liquid to be used but is porous to gas. For example, Gore-Tex® may be used for the filter material. A check valve is provided downstream of the entry channel 660 to allow fluid to flow into the chamber 657 but not back out. Fluid is injected through the valve 660 into a fluidic chamber 657. Once the chamber is filled, a heating element 659 is activated. The output of the heating element 659 is tuned so as to bring the fluid in the chamber 657 above its boiling point. For example, a thermocouple or other temperature measuring device (not shown) may be integrated into the microfluidic device to provide feedback to the heating system for thermal control. The vapors created by the boiling process pass through the filter layer 652 into a condenser chamber 658 where the vapors condense back to liquid form. Other condenser configurations are possible. In certain embodiments, the layer 650 may act as a heat sink or cooling device to promote condensation. Alternatively, a heat sink or cooling device (not shown) can be added to the top surface of the device and cool chamber 658 by conduction through stencil layer 650. If external pressure sources and pressure-sealed chambers (not shown) are provided, then a thermal condensation process may be supplemented with or supplanted entirely by manipulating the pressure within the device.

Referring to FIG. 25B, a cross-section of a portion of microfluidic device is shown. The device portion is composed of five stencil layers 670–674. As in FIG. 25A, a valve region is located at the entry channel 675. Fluid is injected through the valve 675 into a fluidic chamber 676. Once the chamber 676 is filled, a heating element 678 is activated. Again, the fluid within the chamber 676 is heated to its boiling point. The vapors will pass through channel 681. The vapors condense in chamber 677, which is the collection chamber. In a preferred embodiment, the vapors condense on the upper surface 680 of chamber 677. In another preferred embodiment, a cooler device or heat sink 679 can be mounted to come into contact with one or more surfaces of the collection chamber 677 to enhance condensation.

Electrodes and Other Conductive Elements

In another embodiment, electrodes may be are placed in channels and/or chambers to perform, for example, detection and/or activation functions. Examples include electrophoresis, electrokinetic flow, electrochemical detection, impedance detection, capacitive detection, heating and measuring current or voltage. In examples of various electrode configurations, wires may be placed between stencil layers so as to protrude into channels, wires may be propagated within channels, or stencil layers may be fabricated from conductive foils. Additionally, stencil layers may be patterned with metallic film. In further embodiments, current can be passed through conductive elements disposed in a microstructure to induce heating within the microstructure. Thermocouples can be constructed within the microstructure using the conductive elements to detect thermal changes. Calorimetry can be performed in this manner. In addition, a magnetic field can be induced in a similar manner. This magnetic field can be used to detect certain phenomena or induce flow using magnetic particles.

Microfluidic Devices with Multiple Flow-through Fluid Process Regions

Microfluidic devices may include multiple flow-through fluid process regions for performing parallel processes such as syntheses and/or analyses. In embodiment, process regions are preferably in fluid communication with different sample inlet ports. Additionally, at least two fluid process regions are preferably in fluid communication with at least one common inlet, such as may be used to supply similar substances (e.g., reagents, mobile phase solvents, or solid materials) to different process regions. Multiple sample inlet ports may be used to supply similar or different samples to each fluid process region. In one embodiment, a microfluidic device may include first microfluidic splitting network for distributing at least a first substance supplied from a first common inlet among multiple branch channels, and may further include a second microfluidic splitting network for distributing at least a second substance supplied from a second common inlet among multiple branch channels. In one embodiment, any of the first splitting network and the second splitting network includes branch channels of different impedances. For example, any of the first splitting network and the second splitting network may include branch channels of different lengths. Any of the first splitting network and the second splitting network may be substantially filled with solid materials such as, but not limited to, packed particulate stationary phase (separation) material or packed catalyst materials such as beads. A convenient method for supplying solid materials to a microfluidic device is in the form of a slurry. If packed particulate material is used, then at least one porous material (e.g., a porous membrane) adapted to retain the packed particulate material within a microfluidic device is preferably provided. Preferably, the porous material has an average pore size that is smaller than the average particle size.

One or more mixing regions may be provided in fluid communication with any of the first splitting network and the second splitting network. Each mixing region is preferably a passive mixing region to minimize the need for mechanisms and/or external energy inputs such as sonic waves. For example, a mixing region may include a channel overlap region such as described previously herein, or in commonly assigned WIPO patent publication number WO 02/011888 entitled "Fluidic Mixer in Microfluidic System". In one embodiment, each mixing region of multiple mixing regions effects mixing of a first fluid and a second fluid in different proportions.

In a preferred embodiment, a microfluidic device includes multiple process regions adapted to subject similar samples or reagents to different process conditions in parallel, such as may be useful for methods development. In other words, parallel fluid process regions may be intended to perform differently. Examples of process conditions that may be varied among different process regions include, for example, fluid flow rate, fluid concentration, solid material type, and solid material surface area. Various methods for varying these process conditions include: providing active or passive flow control means to control fluid flow rates in specific fluid process regions; splitting and mixing supply fluids in different proportions upstream of the fluid process regions to control fluid concentration in specific fluid process regions; providing different particulate materials or coatings to different process regions during their fabrication; and providing process regions of different lengths/volumes or supplying particulate materials of different sizes to different process regions to provide different solid material surface areas. To provide maximum methods development utility, however, it would be particularly desirable to limit substantial variation among different process regions to only a single process condition in a particular device. Additionally, it would be desirable to utilize common fluidic inputs (e.g., solvents or reagents) to minimize the number of external fluid supply components such as pumps, degassers, pulse dampers, etc. Furthermore, it would be desirable to provide a device with passive flow regulation to reduce the dependence on potentially costly and trouble-prone active flow control device. Therein lies a challenge—namely, minimizing the variation in certain process conditions such as fluid flow rate between multiple process regions specifically designed to subject fluids flowing therethrough to differences in other process conditions—such as common fluid (e.g., solvent or reagent) concentration or the quantity, type, or density of solid material contained within each process region.

In one embodiment directed to methods development, a microfluidic device may include parallel fluid process regions in fluid communication with at least one common fluid input but having different effective lengths. A first example of a microfluidic methods development device including multiple fluid process regions with different effective lengths is provided in FIGS. 26A–26G. The device 710 includes six parallel fluid process regions 728A–728N divided into two groups of three process regions 728A–728C, 728D–728N, with each group of process regions having three process regions 728A–728C, 728D–728N of different effective lengths due to the presence of sample loading channels 754A–754N which serve to inject different samples at three different points along the length of the process regions 728A–728N. (Although FIGS. 26A–26G show the device 710 having six fluid process regions 728A–728N, it will be readily apparent to one skilled in the art that any number of fluid process regions 728A–728N may be provided. For this reason, the designation "N" is used to represent the last column 728N, with the understanding that "N" represents a variable and could represent any desired number of columns. This convention may be used elsewhere within this document.)

The device 710 may be constructed with nine device layers 711–719, including multiple stencil layers 712–718 and two outer or cover layers 711, 719. Press-fit (external) interconnects (not shown) to the device 710 may be provided with either gasketed or gasketless interfaces. Preferably, the device 710 is constructed with materials selected for their compatibility with chemicals to be used in the desired fluid process. Specifically, the device materials should be substantially non-absorptive of, and substantially non-degrading when placed into contact with, such chemicals. For example, if the device 710 is to be used for performing liquid chromatography, which may commonly employ chemicals such as water, methanol, ethanol, isopropanol, acetonitrile, ethyl acetate, dimethyl sulfoxide, and mixtures thereof, then suitable device materials include polyolefins such as polypropylene, polyethylene, and copolymers thereof. Beyond chemical compatibility, these materials exhibit the further benefit of being substantially optically transmissive so as to aid in performing quality control routines (including checking for fabrication defects) and in ascertaining operational information about the device 710 or its contents. In one example, each device layer 711–719 may be fabricated from 7.5 mil (188 micron) thickness "Clear Tear Seal" polypropylene (American Profol, Cedar Rapids, Iowa).

Broadly, the device 710 includes various structures adapted to distribute particulate-based slurry material among multiple fluid process regions 728A–728N), to retain the solid particulate material (e.g., catalyst material or chromatographic separation material such as, for example, silica-based particulate material to which hydrophobic carbon-based functional groups have been added) within the device 710, to distribute common fluids (e.g., solvents or reagents) among the fluid process regions 728A–728N, to receive samples, to convey fluid process effluent streams from the device 710, and to convey a waste stream from the device 710.

Preferably, the fluid process regions 728A–728N are adapted to contain solid materials. One difficulty associated with prior microfluidic devices has been retaining small particulate matter within separation columns during operation. The present device 710 overcomes this difficulty by the inclusion of a downstream porous frit 731, three sample loading porous frits 759A–759C, a common fluid inlet frit 796 and a common fluid waste frit 785. Each frit 731, 759A–759C, 785 (and frit 777) may be fabricated from a strip of porous material, e.g., 1-mil thickness Celgard 2500 polypropylene membrane (55% porosity, 0.209×0.054 micron pore size, Celgard Inc., Charlotte, N.C.) and inserted into the appropriate regions of the stacked device layers 711–719 before the layers 711–719 are laminated together. The average pore size of the frit material should be smaller than the average size of the stationary phase particles. Preferably, the frit material has a similar surface energy to that of the adjacent device layers and an adhesiveless bonding method such as one of the methods described previously herein (or in commonly assigned U.S. Patent Application Publication No. 2003/0150792 (Ser. No. 10/256,505, filed Sep. 27, 2002), which is hereby incorporated by reference) is used to interpenetrably bond the device layers 711–719 (and frits 731, 759A–759C, 785, and 777) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and fluids (e.g., solvents, reagents, and/or samples) to be supplied to the device 710.

A convenient method for packing solid material within the separation channels 728A–728N is to provide it in the form of a slurry (i.e., particulate material mixed with a suitable solvent; acetonitrile may be used with silica-based chromatographic separation materials). Slurry is supplied to the device 710 by way of a slurry inlet port 720 and channel structures defined in the sixth through eighth device layers 716–718. Specifically, the eighth layer 718 defines a slurry via 720A, a common fluid waste channel segment 736, two small forked channels 726A and 726B and six column outlet vias 730A–730N. The seventh device layer 717 defines a slurry via 720B, a large forked channel 724 and the (solid-containing) separation channels 728A–728N. The sixth device layer 716 defines a slurry channel 722 in fluid communication with the large forked channel 724 and the slurry via 720B defined in the seventh layer 717. In the aggregate, the slurry channel 722, large forked channel 724, and two small forked channels 726A and 726B form a slurry distribution network that communicates slurry from a single inlet (e.g., slurry inlet port 720) to six fluid process regions 728A–728N (e.g., columns or reactors 728A–728N, depending on the nature of the solid material contained therein). The slurry may be added by stirring the solid material in a carrier solvent (e.g. isopropanol) so that a suspension is formed, and then pumping this continually stirred suspension into the slurry inlet port at a fixed pressure (e.g., 350 psi). Alternatively, various packing methods such as provided in commonly assigned U.S. Patent Application Publication No. 2003/0150806 (Ser. No. 10/366,985, filed Feb. 13, 2063) (hereby incorporated by reference) may be used.

Upon addition of particulate-containing slurry to the fluid process regions 728A–728N, the solid material is retained within the fluid process regions 728A–728N by one downstream porous frit 731, three sample loading porous frits 759A–759C, one common fluid inlet frit 796 and one common fluid waste frit 785. After solid material is packed into the fluid process regions 728A–728N, a sealant (preferably substantially inert such as UV-curable epoxy) may be added to the slurry inlet port 720 to prevent the packed solids within the fluid process regions 728A–728N from unpacking during operation of the device 710. The addition of sealant should be controlled to prevent blockage of the waste channel segment 736.

As an alternative to using packed particulate material, porous monoliths may be used as the solid functional material. Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used. Numerous recipes for preparing monolithic columns suitable for performing chromatographic techniques are known in the art. In one embodiment a monolithic ion-exchange column may be fabricated with a monomer solution of about 2.5 ml of 50 millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide.

To prepare the device 710 for operation, one or more common fluids (such as mobile phase solvents) may be supplied to the device 710 through a common fluid inlet port 790 defined in the ninth layer 719. Multiple common fluids may be pre-mixed upstream of the device 710 using a conventional micromixer. The common fluids are supplied through channel segment 791 in layer 713 to a common fluid distribution network including one large forked channel 792 in layer 714, two small forked channels 793A and 793B in the fifth layer 715, and six common fluid channel segments 794A–794N defined in the fourth layer 714. Each of the six common fluid channel segments 794A–794N is in fluid communication with one of the six fluid process regions 728A–728N by way of a different via 795A–795N of six vias 795A–795N defined in the fifth layer 715, a common fluid inlet frit 796, and a different via 797A–797N of six vias 797A–797N defined in the sixth layer 716. This common fluid distribution network is also used to supply functional common fluid(s) during operation of the device 710, such as following the loading of samples into the sample inlet ports 752A–752N of the device 710.

While the bulk of the common fluid that is supplied to each fluid process regions 728A–728N travels downstream through the fluid process regions 728A–728N, a small split portion of each travels upstream through the fluid process regions 728A–728N in the direction of the waste port 782. The split portions of common fluid from each fluid process region 728A–728N that travel upstream are consolidated into a single waste stream that flows through the slurry distribution network comprising the two small forked channels 726A and 726B, large forked channel 724, and slurry channel 722, then through via 734, the short waste segment 736, vias 738A and 738B, frit 785, via 738C, a waste channel 784, to the waste port 782 to exit the device 710. The purpose of providing both an upstream and downstream path for each fluid process region 728A–728N is to allow the removal of air bubbles from the device 710 during device preparation.

The first layer 711 of the device 710 defines multiple sample inlet ports 752A–752N that permit samples to be supplied to sample loading channels 750A–750N defined in the second layer 712. The third through sixth layers 713–716 define a sample loading network designed to push samples onto each of the six fluid process regions 728A–728N. Each sample loading channel 750A–750N is in fluid communication with a different sample loading port 752A–752N. The common fluid (which may be a mixture of two or more fluids such as solvents) flows from the inlet port 738 in the ninth layer 719, through vias in the fourth through eighth layers 714–718, and into the large common fluid channel 740 defined in the third layer 713. The common fluid then flows to the large forked channel 742 in the fourth layer 714, through the two smaller forked channels 744A–744B in the fifth layer 715, through the vias 746A–746N in the fourth layer 714, through the frit 777, and through the vias 748A–748N in the third layer 713 that connect to the sample loading channels 750A–750N defined in the second layer 712. While the frit 777 technically does not function to retain any solid material within the device 710, it may be fabricated from the same material as the sample loading frits 759A–759C, the common fluid inlet frit 796, and the common fluid waste frit 785, which do retain solid material within the fluid process regions 728A–728N. The common fluid that flows into the sample loading channels 750A–750N defined in the second layer 712 then carries the samples into the narrow loading channels 754A–754N defined in the third layer 713, through vias 756A–756F defined in the fourth and fifth layers 714 and 715, through the sample loading frits 795A–795C, through vias 756A–756F defined in the sixth layer 716 and onto each of the six fluid process regions 728A–728N defined in the seventh layer 717. To prepare the device 710 for sample loading, common fluid flow is temporarily interrupted, an external interface (not shown) previously covering the sample loading ports 752A–752N is opened, and samples are supplied through the sample ports 752A–752N into the sample loading channels 750A–750N. The frit 777 and the frits 759A–759C provide substantial fluidic impedance that prevents fluid flow through the frits 777, 759A–759C at low pressures. This ensures that the samples remain isolated within the sample loading channels 750A–750N during the sample loading procedure. Following sample loading, the sample loading ports 752A–752N are again sealed (e.g., with an external interface) and common fluid flow is re-initiated to carry the samples onto the fluid process regions 728A–728N defined in the seventh layer 717. The common fluid flow through the sample loading network is then again interrupted, and common fluid is supplied through the common fluid distribution network including channel segment 791 in layer 713, the large forked channel 792 in layer 714, two small forked channels 793A and 793B in layer 715, and six common fluid channel segments 794A–794N in layer 714.

Figure 26E:
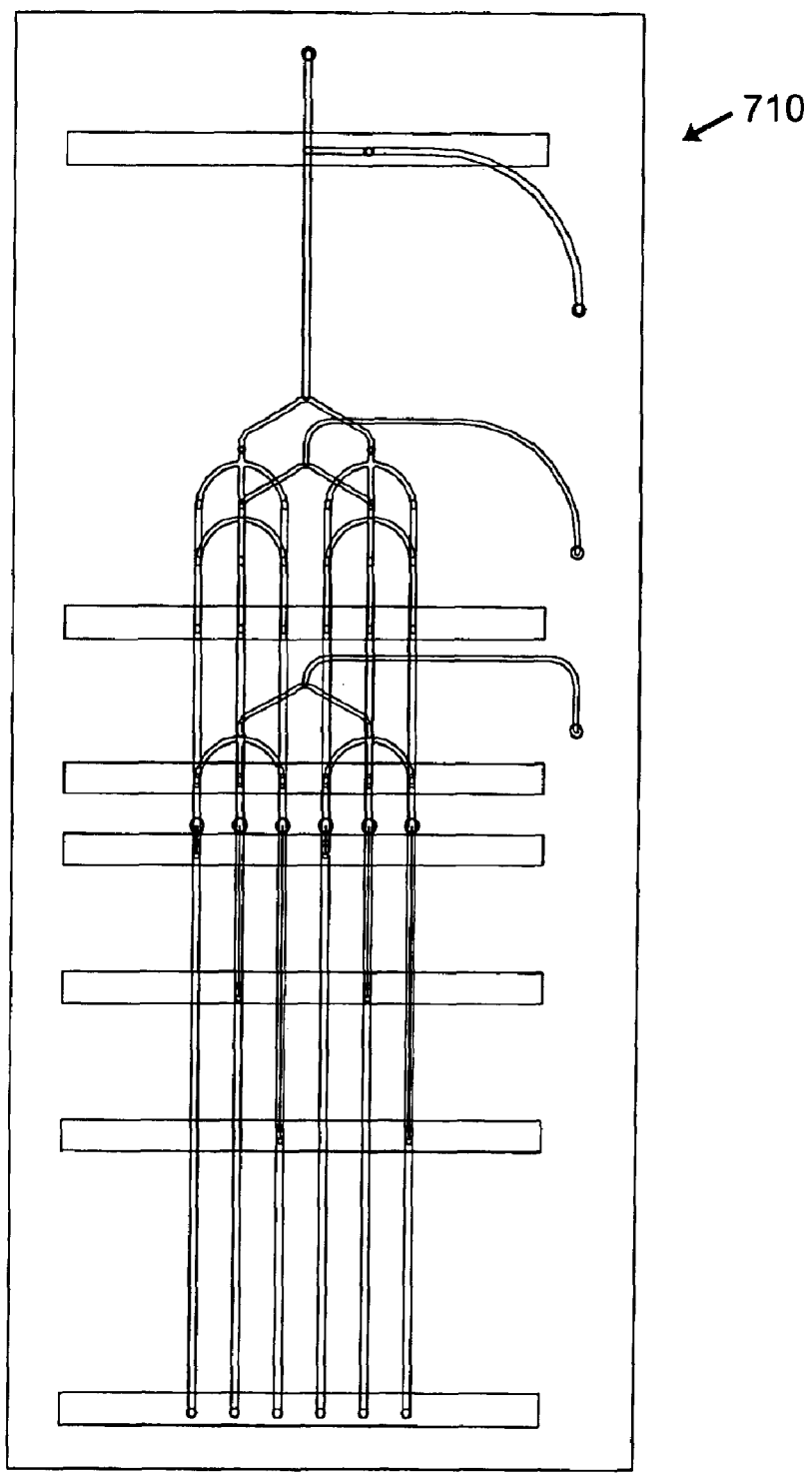
FIG. 26E is a top view of the assembled device of FIGS. 26A–26D.

FIG. 26E shows the top view of the assembled device. FIG. 26F shows the slurry distribution network 710D (comprising slurry channel 722, common fluid waste channel segment 736, common fluid waste channel 784, large forked channel 724, two small forked channels 726A and 726B, six fluid process regions 728A–728N and six fluid process region column outlet vias 730A–730N). FIG. 26G shows the common fluid distribution network 710E (comprising channel segment 791, large forked channel 792, two small forked channels 793A and 793B, and six common fluid channel segments 794A–794N), and the sample loading network 710F (comprising common fluid channel 740, large forked channel 742, two smaller forked channels 744A–744B, sample loading channels 750A–750N, sample loading ports 752A–752N, and narrow loading channels 754A–754N).

If the device 710 is to be used for chromatographic separation utility, then either isocratic separation (in which the mobile phase composition remains constant) or, more preferably, gradient separation (in which the mobile phase composition changes with time) may be performed. If multiple fluid process regions or separation columns 728A–728N are provided in a single integrated device (such as the device 710) and the makeup of the common fluid or mobile phase is subject to change over time, then at a common linear distance from the common fluid/mobile phase inlet it is desirable for the common fluid/mobile phase to have a substantially identical composition from one fluid process region/separation column 728A–728N to the next. This is achieved with the device 710 due to two factors: (1) volume of the path of each (split) common fluid/mobile phase solvent substream is substantially the same to each fluid process region/separation column 728A–728N; and (2) each flow path downstream of the fluidic (common fluid/ mobile phase solvent and sample) inlets is characterized by substantially the same impedance. The first factor, substantially equal substream flow paths, is promoted by design of the mobile phase distribution network 710E (even though the sample loading network 710F has narrow loading channels 754A–754N of various lengths, which will inject the samples from the sample loading ports 752A–752N onto each of the six fluid process regions/separation columns 728A–728N at a different points along the length of the fluid process regions 728A–728N). The effect of the different sample injection points along the length of the fluid process regions 728A–728N is to vary the effective lengths of the fluid process regions 728A–728N—that is, the lengths of the fluid process regions 728A–728N subject to interaction with the samples. The second factor, substantial equality of the impedance of each fluid process region/separation column 728A–728N, is promoted by both design of the fluidic device 710 (including the slurry distribution network 710D) and the fabrication of multiple fluid process regions/ separation columns 728A–728N in fluid communication (e.g., having a common outlet) using the slurry packing method disclosed herein. Where multiple fluid process regions/separation columns 728A–728N are in fluid communication with a common outlet, slurry flow within the device 710 is biased toward any low impedance region. The more slurry that flows to a particular fluid process region 728A–728N during the packing process, the more solid material is deposited to locally elevate the impedance, thus yielding a self-correcting method for producing substantially equal impedance from one fluid process region 728A–728N to the next.

In another embodiment directed to methods development, a microfluidic device may include parallel fluid process regions in fluid communication with at least one common fluid input but containing different solid materials. A first example of such a device is provided in FIGS. 27A–27G.

The device 810 includes six parallel fluid process regions 828A–828N, including two groups of three process regions 828A–828C, 828D–828N, with each group containing different functional solid materials. Various types of functional solid materials may be used, such as stationary phase separation materials or catalyst materials, depending on the desired functionality of the device 810.

The device 810 is constructed with nine device layers 811–819, including multiple stencil layers 812–818 and two outer or cover layers 811, 819. Press-fit (external) interconnects (not shown) to the device 810 may be provided with either gasketed or gasketless interfaces. The device 810, its materials of construction, and methods for its manufacture may be the same as the previous device 710 described in connection with FIGS. 26A–26G.

Broadly, the device 810 includes various structures adapted to distribute solid (e.g., slurry) material among multiple fluid process regions 828A–828N, to retain the solid material within the device 810, to distribute one or more common fluids or a mixture thereof among the fluid process regions 828A–828N, to receive samples, to convey effluent streams from the device 810, and to convey a waste stream from the device 810.

Preferably, the fluid process regions 828A–828N are adapted to contain solid material, such as by including porous frits; namely, a downstream porous frit 831, a sample loading porous frit 859, and a common fluid waste frit 884. Each frit 831, 859, and 884 (and frits 877A–877N) may be fabricated from a strip of porous material, e.g., 1-mil thickness Celgard 2500 polypropylene membrane (55% porosity, 0.209×0.054 micron pore size, Celgard Inc., Charlotte, N.C.) and inserted into the appropriate regions between the various stacked device layers 811–819 before the layers 811–819 are laminated together. The average pore size of the frit material should be smaller than the average size of the solid particles. Preferably, an adhesiveless bonding method such as one of the methods described or referred to previously herein is used to interpenetrably bond the device layers 811–819 (and frits 831, 859, 884, and 877A–877N) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 810.

A convenient method for packing solid material within the separation channels 828A–828N is to provide it in the form of a slurry (i.e., particulate material mixed with a suitable solvent; e.g., acetonitrile may be used in conjunction with silica-based chromatographic separation material). Slurry is supplied to the device 810 by way of slurry inlet ports 820A, 820B and channel structures defined in the sixth through eighth device layers 816–818. Specifically, the eighth layer 818 defines slurry vias 821A, 821B, common fluid waste channel segments 836A, 836B, two small forked channels 826A and 826B and six fluid process region outlet vias 830A–830N. The seventh device layer 817 defines slurry vias 822A, 822B, and the (solid-containing) fluid process regions 828A–828N. The sixth device layer 816 defines slurry channels 823A, 823B in fluid communication with the small forked channels 826A and 826B (by way of two vias 825A, 825B defined in the seventh layer 817) and the slurry vias 822A, 822B defined in the seventh layer 817. In the aggregate, the first slurry channel 823A and small forked channel 826A form a slurry distribution network that communicates slurry from the first slurry inlet 820A to a first group of three fluid process regions 828A–828C. In addition, a separate slurry distribution network is formed by a second slurry channel 823B and small forked channel 826B that communicates slurry from the second slurry inlet 820B to the second group of three fluid process regions 828D–828. Each slurry distribution network may be filled with a different or similar type of packing material. Upon addition of particulate-containing slurry to the fluid process regions 828A–828N, the solid material is retained within the fluid process regions 828A–828N by one downstream porous frit 831, one sample loading porous frit 859, and one common fluid waste frit 884. After solid material is packed into the fluid process regions 828A–828N, a sealant (preferably substantially inert such as UV-curable epoxy) may be added to the slurry inlet ports 820A, 820B to prevent the solid material contained within the fluid process regions 828A–828N from unpacking during operation of the device 810. The addition of sealant should be controlled to prevent blockage of the common fluid waste channel segments 836A, 836B. As before, porous monoliths may be used within the fluid process regions 828A–828N as an alternative to packed solid (particulate) matter.

The first layer 811 of the device 810 defines multiple sample ports/vias 852A–852N that permit samples to be supplied to sample loading channels 850A–850N defined in the second layer 812. The third through sixth layers 813–816 define a common fluid distribution network designed to push samples into each of the six fluid process regions 828A–828N. Each sample-loading channel 850A–850N is in fluid communication with a different sample loading port 852A–852N. The common fluid (which may be a mixture of two or more fluids) flows from the common fluid inlet port 890 defined in the ninth layer 819, through vias in the fourth through eighth layers 814–818, and into the large common fluid channel 891 defined in the third layer 813. The common fluid then flows to the large forked channel 892 defined in the fourth layer 814, through the two smaller forked channels 893A–893B defined in the fifth layer 815, through the frit 877A, into six common fluid channel segments 894A–894N defined in the fourth layer 814, through the frit 877B, into six common fluid channel segments 895A–895N defined in the fifth layer 815, through the frit 877C, into six common fluid channel segments 896A–896N defined in the fourth layer 814, through the frit 877D, and into six common fluid channel segments 897A–897N defined in the fifth layer 815. The common fluid then flows through the frit 877N, through vias 847A–847N defined in the fourth layer 814, through the vias 848A–848N defined in the third layer 813 and into the sample loading channels 850A–850N defined in the second layer 812. While the frits 877A–877N technically do not serve to retain any packing material within the device, they may be fabricated from the same material as the sample loading frit 859, the outlet frit 831 and the solvent waste frit 884, which do serve to retain packing material within the fluid process regions 828A–828N. The purpose of the frits 877A–877N is to elevate the impedance to each fluid process region 828A–828N, to reduce differences in fluid impedances between fluid process regions containing different solid particle types, thus ensuring a smaller variation in flow rates between the two groups of three fluid process regions 828A–828C, 828D–828N. The common fluid that flows into the sample loading channels 850A–850N defined in the second layer 812 then carries the samples into the narrow loading channels 854A–854N defined in the third layer 813, through vias 856A–856N defined in the fourth and fifth layers 814 and 815, through the sample loading frit 859, through vias 860A–860N defined in the sixth layer 816 and onto/into each of the six fluid process regions 828A–828N defined in the seventh layer 817.

To prepare the device 810 for operation, one or more common fluids (e.g., mobile phase solvents or reagents) may be supplied to the device 810 through the common fluid inlet port 890 defined in the ninth layer 819. These common fluids may be pre-mixed upstream of the device 810 using a conventional micromixer. This common fluid distribution network is also used to supply common fluid during operation of the device 810, once the samples are loaded onto the fluid process regions 828A–828N. To prepare the device 810 for sample loading, common fluid flow is temporarily interrupted, an external interface (not shown) previously covering the sample loading ports 852A–852N is opened, and samples are supplied through the sample ports 852A–852N into the sample loading channels 850A–850N. The frits 877A–877N and the frit 859 provide substantial fluidic impedance that prevents fluid flow through the frits 877A–877N, 859A at low pressures. This ensures that the samples remain isolated within the sample loading channels 850A–850N during the sample loading procedure. Following sample loading, the sample loading ports 852A–852N are again sealed (e.g., with an external interface) and common fluid flow is re-initiated to carry the samples onto/into the fluid process regions 828A–828N defined in the seventh layer 817.

While the bulk of the common fluid that is supplied to each fluid process region 828A–828N travels downstream through the fluid process regions 828A–828N, a small split portion of each travels upstream through the fluid process regions 828A–828N in the direction of the waste port 886. The split portions of common fluid from each fluid process region 828A–828N that travel upstream are consolidated into a single waste stream that flows through the slurry distribution network comprising the two small forked channels 826A and 826B, slurry channels 823A and 823B, then through vias 834A and 834B, the short waste segments 836A and 836B, vias 838A and 838B, vias 839A and 839B, frit 884, vias 840A and 840B, a waste channel 882, to the waste port 886 to exit the device 810. The purpose of providing both an upstream and downstream path for each fluid process region 828A–828N is to allow the removal of air bubbles from the device 810 during device preparation.

Figure 27E:
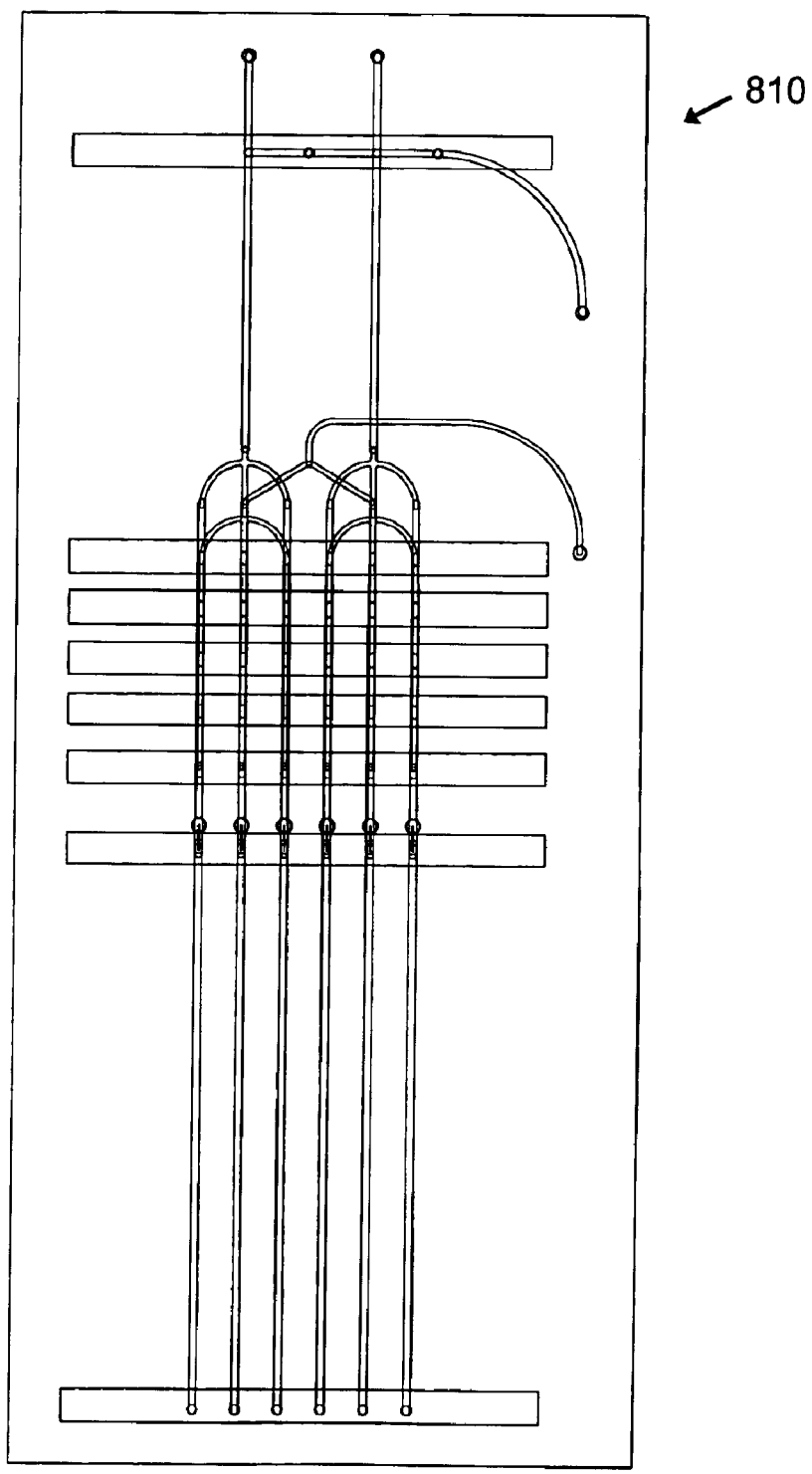
FIG. 27E is a top view of the assembled device of FIGS. 27A–27D.

FIG. 27E shows the top view of the assembled device 810. FIG. 27F shows the slurry distribution network 810D (comprising slurry channels 823A–823B, common fluid waste channel segments 836A–836B, solvent waste channel 882, two small forked channels 826A and 826B, six fluid process regions 828A–828N and six fluid process region outlet vias 830A–830N). FIG. 27G shows the common fluid network 810E (comprising channel segment 891, large forked channel 892, two small forked channels 893A and 893B, six common fluid channel segments 894A–894N, six common fluid channel segments 895A–895N, six common fluid channel segments 896A–896N, and six common fluid channel segments 897A–897N).

The composition of the common fluid may be static (e.g., for performing isocratic separations in multiple fluid process regions/separation columns 828A–828N) or subject to change over time (e.g., for performing gradient separations in multiple fluid process regions/separation columns 828A–828N). If multiple fluid process regions 828A–828N are provided in a single integrated device (such as the device 810) and the composition of the common fluid is subject to change over time, then at a common linear distance from the common fluid inlet port it is desirable for the common fluid to have a substantially identical composition from one fluid process regions 828A–828N to the next. This is achieved with the device 810 due to two factors: (1) volume of the path of each (split) common fluid substream is substantially the same to each fluid process regions 828A–828N; and (2) each flow path downstream of the fluidic (common fluid and sample) inlets is characterized by substantially the same impedance. The first factor, substantially equal substream flow paths, is promoted by design of the common fluid distribution network 810E, which includes branches of substantially equal lengths. The second factor, substantial equality of the impedance of each fluid process region, is promoted by the presence of multiple frits 877A–877N, which cause such an elevated impedance or flow resistance that their aggregate effect is to substantially reduce impedance differences caused by the presence of different solid materials in each of the two groups of fluid process regions 828A–828C, 828D–828N.

In another embodiment directed to methods development, a microfluidic device may include parallel fluid process regions in fluid communication with at least two common fluid inputs, but supply mixtures with different ratios of the two common fluids to each fluid process regions. An example such a device is provided in FIGS. 28A–28F. The device 910 includes six parallel fluid process regions 928A–928N containing solid material. Various types of functional solid materials may be used, such as stationary phase separation materials or catalyst materials, depending on the desired functionality of the device 910.

The device 910 may be constructed with eleven device layers 911–921, including multiple stencil layers 912–920 and two outer or cover layers 911, 921. Press-fit (external) interconnects (not shown) may be provided with either gasketed or gasketless interfaces. The device 910, its materials of construction, and methods for its manufacture may be the same as the previous device 710 described in connection with FIGS. 26A–26G.

Broadly, the device 910 includes various structures adapted to distribute solid (e.g., slurry) material among multiple fluid process regions 928A–928N, to retain the solid material within the device 910, to distribute at least two common fluids among the fluid process regions 928A–928N, to receive samples, to convey effluent streams from the device 910, and to convey a waste stream from the device 910.

Preferably, the separation channels 928A–928N are adapted to contain solid material, such as by including porous frits; namely, a downstream porous frit 931, a sample loading porous frit 959, a common fluid inlet frit 996 and a common fluid waste frit 985. Each frit 931, 959, 985 and 996 (and frit 977) may be fabricated from a strip of porous material, e.g., 1-mil thickness Celgard 2500 polypropylene membrane (55% porosity, 0.209×0.054 micron pore size, Celgard Inc., Charlotte, N.C.) and inserted into the appropriate regions between stacked device layers 911–921 before the layers 911–921 are laminated together. The average pore size of the frit material should be smaller than the average size of the solid particles. Preferably, an adhesiveless bonding method such as one of the methods described or referred to previously herein is used to interpenetrably bond the device layers 911–921 (and frits 931, 959, 985, 996 and 977) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 910.

A convenient method for packing solid material within the fluid process regions 928A–928N is to provide it in the form of a slurry (i.e., particulate material mixed with a suitable solvent). Slurry is supplied to the device 910 by way of a slurry inlet port 923 and channel structures defined in the sixth through tenth device layers 916–920. Specifically, the tenth layer 920 defines a slurry via 923A; the ninth layer 919 defines a slurry via 923B, two common fluid inlet vias 962B and 963B and six fluid process region outlet vias 930A–930N; the eighth layer 918 defines a slurry via 923C, a common fluid waste channel segment 936, two small forked channels 926A and 926B, a first common fluid splitter 960 and six fluid process region outlet vias 929A–929N. The seventh device layer 917 defines a slurry via 923D, a large forked channel 924 and the parallel fluid process regions 928A–928N. The sixth device layer 916 defines a second common fluid splitter 961 and a slurry channel 922 in fluid communication with the large forked channel 924 and the slurry via 923D defined in the seventh layer 917. In the aggregate, the slurry channel 922, large forked channel 924, and two small forked channels 926A and 926B form a slurry distribution network that communicates slurry from a single inlet (e.g., slurry inlet port 923) to (solid-containing) six fluid process regions 928A–928N and two common fluid splitters 960 and 961. Upon addition of particulate-containing slurry to the fluid process regions 928A–928N, the solid material is retained within the fluid process regions 928A–928N by one downstream porous frit 931, a sample loading porous frit 959, and common fluid waste frit 985, and within the common fluid splitters 960, 961 by way of a common fluid inlet frit 996. After the solid material is packed into the fluid process regions 928A–928N, a sealant (preferably substantially inert such as UV-curable epoxy) may be added to the slurry inlet port 923 to prevent the solid material contained within the fluid process regions 928A–928N from unpacking during operation of the device 910. The addition of sealant should be controlled to prevent blockage of the solvent waste channel segment 936. As before, porous monoliths may be used within the fluid process regions 928A–928N as an alternative to packed solid (particulate) matter.

The first layer 911 of the device 910 defines multiple sample ports/vias 952A–952N that permit samples to be supplied to sample loading channels 950A–950N defined in the second layer 912. The third through sixth layers 913–916 define a sample loading network designed to push samples onto each of the six fluid process regions 928A–928N. Each sample loading channel 950A–950N is in fluid communication with a different sample loading port 952A–952N. A sample loading fluid (which may be a mixture of two or more fluids) for providing sample loading utility flows from an inlet port 990 defined in the first layer 911, through a via 990A in the second layer 912, and into the large solvent channel 940 defined in the third layer 913. The sample loading fluid then flows to the large forked channel 942 in the fourth layer 914, through the two smaller forked channels 944A–944B in the fifth layer 915, through the vias 946A–946N in the fourth layer 914, through the frit 977, and through the vias 948A–948N in the third layer 913 that connect to the sample loading channels 950A–950N defined in the second layer 912. While the frit 977 technically does not retain any packing material within the device, it may be fabricated from the same material as the sample loading frit 959, the common fluid inlet frit 996, the outlet frit 931 and the solvent waste frit 985, which do retain packing material within the columns 928A–928N. The sample loading fluid that flows into the sample loading channels 950A–950N defined in the second layer 912 then carries the samples into the narrow loading channels 954A–954N defined in the third layer 913, through vias 955A–955N defined in the fourth and fifth layers 914 and 915, through the sample loading frit 959, through vias 956A–956F defined in the sixth layer 916 and onto each of the six fluid process regions 928A–928N defined in the seventh layer 917. To prepare the device 910 for sample loading, sample loading fluid flow is temporarily interrupted, an external interface (not shown) previously covering the sample loading ports 952A–952N is opened, and samples are supplied through the sample ports 952A–952N into the sample loading channels 950A–950N. The frits 977 and 959 provide substantial fluidic impedance that prevents fluid flow through the frits 977, 959 at low pressures. This ensures that the samples remain isolated within the sample loading channels 950A–950N during the sample loading procedure. Following sample loading, the sample loading ports 952A–952N are again sealed (e.g., with an external interface) and sample loading fluid flow is re-initiated to carry the samples onto the (solid-containing) fluid process regions 928A–928N defined in the seventh layer 917.

Once the samples are loaded onto the separation columns 928A–928N, the flow of sample loading fluid through the sample loading network is again interrupted. For sample processing, a first and a second common fluids (any or both of which may be mixtures) are supplied into first and second solvent inlet ports 962, 963, respectively, defined in the eleventh layer 921, and into each of the two common fluid splitters 960, 961. The common fluid splitters create unequal splitting of each common fluid, with a larger portion of the common fluid flow traveling down the branch nearest its inlet and a smaller portion of the common fluid flow traveling down the branch farthest from its inlet, with a gradient of flow in the branches between. Because the two common fluid splitters 960, 961 are mirror images, the net flow of common fluid to each fluid process region 928A–928N from the combined solvent splitters 960, 961 will be equal, but of a different mix ratio. The common fluids entering each of the fluid process regions 928A–928N will begin to mix at the point of overlap of the common fluid 960, 961 and the fluid process regions 928A–928N, and should be substantially mixed by the time the common fluid front reaches the samples that have been injected onto the fluid process regions 928A–928N through vias 956A–956N.

While the bulk of the common fluid that is supplied to each fluid process regions 928A–928N travels downstream through the fluid process regions 928A–928N and exits through the outlet vias 929A–929N, a small split portion of each travels further down the fluid process regions 928A–928N in the direction of the waste port 982. The split portions of common fluid from each fluid process region 928A–928N that travel toward the waste port 982 are consolidated into a single waste stream that flows through the slurry distribution network comprising the two small forked channels 926A and 926B, large forked channel 924, and slurry channel 922, then through via 934, the short waste segment 936, vias 938A and 938B, frit 985, via 938C, a waste channel 984, to the waste port 982 to exit the device 910. The purpose of providing a common fluid waste path downstream of the outlet vias 929A–929N for each fluid process region 928A–928N is to allow the removal of air bubbles from the device 910 while preparing the device 910 for operation.

FIG. 28E shows a top view of the assembled device 910. FIG. 28F shows the slurry distribution network 910D (comprising slurry channel 922, common fluid waste channel segment 936, common fluid waste channel 984, large forked channel 924, two small forked channels 926A and 926B, six fluid process regions 928A–928N, two common fluid splitters 960 and 961 and six fluid process region outlet vias 930A–930N). FIG. 28G shows the sample loading network 910G (comprising sample loading fluid channel 940, large forked channel 942, two smaller forked channels 944A–944B, sample loading channels 950A–950N, sample loading ports 952A–952N, and narrow loading channels 954A–954N).

The device 910 is designed to create a gradient of mixtures of two common fluids across the six separation channels 928A–928N. Because of the different path lengths from the inlet to the outlets of the common fluid splitters 960, 961 the common fluids flow into the device 910 at the two common fluid inlets 962, 963 are split unequally by the time they reach the overlap mixing region where the splitters 960, 961 overlap the six fluid process regions 928A–928N. The uneven splitting creates a different ratio of mixed common fluids for each of the six fluid process regions 928A–928N. In this manner, samples may be processed in parallel with only two common fluid supply elements (e.g., pumps) yet simultaneously subjected to different ratios of common fluids.

Various microfluidic tools, modules, and devices provided herein have been applied to perform syntheses and/or analyses. Modular or integrated microfluidic devices having regions for performing syntheses and analyses are contemplated.

It is to be understood that the illustrations and descriptions of views of individual microfluidic tools, devices and methods provided herein are intended to disclose components that may be combined in a working device. Various arrangements and combinations of individual tools, devices, and methods provided herein are contemplated, depending on the requirements of the particular application. The particular microfluidic tools, devices, and methods illustrated and described herein are provided by way of example only, and are not intended to limit the scope of the invention.

What is claimed is:

1. A microfluidic device comprising:
   a common first fluid inlet port;
   a first microfluidic splitting network in fluid communication with the common first fluid inlet port, the first splitting network including a plurality of branches;
   a plurality of sample inlet ports; and
   a plurality of flow-through microfluidic process regions in fluid communication with the first splitting network and the plurality of sample inlet ports, the plurality of process regions including a first process region and a second process region, each process region of the plurality of process regions containing a solid material and being associated with a different branch of the plurality of branches;
   wherein the first process region contains a first solid material, the second process region contains a second solid material, and the performance of the first process region is substantially different from the performance of the second process region.

2. The device of claim 1, further comprising a plurality of elevated flow resistance regions disposed downstream of the first splitting network and in fluid communication with the plurality of process regions; wherein:
   each process region of the plurality of process regions is associated with and in fluid communication with a different elevated flow resistance region of the plurality of elevated flow resistance regions;
   each process region of the plurality of process regions has a characteristic flow resistance; and each elevated flow resistance region of the plurality of elevated flow resistance regions has a characteristic flow resistance that is greater than the flow resistance of its associated process region of the plurality of process regions.

3. The device of claim 2 wherein the plurality of elevated flow resistance regions comprises at least one porous membrane.

4. The device of claim 3 wherein the at least one porous membrane is disposed lengthwise in a direction substantially perpendicular to the plurality of process regions.

5. The device of claim 2 wherein the plurality of elevated flow resistance regions are disposed upstream of the plurality of process regions.

6. The device of claim 1 wherein each elevated flow resistance region of the plurality of elevated flow resistance regions includes a plurality of flow resistance elements disposed in series.

7. The device of claim 1 wherein each elevated flow resistance region of the plurality of elevated flow resistance regions has a substantially equal characteristic flow resistance.

8. The device of claim 1, further comprising:
a common second fluid inlet port; and
a second microfluidic splitting network in fluid communication with the common second fluid inlet port, the second splitting network including a plurality of branches;
wherein the second splitting network is in fluid communication with the plurality of process regions.

9. The device of claim 1 wherein each solid material comprises packed particulate material.

10. The device of claim 1, further comprising:
a third fluid inlet port in fluid communication with the first process region of the plurality of process regions; and
a fourth fluid inlet port in fluid communication with the second process region of the plurality of process regions.

11. The device of claim 10, further comprising a plurality of outlet ports, wherein each process region of the plurality of process regions is in fluid communication with a different outlet port of the plurality of outlet ports.

12. The device of claim 1 wherein the first process region is larger than the second process region.

13. The device of claim 1 wherein the first solid material contained within the first process region has a first aggregate surface area, the second solid material contained within the second process region has a second aggregate surface area, and the first aggregate surface area is greater than the second aggregate surface area.

14. The device of claim 1 wherein the first solid material has a first composition, the second solid material has a second composition, and the first composition is different from the second composition.

15. The device of claim 1 wherein each of the first solid material and the second solid material comprises a catalyst material.

16. The device of claim 1 wherein each of the first solid material and the second solid material comprises separation media.

17. The device of claim 1 wherein each of the first solid material and the second solid material comprises a chromatographic separation material selected from the group consisting of: adsorbent, ion exchange, affinity, and size exclusion media.

18. The device of claim 1 wherein each of the first solid material and the second solid material comprises packed particulate material, the device further comprising at least one retaining element adapted to retain packed particulate material within the first process region and the second process region.

19. The device of claim 18 wherein the packed particulate material has an average particle size, the retaining element includes a porous region having an average pore size, and the average particle size is greater than the average pore size.

20. The device of claim 1, further comprising a plurality of substantially planar device layers including a plurality of stencil layers wherein the first splitting network and the plurality of process regions are defined in the plurality of stencil layers.

21. The device of claim 20 wherein the plurality of device layers comprises substantially planar adhesiveless polymer layers.

22. The device of claim 21 wherein the plurality of device layers is interpenetrably bound together to form a substantially sealed adhesiveless device.

23. The device of claim 21 wherein the plurality of polymer layers comprises an unoriented polyolefin material.

24. A microfluidic device comprising:
a first fluid inlet port;
a second fluid inlet port;
a first microfluidic splitting network in fluid communication with the first fluid inlet port, the first splitting network including a first plurality of microfluidic branch channels, each branch channel of the first plurality of branch channels having a fluidic impedance;
a second microfluidic splitting network in fluid communication with the second fluid inlet port, the second splitting network including a second plurality of microfluidic branch channels, each branch channel of the second plurality of branch channels having a fluidic impedance;
a plurality of mixing regions in fluid communication with the first splitting network and the second splitting network, and
a plurality of separation regions in fluid communication with the plurality of mixing regions.
wherein any of the first splitting network and the second splitting network includes branch channels of different impedances, and each mixing region of the plurality of mixing regions effects mixing of a first fluid and a second fluid in different proportions compared to each other mixing region of the plurality of mixing regions.

25. The device of claim 24 wherein any of the first plurality of branch channels and the second plurality of branch channels includes branch channels of different lengths.

26. The device of claim 24 wherein each mixing region of the plurality of mixing regions is a passive mixing region.

27. The device of claim 24 wherein each mixing region of the plurality of mixing regions includes a channel overlap region.

28. The device of claim 24 wherein any of the first splitting network and the second splitting network is substantially filled with packed particulate material.

29. The device of claim 28, further including at least one porous material adapted to retain the packed particulate material in any of the first splitting network and the second splitting network, wherein the packed particulate material has an average particle size, the at least one porous material has an average pore size, and the average particle size is greater than the average pore size. Filter materials may be used within separation regions if desired.

30. The device of claim 29 wherein the at least one porous material comprises at least one porous membrane.

31. The device of claim 24 wherein each separation region of the plurality of separation regions comprises a filter material.

32. The device of claim 24 wherein the plurality of separation regions comprises at least one porous membrane.

33. The device of claim 24 wherein each separation region of the plurality of separation regions comprises packed particulate material.

34. The device of claim 33, further comprising at least one porous material adapted to retain the packed particulate material within the device, wherein the at least one porous material has an average pore size, the packed particulate material has an average particle size, and the average pore size is smaller than the average particle size.

35. The device of claim 34 wherein the at least one porous material comprises at least one porous membrane.

36. The device of claim 24, further comprising a plurality of sample inlet ports in fluid communication with the plurality of separation regions downstream of the plurality of mixing regions.

37. The device of claim 24, further comprising a plurality of substantially planar stencil layers, wherein the first splitting network, the second splitting network, and the plurality of separation regions are defined in the plurality of stencil layers.

38. The device of claim 37 wherein the plurality of device layers comprises substantially planar adhesiveless polymer layers.

39. The device of claim 38 wherein the plurality of polymer layers comprises an unoriented polyolefin material.

40. The device of claim 24 wherein the plurality of device layers are interpenetrably bound together to form a substantially sealed adhesiveless device.

41. The device of claim 24, further comprising a plurality of outlet ports, wherein each separation region of the plurality of separation regions is in fluid communication with a different outlet port of the plurality of outlet ports.

* * * * *